US012779454B2

(12) United States Patent
Seville et al.

(10) Patent No.: US 12,779,454 B2
(45) **Date of Patent: *Nov. 3, 2026**

(54) LOOP-MEDIATED ISOTHERMAL AMPLIFICATION (LAMP) ON A SOLID-PHASE MEDIUM

(71) Applicants: Purdue Research Foundation, West Lafayette, IN (US); Raytheon BBN Technologies, Corp., Cambridge, MA (US)

(72) Inventors: Jordan Seville, Delran, NJ (US); Darby McChesney, Lawrenceville, NJ (US); Frank M. LaDuca, Warrensburg, NY (US); Jiangshan Wang, West Lafayette, IN (US); Murali Kannan Maruthamuthu, Lafayette, IN (US); Andres Dextre, West Lafayette, IN (US); Mohit Verma, West Lafayette, IN (US)

(73) Assignees: RTX BBN TECHNOLOGIES, INC., Cambridge, MA (US); PURDUE RESEARCH FOUNDATION, West Lafayette, IN (US)

( * ) Notice: Subject to any disclaimer, the term of this patent is extended or adjusted under 35 U.S.C. 154(b) by 1221 days.

This patent is subject to a terminal disclaimer.

(21) Appl. No.: 17/576,974

(22) Filed: Jan. 16, 2022

(65) Prior Publication Data

US 2022/0340984 A1 Oct. 27, 2022

Related U.S. Application Data

(60) Provisional application No. 63/148,527, filed on Feb. 11, 2021, provisional application No. 63/138,323, (Continued)

(51) Int. Cl.

| | |
|---|---|
| ***C12Q 1/70*** | (2006.01) |
| ***B01L 3/00*** | (2006.01) |
| ***B01L 7/00*** | (2006.01) |
| ***C12Q 1/6806*** | (2018.01) |
| ***C12Q 1/6844*** | (2018.01) |
| ***C12Q 1/6848*** | (2018.01) |
| ***C12Q 1/6851*** | (2018.01) |
| ***C12Q 1/686*** | (2018.01) |
| ***C12Q 1/6888*** | (2018.01) |
| ***G01J 3/52*** | (2006.01) |

(Continued)

(52) U.S. Cl.

CPC ............... *B01L 3/5023* (2013.01); *B01L 7/00* (2013.01); *C12Q 1/6806* (2013.01); *C12Q 1/6844* (2013.01); *C12Q 1/6848* (2013.01); *C12Q 1/6888* (2013.01); *C12Q 1/70* (2013.01); *C12Q 1/701* (2013.01); *G01J 3/524* (2013.01); *G01K 7/02* (2013.01); *G01K 7/22* (2013.01); *G01N 1/44* (2013.01); *G01N 21/78* (2013.01); *G01N 33/526* (2013.01); *B01L 2200/04* (2013.01); *B01L 2200/0689* (2013.01); *B01L 2200/10* (2013.01); *B01L 2200/16* (2013.01); *B01L 2300/0681* (2013.01); *B01L 2300/069* (2013.01); *B01L 2300/0809* (2013.01); *B01L 2300/0825* (2013.01); *B01L 2300/0832* (2013.01); *B32B 2250/04* (2013.01); *C12Q 2600/112* (2013.01); *G01J 2003/467* (2013.01)

(58) Field of Classification Search

CPC ...... C12Q 1/6844; C12Q 1/6806; C12Q 1/70; B01L 2200/10; B32B 2250/04

See application file for complete search history.

(56) References Cited

U.S. PATENT DOCUMENTS 5,955,377 A 9/1999 Maul et al.
6,240,791 B1 6/2001 Kenney
(Continued)

FOREIGN PATENT DOCUMENTS

AU 621236 B2 3/1992
CA 3203298 A1 7/2022
(Continued)

OTHER PUBLICATIONS

Safavieh et al., "A simple cassette as point-of-care diagnostic device for naked-eye colorimetric bacteria detection", Analyst, 2014, 139:482-487.*

(Continued)

*Primary Examiner* — Barry A Chestnut
(74) *Attorney, Agent, or Firm* — CANTOR COLBURN LLP

(57) ABSTRACT

The present disclosure is drawn to loop-mediated isothermal amplification (LAMP) reaction assemblies including a substantially hygroscopic agent free LAMP reagent mixture in combination with a solid-phase reaction medium. The present disclosure also includes systems for a chromatic LAMP analysis including a substantially non-reactive solid phase reaction medium, and a non-interfering reagent mixture. The present disclosure also includes solid phase LAMP reaction mediums comprising a substrate, an adhesive layer disposed on the substrate, a reaction layer disposed on the adhesive layer, and a spreading layer disposed on the reaction layer. The present disclosure also includes methods of testing for a presence of a target nucleotide sequence including providing a biological sample, and dispensing the sample into a test environment having a solid phase reaction medium in combination with a LAMP reagent mixture and a pH sensitive dye.

22 Claims, 43 Drawing Sheets

Related U.S. Application Data filed on Jan. 15, 2021, provisional application No. 63/138,341, filed on Jan. 15, 2021, provisional application No. 63/138,312, filed on Jan. 15, 2021, provisional application No. 63/138,337, filed on Jan. 15, 2021, provisional application No. 63/138,310, filed on Jan. 15, 2021, provisional application No. 63/138,320, filed on Jan. 15, 2021, provisional application No. 63/138,321, filed on Jan. 15, 2021, provisional application No. 63/138,316, filed on Jan. 15, 2021, provisional application No. 63/138,318, filed on Jan. 15, 2021, provisional application No. 63/138,314, filed on Jan. 15, 2021.

(51) Int. Cl.

| | |
|---|---|
| ***G01K 7/02*** | (2021.01) |
| ***G01K 7/22*** | (2006.01) |
| ***G01N 1/44*** | (2006.01) |
| ***G01N 21/78*** | (2006.01) |
| ***G01N 33/52*** | (2006.01) |
| *G01J 3/46* | (2006.01) |

(56) References Cited

U.S. PATENT DOCUMENTS

| | | | |
|---|---|---|---|
| 7,682,565 | B2 | 3/2010 | Linton et al. |
| 8,921,085 | B2 | 12/2014 | Battrell et al. |
| 10,619,189 | B2 | 4/2020 | Sitton et al. |
| 10,968,493 | B1 | 4/2021 | Tanner et al. |
| 2002/0150501 | A1 | 10/2002 | Robertson et al. |
| 2006/0000296 | A1 | 1/2006 | Salter |
| 2007/0046941 | A1 | 3/2007 | Mestha et al. |
| 2008/0194426 | A1 | 8/2008 | Goodman et al. |
| 2008/0268495 | A1 | 10/2008 | Skold et al. |
| 2010/0291588 | A1 | 11/2010 | Mcdevitt et al. |
| 2010/0331725 | A1 | 12/2010 | Libby et al. |
| 2011/0117549 | A1 | 5/2011 | Miyamoto et al. |
| 2011/0150705 | A1 | 6/2011 | Doyle et al. |
| 2011/0165595 | A1 | 7/2011 | Catanzaro et al. |
| 2011/0171754 | A1 | 7/2011 | Redmond et al. |
| 2012/0142070 | A1 | 6/2012 | Battrell et al. |
| 2013/0130257 | A1 | 5/2013 | Hillebrand et al. |
| 2013/0132006 | A1 | 5/2013 | Gwynn et al. |
| 2014/0154789 | A1 | 6/2014 | Polwart et al. |
| 2014/0170661 | A1 | 6/2014 | Lamura et al. |
| 2015/0346105 | A1 | 12/2015 | Gutsell et al. |
| 2015/0353919 | A1 | 12/2015 | Mielke et al. |
| 2015/0361511 | A1 | 12/2015 | Lee et al. |
| 2016/0008809 | A1 | 1/2016 | Li et al. |
| 2016/0139156 | A1 | 5/2016 | Lakdawala |
| 2016/0231251 | A1 | 8/2016 | Ou et al. |
| 2016/0310948 | A1 | 10/2016 | Nowakowski et al. |
| 2016/0319354 | A1 | 11/2016 | Tocigl et al. |
| 2017/0248622 | A1 | 8/2017 | Khattak et al. |
| 2018/0021777 | A1 | 1/2018 | Giri et al. |
| 2018/0141041 | A1 | 5/2018 | Paek |
| 2018/0299385 | A1 | 10/2018 | Honda et al. |
| 2018/0313743 | A1 | 11/2018 | Dixon et al. |
| 2019/0083975 | A1 | 3/2019 | Mitra et al. |
| 2019/0092536 | A1 | 3/2019 | Freedman et al. |
| 2019/0218604 | A1 | 7/2019 | Liang et al. |
| 2019/0226985 | A1 | 7/2019 | Roberts et al. |
| 2019/0369094 | A1 | 12/2019 | Ishikawa et al. |
| 2020/0063197 | A1 | 2/2020 | Meldrum et al. |
| 2020/0126226 | A1 | 4/2020 | Adiri et al. |
| 2020/0126266 | A1 | 4/2020 | Adiri et al. |
| 2020/0181720 | A1 | 6/2020 | Abudayyeh et al. |
| 2020/0309702 | A1 | 10/2020 | Barron et al. |
| 2021/0275663 | A1 | 9/2021 | Jiao et al. |
| 2022/0160581 | A1 | 5/2022 | Rigby |
| 2022/0203365 | A1 | 6/2022 | Abraham et al. |
| 2022/0226817 | A1 | 7/2022 | Horvath et al. |
| 2022/0228205 | A1 | 7/2022 | Seville et al. |
| 2022/0228226 | A1 | 7/2022 | Seville et al. |
| 2022/0228956 | A1 | 7/2022 | Horvath et al. |
| 2022/0235408 | A1 | 7/2022 | Adler et al. |
| 2022/0252518 | A1 | 8/2022 | Adler et al. |
| 2022/0280081 | A1 | 9/2022 | Andeshmand et al. |
| 2022/0290261 | A1 | 9/2022 | Davidson et al. |
| 2022/0291246 | A1 | 9/2022 | Joris et al. |
| 2022/0380858 | A1 | 12/2022 | Gavin et al. |
| 2022/0403460 | A1 | 12/2022 | Horvath et al. |
| 2023/0014132 | A1 | 1/2023 | Seville et al. |
| 2024/0376492 | A1 | 11/2024 | Christen |

FOREIGN PATENT DOCUMENTS

| | | | |
|---|---|---|---|
| CA | 3203453 | A1 | 7/2022 |
| CN | 107419027 | A | 12/2017 |
| CN | 108384870 | A | 8/2018 |
| CN | 111330002 | A | 6/2020 |
| CN | 111378784 | A | 7/2020 |
| CN | 111500778 | A | 8/2020 |
| CN | 111518947 | A | 8/2020 |
| CN | 112111607 | A | 12/2020 |
| CN | 112342318 | A | 2/2021 |
| CN | 112739833 | A | 4/2021 |
| EP | 4278001 | A1 | 11/2023 |
| JP | 2013519884 | A | 5/2013 |
| JP | 2014198029 | A | 10/2014 |
| JP | 2015062406 | A | 4/2015 |
| JP | 2016534357 | A | 11/2016 |
| JP | 2018515100 | A | 6/2018 |
| WO | 2008101732 | A1 | 8/2008 |
| WO | WO 2013/067272 | A1 | 5/2013 |
| WO | WO 2014/152656 | A1 | 9/2014 |
| WO | 2015033229 | A2 | 3/2015 |
| WO | WO 2015/103293 | A2 | 7/2015 |
| WO | WO 2016/183012 | A1 | 11/2016 |
| WO | WO 2017/160836 | A1 | 9/2017 |
| WO | WO 2018/170340 | A1 | 9/2018 |
| WO | 2019073049 | A1 | 4/2019 |
| WO | WO 2019/109092 | A1 | 6/2019 |
| WO | 2019149963 | A1 | 8/2019 |
| WO | 2020084637 | A1 | 4/2020 |
| WO | WO 2020/251460 | A1 | 12/2020 |
| WO | WO 2020/257356 | A2 | 12/2020 |
| WO | 2021183921 | A1 | 9/2021 |
| WO | WO 2021/216728 | A1 | 10/2021 |
| WO | 2022155546 | A1 | 7/2022 |
| WO | 2022155547 | A1 | 7/2022 |
| WO | 2022155548 | A1 | 7/2022 |

OTHER PUBLICATIONS

Dou, Maowei et al.; "A Versatile PDMS/Paper Hybrid Microfluidic Platform for Sensitive Infectious Disease Diagnosis"; Anal. Chem. 86, pp. 7978-7986 (2014).

Dou, Maowei et al.; "A Versatile PDMS/Paper Hybrid Microfluidic Platform for Sensitive Infectious Disease Diagnosis"; Anal. Chem. 86, pp. 7978-7986; Supplemental S1-S7 (2014).

Nery, E.W. et al.; "Sensing approaches on paper-based devices: a review," Anal. Bioanal. Chem.; 405; pp. 7573-7595 (2013).

Bhadra, Sanchita et al.; High-surety isothermal amplification an detection of SARS-CoV-2, including with crude enzymes bioRxiv; Jul. 7, 2020; SP055912874; DOI: 10.1101/2020.04.13.039941.

Carrio, Adrian et al.; "Automated Lo-Cost Smartphone-Based Lateral Flow Saliva Test Reader for Drugs-of-Abuse Detection" Sensors; vol. 15, No. 12; Nov. 24, 2015; pp. 29569-29593; XP055257628; DOI: 10.3390/s151129569.

Davidson, Josiah Levi et al.; "A paper-based colorimetric molecular test for SARS-CoV-2 in saliva" Biosensors and Bioelectronics: X; vol. 9; Dec. 9, 2021; p. 100076; XP055911157; https://doi.org/10.1016/j.biosx.2021.100076.

Ganguli, A et al.; "Hands-free smartphone-based diagnostics for simultaneous detection of Zika, Chikungunya, and Dengue at point-of-care" Biomedical Microdevices; vol. 19, No. 4; Aug. 22, 2017; pp. 1-13; XP036372395; ISSN: 1387-2176; DOI: 10.1007/S10544-017-0209-9.

(56) References Cited

OTHER PUBLICATIONS

Hardinge, Patrick et al.; "Reduced False Positives and Improved Reporting of Loop-Mediated Isothermal Amplification using Quenched Fluorescent Primers" Scientific Reports; vol. 9, No. 1; Dec. 1, 2019; XP055912878; DOI: 10.1038/s41598-019-43817-z.

Howson, Emma et al.; "Preliminary optimization of a simplified sample preparation method to permit direct detection of SARS-CoV-2 within saliva samples using reverse-transcription loop-medicated isothermal amplification (RT-LAMP)" Journal of Virological Methods, Elsevier Bv, NL; vol. 289; Dec. 20, 2020; XP086476416; ISSN: 0166-0934; DOI: 10.1016/j.jviromet.2020.114048.

Huang, Wei E.; "RT LAMP for rapid diagnosis of coronavirus SARS-CoV-2" Microbial Biotechnology; vol. 13, No. 4; Apr. 25, 2020; pp. 950-961; XP055733462; ISSN: 1751-7915; DOI: 10.1111/1751-7915.13586.

Kellner, Max J. et al.; A rapid, highly sensitive and open-access SARS-CoV-2 detection assay for laboratory and home testing; bioRxiv; Jun. 23, 2020; XP055911082; DOI: 10.1101/2020.06.23.166397.

Labarre, Paul et al.; "Instrument-free nucleic acid amplification assays for global health settings" Sensing Technologies for Gloval Health, Military Medicine, Disaster Response, and Environivental Monitoring; and Bioivietric Technology for Human Identification VIII; SPIE; vol. 8029, No. 1; May 13, 2011; pp. 1-15; XP060014496.

Lalli, Matthew et al.; "Rapid and extraction-free detection of SARS-CoV-2 from saliva with colorimetric LAMP" medRxiv; Aug. 6, 2020; pp. 1-34; XP055791998; DOI: 10.1101/2020.05.07.20093542; www.ncbi.nlm.nih.gov/pmc/articles/PMC7273276/pdf/nihpp-2020.05.07.20093542.pdf.

Momen-Heravi, Fatemeh; "Impact of Biofluid Viscosity on Size and Sedimentation Efficiency of the Isolated Microvesicles" Frontiers in Physiology; vol. 3; Jan. 1, 2012; XP055189135; ISSN: 1664-042X; DOI: 10.3389/fphys.2012.00162.

Park, Gun-Soo et al.; "Development of Reverse Transcription Loop-Mediated Isothermal Amplification Assays Targeting Severe Acute Respiratory Syndrome Coronavirus 2 (SARS-CoV-2)" The Journal of Molecular Diagnostics; vol. 22, No. 6; Jun. 1, 2020; pp. 729-735; XP055796358; https://doi.org/10.1016/j.jmoldx.2020.03.006.

Qian, Jason et al.; "An enhanced isothermal amplification assay for viral detection" Nature Communications; vol. 11, No. 1; Nov. 0, 2020; XP055870470; DOI: 10.1038/s41467-020-19258-y; http://www.nature.com/articles/s41467-020-19258-y.

Rabe, Brian, et al.; SARS-CoV-2 detection using isothermal amplification and a rapid, inexpensive protocol for sample inactivation and purification' Proceedings of the National Academy of Sciences; vol. 117, No. 39; Sep. 8, 2020; pp. 24450-24458; XP055910088; ISSN: 0027-8424; DOI: 10.1073/pnas.2011221117.

Safavieh, Mohammadali et al.; "Emerging Loop-Mediated Isothermal Amplification-Based Microchip and Microdevice Technologies for Nucleic Acid Detection" ACS Biometerials Science and Engineering; vol. 2, No. 3; Mar. 14, 2016; pp. 278-294; XP055872000; ISSN: 2373-9878.

Schermer, Bernard et al.; "Rapid SARS-CoV-2 Testing in Primary Material Based on a Novel Multiplex RT-LAMP Assay" PLOS One; vol. 15, No. 11; Nov. 2, 2020; pp. 1-13 XP055824117; https://doi.org/10.1371/journal.pone.0238612.

Stedtfeld, Robert D. et al.; "Static self-directed sample dispensing into a series of reaction wells on a microfluidic card for parallel genetic detection of microbial pathogens" Biomedical Microdevices, Spinger US, New York; Vol. 17; No. 5; Aug. 11, 2015; pp. 1-12; XP035552426; ISSN: 1387-2176; DOI: 10.1007/810544-015-9994-1

Svendsen, Winnie E.; "Lab-on-a-Chip Devices and Micro-Total Analysis Systems" In: Department of Micro- and Nan0technology Technical University of Denmark Kgs. Lyngby Denmark; Oct. 9, 2015; XP055714359; ISBN: 978-3-319-08687-3; pp. 112-113.

Tanner, Nathan et al.; "Visual detection of isothermal nucleic acid amplification using pH-sensitive dyes" Biotechniques; vol. 58, No. 2; Feb. 1, 2015; pp. 59-68; SP055245831; DOI: 10.2144/000114253.

Thapa, Jeewan et al.; "Direct detection of *Mycobacterium tuberculosis* in clinical samples by a dry methyl green loop-mediated isothermal amplification (LAMP) method" Tuberculosis, Elsevier, SG; vol. 117; May 21, 2019; pp. 1-6; XP085754043; ISSN: 1472-9792; DOI: 10.1016/J.TUBE/2019.05.004.

Thompson, Dorian et al.; "Mini review: Recent progress in RT-LAMP enabled Covid-19 detection" Sensors and Actuators reports; Aug. 15, 2020; XP055911165; www.ncbi.nlm.nih.gov/pmc/articles/PMC7428436/pdf/main/pdf.

Yang, Qing et al.; "Saliva TwoStep for rapid detection of symptomatic SARS-CoV-2 carriers" ELIFE; vol. 10; Mar. 29, 2021; XP055875382; DOI: 10.7554/eLife.65113.

Yin, Kun et al.; "Synergistically enhanced colorimetric molecular detection using smart cup: a case for instrument-free HPV-associated cancer screening" Theranositics; vol. 9, No. 9; Jan. 1, 2019; pp. 2637-2645; XP055911179; ISSN: 1838-7460; DOI: 10.7150/thno.32224.

Zhang, Yinhua et al.; "Enhancing colorimetric loop-mediated isothermal amplification speed and sensitivity with guanidine chloride" Biotechniques; vol. 69, No. 3; Sep. 1, 2020; pp. 178-185; XP055888013; ISSN: 0736-6205; DOI: 10.2144/btn-2020-0078.

Baliga et al.; "Salivary pH: A diagnostic biomarker"; Journal of Indian Society of Periodontology, vol. 17, Issue No. 4; pp. 461-465 (2013) DOI:10.4103/0972-124X.118317.

Brown, T. et al.; "Direct detection of SARS-CoV-2 RNA using high-contrast pH-sensitive dyes"; Journal of Biomolecular Techniques, vol. 32, Issue No. 3; pp. 121-133; DOI: 10.7171/jbt.21-3203-007 (2021).

CA Office Action for Application No. 3,203,298, mailed May 30, 2024, 5 pages.

CA Office Action for Application No. 3,203,453, mailed Jul. 31, 2024, 6 pages.

CA Office Action for Application No. 3,203,454, mailed Jul. 29, 2024, 4 pages.

English Translation of JP Office Action for Patent Application No. 2023-542512, mailed Jul. 30, 2024, 5 pages.

English Translation of JP Office Action for Patent Application No. 2023-542674, mailed Jul. 2, 2024, 11 pages.

English Translation of JP Office Action for Patent Application No. 2023-542850, mailed Aug. 20, 2024, 5 pages.

EP Office Action for Application No. 22703180.4, mailed Nov. 14, 2023, 4 pages.

Helton et al.; Conditioning saliva for use in microfluidic biosensor; Lab Chip, 2008, 8, 1847-1851.

JP Office Action for Patent Application No. 2023-542512, mailed Jul. 30, 2024, 6 pages.

JP Office Action for Patent Application No. 2023-542674, mailed Jul. 2, 2024, 9 pages.

JP Office Action for Patent Application No. 2023-542850, mailed Aug. 20, 2024,4 pages.

Kaarj, et al. "Simpler, Faster, and sensitive Zika Virus Assay Using Smartphone Detection of Loop-mediated Isothermal Amplification on Paper Microfluidic Chips", Scientific Reports, (2018) 8: 12438; pp. 1-11.

Notification of Transmittal of the International Search Report and the Written Opinion of the International Searching Authority, or the Declaration; PCT/US2022/012634; Apr. 20, 2022, 15 pages.

Notification of Transmittal of the International Search Report and the Written Opinion of the International Searching Authority, or the Declaration; PCT/US2022/012635; Apr. 22, 2022, 13 pages.

Notification of Transmittal of the International Search Report and the Written Opinion of the International Searching Authority, or the Declaration; PCT/US2022/012636; Apr. 25, 2022, 14 pages.

Notification of Transmittal of the International Search Report and the Written Opinion of the International Searching Authority, or the Declaration; PCT/US2022/012637; May 16, 2022, 13 pages.

Notification of Transmittal of the International Search Report and the Written Opinion of the International Searching Authority, or the Declaration; PCT/US2022/012639; Apr. 26, 2022, 15 pages.

(56) References Cited

OTHER PUBLICATIONS

Notification of Transmittal of the International Search Report and the Written Opinion of the International Searching Authority, or the Declaration; PCT/US2022/012640; Apr. 26, 2022, 15 pages.
Notification of Transmittal of the International Search Report and the Written Opinion of the International Searching Authority, or the Declaration; PCT/US2022/012641; Apr. 20, 2022, 20 pages.
Notification of Transmittal of the International Search Report and the Written Opinion of the International Searching Authority, or the Declaration; PCT/US2022/012642; Jul. 13, 2022, 21 pages.
Notification of Transmittal of the International Search Report and the Written Opinion of the International Searching Authority, or the Declaration; PCT/US2022/016183; Jul. 25, 2022, 22 pages.
Robinson, et al.; "Use of throat swab or saliva specimens for detection of respiratory viruses in children"; Clinical Infectious Diseases, vol. 46; pp. e61-e64 (2008) DOI: 10.1086/529386.
Rodriguez, N. et al.; "Paper-Based RNA Extraction in Situ Isothermal Amplification and Lateral Flow Detection for Low-Cost Rapid Diagnosis of Influenza A (H1N1) from Clinical Specimens"; Anal Chem 87; pp. 7872-7879 (2015).
AU Examination Report, Application No. 2022207504, date of mailing Nov. 22, 2024, 4 pages.
AU Examination Report, Application No. 2022208714, date of mailing Nov. 25, 2024, 4 pages.
AU Examination Report; Application No. 2022207503, date of mailing Nov. 22, 2024, 4 pages.
Bst DNA polymerase-NEB pdf—Downloaded from Internet on Dec. 1, 2024. (Year: 2024); 5 pages.
CA Office Action for Application No. 3,203,298, mailed Feb. 24, 2025, 4 pages.
CA Office Action for Application No. 3,203,453, mailed Feb. 20, 2025, 4 pages.
CA Office Action for Application No. 3,203,454, mailed Feb. 20, 2025, 4 pages.
EP Office Action for Application No. 22703177.0, mailed Feb. 20, 2025, 8 pages.
EP Office Action for Application No. 22703178.8, mailed Feb. 21, 2025, 11 pages.
European Office Action, Application No. 22703179.6, mailed Mar. 13, 2025, 7 pages.
European Office Action, Application No. 22704038.3, mailed Mar. 14, 2025, 8 pages.
European Office Action, Application No. 22707530.6, mailed Mar. 17, 2025, 5 pages.
Farshidfar, et al., "The Potential Role of Smartphone-Based Microfluidic Systems for Rapid Detection of COVID-19 Using Saliva Specimen", Aug. 1, 2020, Molecular Diagnosis & Therapy; vol. 24, No. 4; 2020; pp. 371-373; 3 pages.
Hyun et al., "Salivary Exosome and Cell-Free DNA for Cancer Detection", Jul. 4, 2018, Micromachines 2018, vol. 9, No. 7; MDPI; 13 pages.
International Office Action; JP Application No. 2023542512, mailed Jan. 21, 2025; 5 pages, Machine Translation.
Japan Office Action, Application No. 2023-542850, mailed Mar. 4, 2025, with English Translation, 7 pages, machine translation.
Japanese Office Action, Application No. 2023542674, mailed Mar. 18, 2025, with machine translation, 13 pages.
Miocevic, et al., "Quantitative Lateral Flow Assays for Salivary Biomarker Assessment: A Review", Frontiers in Public Health; vol. 5 Article 133; Jun. 2017;13 pages.
Notification of Transmittal of the International Preliminary Report on Patentability; PCT/US2022/012635; Jul. 4, 2023, 7 pages.
Notification of Transmittal of the International Preliminary Report on Patentability; PCT/US2022/012636; Jul. 4, 2023, 8 pages.
Notification of Transmittal of the International Preliminary Report on Patentability; PCT/US2022/012637; Jul. 4, 2023,8 pages.
Oasis ("Pure-SALTM: Oral Specimen Collection System" Oasis diagnostics, 2016, Vancouver WA) (Year: 2016), 10 pages.
Promega ("TE Buffer", available at https://www.promega.com/products/biochemicals-and-labware/biochemcial-buffers-and-reagents/te-buffer_-1x_-molecular-biology-grade/?catNUM=V6231, accessed on Nov. 26, 2024) (Year: 2024), 5 pages.
Reuter, et al., "Loop-mediated amplification as promising on-site detection approach for *Legionelle pneumophila* and *Legionelle* spp", Dec. 12, 2019, Applied Microbiology and Biotechnology, col. 104 No. 1, (2020), pp. 405-415, 11 pages.
Schroff, "100% Solids: A compelling solution to the challenge of medical adhesive coating", SAE Media Group, 2015, 8 pages.
Seok et al., "Lab-on-paper for all-in-one molecular diagnostics (LAMDA) of zika, dengue, and chikungunya virus from human serum", Biosensors and Bioelectronics 165 (2020), 8 pages.
Seok,, "A Paper-Based Device for Performing Loop-Mediated Isothermal Amplification with Real-Time Simultaneous Detection of Multiple DNA Targets", Theranostics vol. 7, ZIssue 8, 2017, p. 2220-2230; 11 pages.
Short, et al. "Effect of Interfacing on colorimetric reactions for deoxyribonucelic acid", Anal. Biochem. 1986, p. 251-268.
WarmStart® RTx Reverse Transciptase-NEB pdf—downloaded from Internet on Dec. 1, 2024. (Year: 2024), 3 pages.
Yager, et al., "Microfluidic diagnostic technologies for global public health", Nature; vol. 442, Jul. 2006, pp. 412-418; 8 pages.
Adhesives Research. Point of Care Innovative Solutions [online] Adhesives Research; Oct. 2020 [retrieved Jun. 27, 2025] Available from: https://www.adhesivesresearch.com/china/wp-content/uploads/2010/10/Point-of-Care-Innovative-Solutions.pdf (Year: 2020).
Ahn et al., "Rapid and simple colorimetric detection of multiple influenza viruses infecting humans using a reverse transcriptional loop-mediated isothermal amplification (RT-LAMP) diagnostic platform" BMC Infectious Diseases, vol. 19 (2019) p. 676.
Byers et al. "Versatile printed microheaters to enable low-power thermal control in paper diagnostics" Analyst 145.1 (2020) pp. 184-196.
CalculatorSoup L. Rectangular prism calculator (cuboid) [online] [retrieved Jun. 27, 2025] Available from: https://www.calculatorsoup.com/calculators/geometry-solids/rectangularprism.php (Year 2023).
Carter et al. "Lyophilized visually readable loop-mediated isothermal reverse transcriptase nucleic acid amplification test for detection Ebola Zaire RNA" Journal of virological methods 244 (Jun. 2017) pp. 32-38.
Grade 1 qualitative filter paper, standard, 30mm circle, 100/PK [online] [retrieved Jun. 27, 2025] Available from: https://www.tischscientific.com/whatman/filter-papers-cellulose-filters-qualitative-filter-papers-1001-329 (Year: 2025).
Lin et al., "Influence of water evaporation/absorption on the stability of glycerol-water marbles" RSC Advances, vol. 9 (2019) p. 34465.
Marshall Scientific "Biorad CFX96 touch real-time PCR system" [online] 2025 [retrieved Sep. 10, 2025 ] Retrieved from the internet: https://www.marshallscientific.com/Biorad-CFX96-Touch-Real-Time-PCR-System-p/bio-cfx96t.htm.
Montrasio "Development of a software application for loop-mediated isothermal amplification (LAMP) primer design" (Year: 2016) 137 pages.
Naik et al., "Nucleic Acid amplification on paper substrates" Paper Microfluidics (2019) pp. 115-146.
Office Action issued in Australian Patent Application No. 2022207504; Date of Mailing Aug. 27, 2025 (4 pages).
Office Action issued in Japanese Patent Application No. 2023-542512; Date of Mailing Jul. 8, 2025 (17 pages).
Office Action issued in Taiwan Patent Application No. 111101754; Date of Mailing Sep. 19, 2025 (11 pages).
Office Action issued in Taiwan Patent Application No. 111101756; Date of Mailing Sep. 18, 2025 (11 pages).
Rodriguez et al. "Paper-based RNA extraction, in situ isothermal amplification, and lateral flow detection for low-cost, rapid diagnosis of influenza A (H1N1) from clinical specimens" Analytical chemistry 87.15 (Aug. 2015) pp. 7872-7879.
Safavieh et al. "Emerging loop-mediated isothermal amplification-based microchip and microdevice technologies for nucleic acid detection" ACS biomaterials science & engineering 2.3 (Mar. 2016) pp. 278-294.
Search Report issued in Taiwan Application No. 111101755; Date of Mailing Jun. 19, 2025 (10 pages).

(56) References Cited

OTHER PUBLICATIONS

Search Report issued in Taiwan Application No. 111101759; Date of Mailing Jun. 19, 2025 (9 pages).
Surface area of a cylinder—formula, TSA and CSA [online] [retrieved Jun. 27, 2025] Available from: https://www.cuemath.com/measurement/surface-area-of-cylinder (Year: 2025).
Tian et al. "Development of a fluorescent-intercalating-dye-based reverse transcription loop-mediated isothermal amplification assay for rapid detection of seasonal Japanese B encephalitis outbreaks in pigs" Archives of virology 157.8 (2012) pp. 1481-1488 Abstract Only.
Trantidou et al., "Hydrophilic surface modification of PDMS for droplet microfluids using a simple, quick, and robust method via PVA deposition" Microsyst Nanoeng (Apr. 2017) (9 pages).
Whatman Laboratory Filtration Product Guide [online] GE Healthcare Bio-Sciences Corp [retrieved Jun. 26, 2025] Retrieved from: https://static.fishersci.eu/content/dam/fishersci/en_EU/suppliers/Whatman/Whatman_Lab_Filtration_Product_Guide2.pdf (Year: 2018).
Yin et al. "Synergistically enhanced colorimetric molecular detection using smart cup: a case for instrument-free HPV-associated cancer screening" Theranostics 9.9 (Apr. 2019) 9 pages.
Zhou et al. "A mismatch-tolerant reverse transcription loop-mediated isothermal amplification method and its application on simultaneous detection of all four serotype of dengue viruses" Front Microbiol (May 2019) 13 pages.
Babu et al. "A loop-mediated isothermal amplification (LAMP) assay for the consensus detection of human pathogenic *Campylobacter* species" Journal of microbiological methods 176 (Sep. 2020) pp. 1-6.
Carter et al., "Lyophilized visually readable loop-mediated isothermal reverse transcriptase nucleic acid amplification test for detection Ebola Zaire RNA", J Virol Methods. Jun. 2017 ; 244: 32-38.
Kaarj et al., "Simpler, faster, and sensitive Zika virus assay using smartphone detection of loop-mediated isothermal amplification on paper microfluidic chips" Scientific reports 8.1 (Aug. 2018) 11 pages.
Office Action issued in Korean Patent Application No. 10-2023-7025868; Date of Mailing Nov. 21, 2025 (9 pages).
Office Action issued in Korean Patent Application No. 10-2023-7025878; Date of Mailing Nov. 4, 2025 (10 pages).
Office Action issued in Taiwanese Application No. 111101752; Date of Mailing Oct. 13, 2025 (12 pages).
Thi, V. L. D. et al.; "A colorimetric RT-LAMP assay and LAMP-sequencing for detecting SARS-CoV-2 RNA in clinical samples"; Science Translational Medicine, DOI: 10.1126/scitranslmed.abc7075, 2020, vol. 12, Issue 556.
Wan et al. "Development of a test kit for visual loop-mediated isothermal amplification of *Salmonella* in spiked ready-to-eat fruits and vegetables" Journal of microbiological methods 169 (Feb. 2020) 10 pages.
Wei et al. "Field-deployable, rapid diagnostic testing of saliva for SARS-CoV-2" Scientific reports 11.1 (Mar. 2021) 10 pages.
Wong et al. "Loop-mediated isothermal amplification (LAMP): a versatile technique for detection of micro-organisms" Journal of applied microbiology, 124.3 (Mar. 2018) pp. 626-643.
Agarwal et al "Recent advances in paper-based analytical devices: a pivotal step forward in building Next-generation sensor technology" chapter; In: Inamuddin et al. "Sustainable Polymer Composites and Nanocomposites" Springer Nature (2019) pp. 479-517.
Augustine et al. "Loop-mediated isothermal amplification (LAMP): a rapid, sensitive, specific, and cost-effective Point-of-Care test for Coronaviruses in the context of COVID-19 pandemic" Biology, vol. 9 (2020) p. 182.
Cordone et al. "Proteins in saccharides matrices and the trehalose peculiarity: Biochemical and Biophysical properties" Current Organic Chemistry, vol. 19 (2015) pp. 1-23.
Garcia-Bernalt Diego et al. "Progress in loop-mediated isothermal amplification assay for detection of Schistosoma mansoni DNA: towards a ready-to-use test" Scientific Reports, vol. 9 (2019) p. 14744.
Lo et al. "Molecular-level dengue fever diagnostic devices made out of paper" Lab on a Chip, vol. 13 (2013) pp. 2686-2692.
Wang et al. "On-chip RT-LAMP and colorimetric detection of the prostate cancer 3 biomarker with an integrated thermal and imaging box" Talanta, vol. 208 (2020) p. 120407.

* cited by examiner

Test results with 222 paper showing a color differential between positive (top) and negative (bottom)

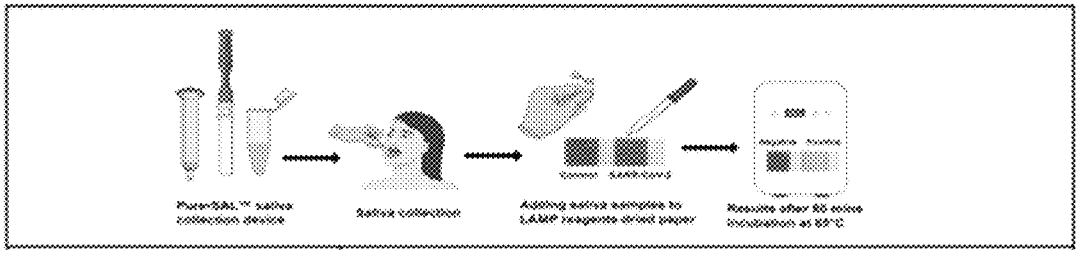
FIG. 19A
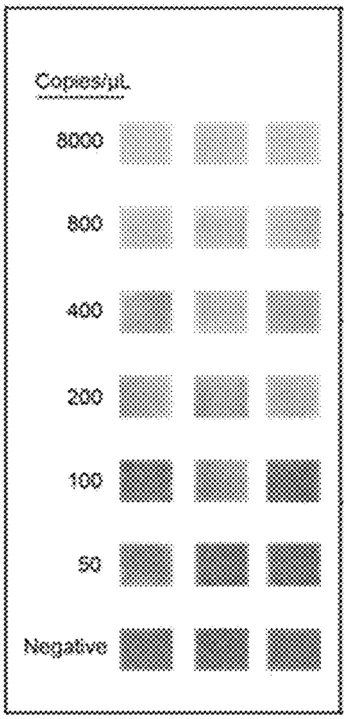
FIG. 19B
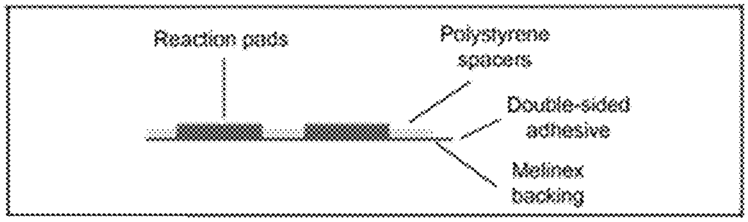
FIG. 19C
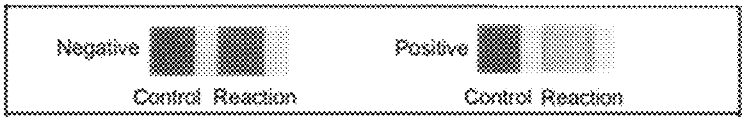
FIG. 19D
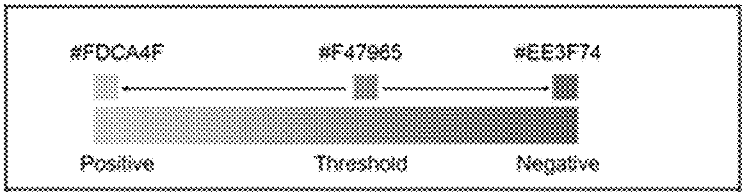
FIG. 19E
True Class
| | | Positive | Negative |
|---|---|---|---|
| Predicted Class | Positive | 16 | 0 |
| | Negative | 5 | 35 |
Sensitivity = 76.2%
Specificity = 100%
Accuracy = 91.1%
False Invalid Rate = 25%
FIG. 19F

Step 1: Compare pad color on the left (control pad) with the color bar. If you think it is a negative color, mark the strip as valid test or else invalid test.

Step 2: Compare pad color on the right (reaction pad) with the color bar. If you think it is a negative color, mark the strip as negative or else positive.

Step 3: Upload the completed survey to this study's Box folder. [Purdue Box link redacted for publication]

Note that corner color changes should not be considered.

As an example, the image bellow would be marked as "valid test" and "positive".

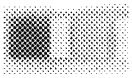

| Strip Number | Control Pad (valid/invalid) | Reaction Pad (positive/negative) |
|---|---|---|
| Example | Valid | Positive |
| 1 | | |
| 2 | | |
| 3 | | |
| 4 | | |
| 5 | | |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |

FIG. 23B

LOOP-MEDIATED ISOTHERMAL AMPLIFICATION (LAMP) ON A SOLID-PHASE MEDIUM

RELATED APPLICATIONS

This application claims the benefit of U.S. Provisional Patent Application Ser. No. 63/138,310 filed Jan. 15, 2021, U.S. Provisional Patent Application Ser. No. 63/138,312 filed Jan. 15, 2021, U.S. Provisional Patent Application Ser. No. 63/138,314 filed Jan. 15, 2021, U.S. Provisional Patent Application Ser. No. 63/138,316 filed Jan. 15, 2021, U.S. Provisional Patent Application Ser. No. 63/138,318 filed Jan. 15, 2021, U.S. Provisional Patent Application Ser. No. 63/138,320 filed Jan. 15, 2021, U.S. Provisional Patent Application Ser. No. 63/138,321 filed Jan. 15, 2021, U.S. Provisional Patent Application Ser. No. 63/138,323 filed Jan. 15, 2021, U.S. Provisional Patent Application Ser. No. 63/138,337 filed Jan. 15, 2021, U.S. Provisional Patent Application Ser. No. 63/138,341 filed Jan. 15, 2021, U.S. Provisional Patent Application Ser. No. 63/148,527 filed Feb. 11, 2021, the entire contents of each of which are incorporated herein by reference.

BACKGROUND

Polymerase chain reaction (PCR) is a molecular biology technique that allows amplification of nucleotides for various analytical purposes. Quantitative PCR (qPCR) is an adaptation of PCR which allows monitoring of the amplification of a targeted nucleotide. Diagnostic qPCR has been applied to detect nucleotides that are indicative of infectious diseases, cancer, and genetic abnormalities. Reverse transcription PCR (RT-PCR) is an adaptation of qPCR which allows detection of a target RNA nucleotides. Because of this ability, RT-PCR is well-suited for detecting virus pathogens. However, RT-PCR uses sizeable equipment which may not be available in certain point of care settings. Additionally, RT-PCR uses trained personnel, significant sample preparation, and time to perform and obtain results.

By contrast, Loop-Mediated Isothermal Amplification (LAMP) is a more simplistic approach to diagnostic identification of target nucleotides. In particular, LAMP is a one-operation nucleic acid amplification method to multiply specific nucleotide sequences. In addition to use of an isothermal heating process, LAMP can use a simple visual output test indicator, such as a color change rather than a more complicated fluorescent indicator used by PCR. Reverse-transcription LAMP (RT-LAMP) can be used like RT-PCR in order to identify target nucleotides from RNA, and as such, can be used in a diagnostic capacity to identify the presence or absence of viral pathogens. Because LAMP is more simplistic, it can be performed with less equipment and sample preparation and therefore is more accessible for use in point of care settings, such as clinics, emergency rooms, and even on a mobile basis.

SUMMARY

The present disclosure is drawn to technologies (e.g., methods, systems, and assemblies) for use in detecting a target nucleotide using Loop-Mediated Isothermal Amplification (LAMP) on a solid phase medium. In some aspects, the target nucleotide can be known to reside in a pathogen of interest. In cases where the pathogen is a virus, the LAMP analysis can be a reverse transcription (RT) RT-LAMP analysis.

In some disclosure embodiments, LAMP reaction assemblies can comprise a substantially hygroscopic agent free LAMP reagent mixture in combination with a solid-phase reaction medium. In one aspect, the solid-phase medium can be hydrophilic, absorbent, and porous.

In one aspect, the solid-phase medium can be substantially free of magnesium-interfering agents. In another aspect, the magnesium-interfering agents can include magnesium-containing compounds and chelating agents that interfere with magnesium.

In another aspect, the solid-phase medium can be a cellulose-based medium. In one aspect, the cellulose-based medium can have a surface area to thickness ratio between about 30 and about 600. In another aspect, the cellulose-based medium can have a pore size of greater than about 1 micron and less than about 100 microns. In one aspect, the solid-phase medium can comprise paper. In another aspect, the solid-phase medium can comprise glass-fiber. In yet another aspect, the solid-phase medium can comprise nylon, polysulfone, polyethersulfone, cellulose acetate, nitrocellulose, or hydrophilic polytetrafluoroethylene (PTFE), or combinations thereof.

In another aspect, the LAMP reaction assembly can further comprise an adhesive substantially free of magnesium-interfering agents and hygroscopic agents. In another aspect, the LAMP reaction assembly can further comprise a spreading layer that is less hydrophilic than the solid-phase reaction medium.

In another disclosure embodiment, methods of manufacturing a LAMP reaction assembly as recited in the preceding can comprise combining the substantially hygroscopic agent free LAMP reagent mixture with the solid-phase reaction medium such that the reagent mixture is held in contact with the solid-phase reaction medium.

In one aspect, the method can comprise controlling discoloration using a non-discoloration additive. In another aspect, the non-discoloration additive can comprise a sugar, a buffer, a blocking agent, or combinations thereof. In another aspect, the non-discoloration additive can comprise a sugar comprising one or more of trehalose, glucose, sucrose, dextran, or combinations thereof. In another aspect, the non-discoloration additive can comprise a blocking agent comprising bovine serum albumin, casein, or combinations thereof.

In another disclosure embodiment, methods of performing a LAMP analysis can comprise providing a LAMP reaction assembly as recited in the preceding, applying a biological sample to the reaction assembly, heating the assembly to a temperature sufficient to initiate LAMP reaction, and maintaining the temperature for a time sufficient to complete the LAMP reaction. In one aspect, the biological sample can be one or more of saliva, mucus, blood, urine, feces, sweat, exhaled breath condensate, or combinations thereof. In another aspect, the biological sample can be saliva. In one aspect, the method can further comprise detecting a viral pathogen. In another aspect, the LAMP analysis can be reverse transcription LAMP (RT-LAMP).

In another disclosure embodiment, a system for a chromatic LAMP analysis can comprise a substantially non-reactive solid phase reaction medium, and a non-interfering reagent mixture. In one aspect, the substantially non-reactive solid phase reaction medium can be hydrophilic, absorbent, and porous. In another aspect, the substantially non-reactive solid phase reaction medium can be substantially free of oxidizing agents, pH-interfering agents, or combinations thereof.

In one aspect, the substantially non-reactive solid phase reaction medium can have a buffering capacity from about 0.01 mM to about 5 mM. In another aspect, the substantially non-reactive solid phase reaction medium has a maximum absorbance wavelength ($\lambda_{max}$) within a testing range when combined with a pH sensitive dye. In another aspect, the substantially non-reactive solid phase reaction medium can comprise cellulose or glass fiber. In another aspect, the system can further comprise an adhesive, a spreading layer, a spacer, a plastic carrier, or combinations thereof. In one aspect, each of the adhesive, spreading layer, spacer, or plastic carrier can be substantially free of oxidizing agents and pH-interfering agents. In another aspect, the non-interfering reagent mixture can further comprise one or more target primers, DNA polymerase, or a re-solubilization agent.

In another disclosure embodiment, methods of maximizing accuracy of a chromatic output signal in a solid phase pH-dependent LAMP analysis can comprise providing a solid phase reaction medium that minimizes non-LAMP reaction produced discoloration, and performing the LAMP analysis on the solid phase reaction medium. In one aspect, the method can comprise controlling non-LAMP produced discoloration from non-LAMP reaction produced protons. In another aspect, the method can comprise controlling non-LAMP reaction produced discoloration using a non-discoloration additive. In one aspect, the non-discoloration additive can comprise a sugar, a buffer, a blocking agent, or combinations thereof. In another aspect, the non-discoloration additive can comprise a sugar comprising one or more of trehalose, glucose, sucrose, dextran, or combinations thereof. In another aspect, the non-discoloration additive can comprise a blocking agent comprising bovine serum albumin, casein, or combinations thereof.

In yet another disclosure embodiment, methods of maximizing a level of detection (LOD) in a LAMP analysis can comprise providing a reaction environment and reagents that minimize non-LAMP reaction products.

In yet another disclosure embodiment, systems for a chromatic LAMP analysis can comprise a combination of a solid phase reaction medium and LAMP reagents which when stored at a selected temperature (e.g., room temperature at about 25° C.) maintain a coloration of the solid phase reaction medium that has a shade that is within 10% of an initial shade of the solid phase medium. In one aspect, the combination can maintain the coloration when stored for longer than one or more of: 30 days, 90 days, 365 days, 2 years, or 5 years. In another aspect, the combination can maintain the coloration when stored at a relative humidity between about 40% and 90%. In another aspect, the selected temperature can be any temperature in a range between about −20° C. and about 37° C.

In yet another disclosure embodiment, methods for manufacturing a chromatic LAMP system as recited in the preceding can comprise combining the non-interfering reagent mixture with a substantially non-reactive solid-phase reaction medium such that the non-interfering reagent mixture is held in contact with the substantially non-reactive solid-phase reaction medium. In one aspect, the method can comprise preparing a solution containing the non-interfering reagent mixture, and coating the reagent mixture onto the substantially non-reactive solid-phase reaction medium. In another aspect, the coating can comprise dropping, spraying, dipping, soaking, or misting the solution onto the substantially non-reactive solid phase reaction medium. In another aspect, the non-interfering reagent mixture can be combined with the substantially non-reactive solid-phase reaction medium using a reel-to-reel (R2R) process.

In yet another disclosure embodiment, a solid phase LAMP reaction medium can comprise a substrate, an adhesive layer disposed on the substrate, a reaction layer disposed on the adhesive layer, or a spreading layer disposed on the reaction layer. In one aspect, the substrate can be an optically transparent material. In another aspect, the adhesive layer can be substantially free of volatile agents. In another aspect, wherein the adhesive layer can be discontinuously disposed on the substrate. In another aspect, the substrate can be an optically clear plastic carrier.

In one aspect, the solid phase LAMP reaction medium can further comprise a testing area. In one aspect, the testing area can be defined by at least two segments of discontinuous adhesive layers. In another aspect, the testing area can be defined by at least three segments of discontinuous adhesive layers. In another aspect, the testing area can be defined by at least four segments of discontinuous adhesive layers.

In one aspect, the solid phase LAMP reaction medium can further comprise at least one segment that is substantially free of reagents. In another aspect, the reaction layer can comprise reagents including one or more target primers, DNA polymerase, or a re-solubilization agent. In another aspect, the reagents can form a composition sufficient to carry out a LAMP reaction. In one aspect the reaction layer can be discontinuous.

In another aspect, the solid phase LAMP reaction medium can further comprise a spreading layer that comprises one or more of glass fiber, nylon, cellulose, polysulfone, polyethersulfone, cellulose acetate, nitrocellulose, polyester, hydrophilic polytetrafluoroethylene (PTFE), or combinations thereof. In one aspect, the spreading layer can be optically transparent.

In another aspect, the solid phase LAMP reaction medium can comprise a spacer material. In one aspect, the spacer material can comprise one or more of glass fiber, nylon, cellulose, polysulfone, polyethersulfone, cellulose acetate, nitrocellulose, polystyrene, polyester, hydrophilic polytetrafluoroethylene (PTFE), or combinations thereof. In another aspect, the spacer material can be oriented in the same plane as the reaction layer and oriented between segments of the reaction layer. In another aspect, the reaction layer can have a surface area to thickness ratio from about 30 to about 600. In another aspect, the reaction layer can have a thickness from about 0.05 mm to about 2 mm. In another aspect, the reaction layer can have a width from about 4 mm to about 12 mm and a length from about 4 mm to about 25 mm. In another aspect, a minimum space between segments of the reaction layer can be between about 1.8 mm and about 2.2 mm.

In another disclosure embodiment, methods of testing for a presence of a viral pathogen can comprise providing a saliva sample from a subject, and dispensing the sample into a test environment having a solid phase reaction medium in combination with a LAMP reagent mixture and a pH sensitive dye. In one aspect, the method can comprise minimizing the amount of volatile agents, hygroscopic agents, and non-pH sensitive agents capable of discoloring the solid phase medium. In another aspect, the method can comprise providing an amount of one or more target primers, DNA polymerase, or a re-solubilization agent sufficient to facilitate a LAMP reaction. In another aspect, the method can comprise providing an amount of reverse transcriptase sufficient to facilitate a reverse transcription LAMP (RT-LAMP) reaction. In another aspect, the method can comprise providing an amount of one or more target primers sufficient to detect the viral pathogen. In another aspect, the method can comprise generating a test result in less than one hour after dispensing the sample into the test environment.

In yet another disclosure embodiment, methods of confirming suitability of a saliva sample for testing with a solid phase LAMP reaction can comprise providing a solid phase reaction medium with at least one test site or test spot and a negative control site. In one aspect, the at least one test site or test spot can include a combination of LAMP reagents and a pH sensitive dye. In another aspect, the negative control site can include a pH sensitive dye and can exclude LAMP reagents. In another aspect, the method can comprise applying the saliva sample to the solid phase reaction medium. In another aspect the method can comprise confirming activation of the pH sensitive dye on the negative control site.

In one aspect, the pH sensitive dye can be at least one of phenol red, phenolphthalein, azolitmin, bromothymol blue, naphtholphthalein, cresol red, or combinations thereof. In another aspect, the LAMP reagents can be substantially free of volatile reagents, pH-affecting reagents, magnesium-containing reagents, or combinations thereof. In another aspect, the LAMP reagents can comprise non-interfering LAMP reagents including DNA polymerase, reverse transcriptase, primers for a target region, or combinations thereof.

In another aspect, the method can further comprise providing the test site or test spot defined by at least two segments of discontinuous adhesive layers. In another aspect, the method can comprise providing the test site or spot defined by at least three segments of discontinuous adhesive layers.

In yet another disclosure embodiment, methods of maximizing accuracy of a positive test result from a solid phase LAMP reaction can comprise providing a solid phase reaction medium with at least three test site or spots, each including a common pH sensitive dye and a combination of LAMP reagents, wherein each site includes a different primer sequence from a target pathogen. In one aspect, the method can comprise initiating a LAMP reaction. In another aspect, the method can comprise confirming a positive test result when at least two of the test site or spots activate the pH sensitive dye and experience a change from a first color to a second color. In another aspect, the method can further comprise providing an amount of reverse transcriptase sufficient to facilitate a reverse transcription LAMP reaction.

In one aspect, the pH sensitive dye can be at least one of phenol red, phenolphthalein, azolitmin, bromothymol blue, naphtholphthalein, cresol red, or combinations thereof. In another aspect, the LAMP reagents can be substantially free of volatile reagents, pH-affecting reagents, magnesium-containing reagents, or combinations thereof.

In another aspect, the target pathogen can comprise a viral pathogen, a bacterial pathogen, a fungal pathogen, or a protozoa pathogen. In one aspect, the target pathogen can comprise a viral pathogen. In one aspect, the viral pathogen can comprise a dsDNA virus, an ssDNA virus, a dsRNA virus, a positive-strand ssRNA virus, a negative-strand ssRNA virus, an ssRNA-RT virus, or a ds-DNA-RT virus. In one aspect, each primer sequence can match a sequence from a viral target comprising H1N1, H2N2, H3N2, H1N1pdm09, or SARS-CoV-2.

In one disclosure embodiment, methods of testing for a presence of a target nucleotide sequence can comprise providing a biological sample, dispensing the sample into a test environment having a solid phase reaction medium in combination with a loop-mediated isothermal amplification (LAMP) reagent mixture and a pH sensitive dye.

In another aspect, the test environment can be substantially free of volatile reagents, pH-affecting reagents, drying agents, or combinations thereof. In one aspect, the method can comprise raising a test environment temperature at a rate of about 0.1° C. per second. In another aspect, the method can comprise providing a heating uniformity in the testing environment that has a variability of less than 1° C. In another aspect, the method can comprise providing a solid phase reaction medium comprising cellulose or glass fiber. In one aspect, the method can comprise providing an amount of reverse transcriptase sufficient to facilitate a reverse transcription LAMP (RT-LAMP) reaction.

In one aspect, the biological sample can be at least one of: saliva, mucus, blood, urine, or feces sweat, exhaled breath condensate, or a combination thereof. In one aspect, the method can comprise collecting the biological sample using one or more of a saliva collection device, a nasal swab, a blood collection device, a urine collection device, a sweat collection device, an exhaled breath condensate collection device, or a stool collection device.

In another aspect, the target nucleotide sequence can be from at least one of a viral pathogen, a bacterial pathogen, a fungal pathogen, or a protozoan pathogen. In one aspect, the target nucleotide sequence can be from a viral pathogen. In one aspect, the viral pathogen can be selected from the group consisting of: Coronoviridae, Orthomyxoviridae, Paramyxoviridae, Picornaviridae, Adenoviridae, and Parvoviridae. In another aspect, the viral pathogen can be selected from the group consisting of: severe acute respiratory syndrome coronavirus (SARS-CoV-1), severe acute respiratory syndrome coronavirus 2 (SARS-CoV-2), Middle East respiratory syndrome (MERS), influenza, and H1N1. In one aspect, the target nucleotide sequence can be from a severe acute respiratory syndrome coronavirus 2 (SARS-CoV-2) pathogen.

In yet another disclosure embodiment, a biological sample testing apparatus can comprise a substrate engaging a solid phase reaction medium in combination with a dehydrated loop-mediated isothermal amplification (LAMP) reagent mixture and a dehydrated pH-sensitive dye, wherein the apparatus provides a degree of test accuracy of at least about 95% after storage for 6 months when stored at room temperature. In one aspect, the apparatus can provide a degree of test accuracy of at least about 95% after storage for 12 months when stored at room temperature. In another aspect, the apparatus can provide a degree of test accuracy of at least about 95% after storage for 2 years when stored at room temperature.

In yet another disclosure embodiment, a biological sample testing system can comprise a substrate engaging a solid phase reaction medium in combination with a dehydrated loop-mediated isothermal amplification (LAMP) reagent mixture and a dehydrated pH-sensitive dye, said housing operable to receive a biological sample. In one aspect, the biological sample testing system can comprise a heater configured to isothermally heat the container to an internal temperature sufficient to initiate and sustain a LAMP reaction between the LAMP reagent mixture. In another aspect, the biological sample testing system can comprise a biological sample for a time used to generate a test result via the pH-sensitive dye.

In one aspect, the substrate can comprise an optically transparent material. In another aspect, the substrate can engage the solid phase reaction medium via an adhesive. In another aspect, the adhesive can be substantially optically transparent. In another aspect, the substrate can comprise a portion of a housing.

In another aspect, the biological sample testing system can comprise an adhesive layer disposed on the substrate, a reaction layer disposed on the adhesive layer, and a spreading layer disposed on the reaction layer. In one aspect, the biological sample testing system can further comprise a spacer layer oriented in the same plane as the reaction layer. In another aspect, the housing can be disposed against the substrate. In another aspect, the housing can be further disposed against the spreading layer. In another aspect, the housing can substantially enclose the substrate, adhesive layer, reaction layer, and spreading layer.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 19A-19F illustrate Schematics and colorimetric characterization of the paper-based device in accordance with an example embodiment;

FIGS. 23A and 23B illustrate colorimetric perception surveys in accordance with an example embodiment.

Figure 1:
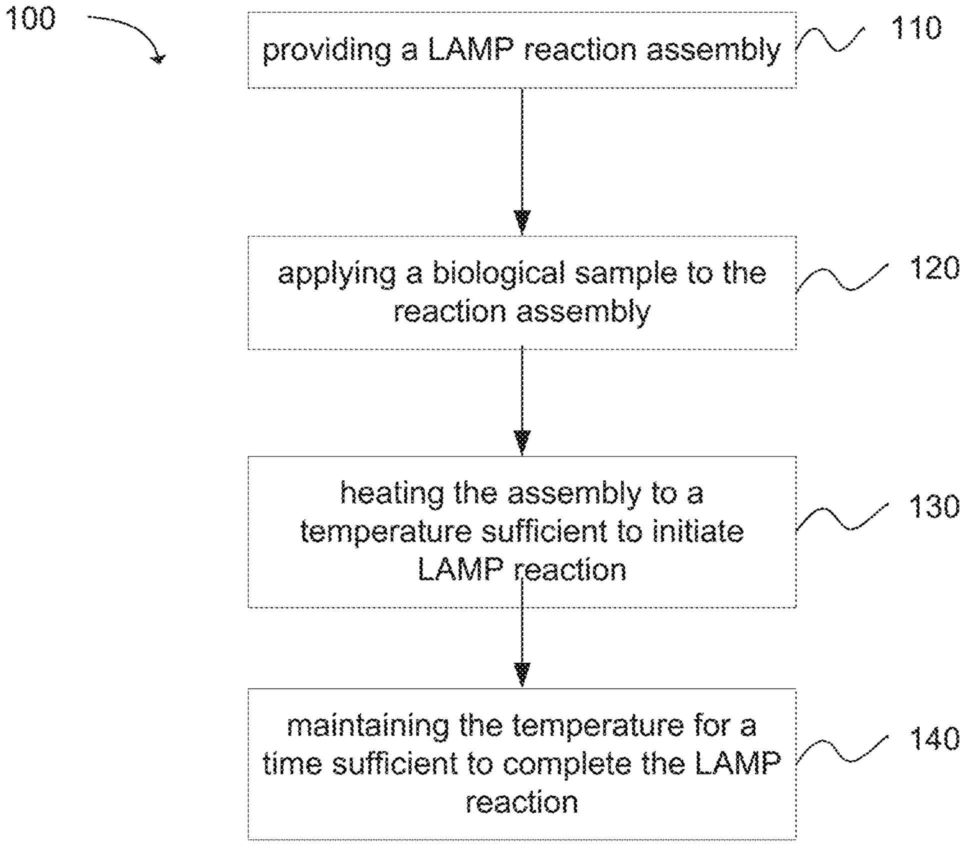
FIG. 1 depicts a method of performing a LAMP analysis in accordance with an example embodiment.

Reference will now be made to the exemplary embodiments illustrated, and specific language will be used herein to describe the same. It will nevertheless be understood that no limitation of the scope of the technology is thereby intended.

DESCRIPTION OF EMBODIMENTS

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein, but are merely representative thereof.

Definitions

It should be noted that as used herein, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other excipients.

As used herein, the term "soluble" is a measure or characteristic of a substance or agent with regards to its ability to dissolve in a given solvent. The solubility of a substance or agent in a particular component of the composition refers to the amount of the substance or agent dissolved to form a visibly clear solution at a specified temperature such as about 25° C. or about 37° C.

As used herein, the term "lipophilic," refers to compounds that are not freely soluble in water. Conversely, the term "hydrophilic" refers to compounds that are soluble in water.

As used herein, a "subject" refers to an animal. In one aspect the animal may be a mammal. In another aspect, the mammal may be a human.

As used herein, "non-liquid" when used to refer to the state of a composition disclosed herein refers to the physical state of the composition as being a semi-solid or solid.

As used herein, "solid" and "semi-solid" refers to the physical state of a composition that supports its own weight at standard temperature and pressure and has adequate viscosity or structure to not freely flow. Semi-solid materials may conform to the shape of a container under applied pressure.

As used herein, a "solid phase medium" refers to a non-liquid medium. In one example, the non-liquid medium can be a material with a porous surface. In another example, the non-liquid medium can be a material with a fibrous surface. In yet another example, the non-liquid medium can be paper.

As used herein, a "solid phase medium," "solid phase base" "solid phase substrate" "solid phase test substrate" "solid phase testing substrate," "solid phase reaction medium" and the like can be used interchangeably herein and refer to a non-liquid medium, device, system, or environment. In some aspects, the non-liquid medium may be substantially free of liquid or entirely free of liquid. In one example, the non-liquid medium can comprise or be a porous material or a material with a porous surface. In another example, the non-liquid medium can comprise or be a fibrous material or a material with a fibrous surface. In yet another example, the non-liquid medium can be a paper.

As used herein, a "non-discoloration additive" refers to an additive that minimizes or prevents a color change in the color of the solid phase medium from an original or starting color to a different color for reasons other than nucleotide amplification from a LAMP reaction taking place thereon or therein. For example, in one embodiment, such a color change can be minimized or reduced as compared to a color change that would take place without the non-discoloration additive present.

As used herein, "non-LAMP reaction produced discoloration" refers to any discoloration (e.g. change in color from an original color to another color) of the solid phase medium which is not the result of a nucleotide amplification from a LAMP reaction. In some examples, non-LAMP reaction produced discoloration can refer to discoloration of the solid phase medium resulting from one or more of: a volatile agent, a magnesium-interfering agent, an oxidizing agent, a pH change resulting from causes other than amplification from a LAMP reaction, drying, or combinations thereof.

As used herein, a "volatile agent" refers to an agent that includes a composition that has a high vapor pressure or a low boiling point. In one example, ammonium sulfate can be a volatile agent because the ammonium ion can volatilize and leave behind a sulfate. In one example, a composition can have a high vapor pressure when the composition is in a gas phase at a temperature of more than about 30° C. In one example, a composition can have a low boiling point when the composition forms is in a gas phase at a temperature of less than about 80° C.

As used herein, a "drying agent" refers to an agent that enhances the drying of the solid-phase medium when compared to the drying of the solid-phase medium without the agent.

As used herein, a "pH-interfering reagent" is a reagent that can affect the pH of a reaction, system, or environment for reasons other than amplification from a LAMP reaction. In one example, the ammonium ion can volatilize from ammonium sulfate, and the sulfate ion can react to form sulfuric acid and affect the pH of the reaction in the absence of amplification from the LAMP reaction.

As used herein, a "non-pH sensitive agent" is a reagent that is substantially unaffected by changes in pH.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in the written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," "maximized," "minimized," and the like refer to a property of a device, component, composition, or activity that is measurably different from other devices, components, compositions or activities that are in a surrounding or adjacent area, that are similarly situated, that are in a single device or composition or in multiple comparable devices or compositions, that are in a group or class, that are in multiple groups or classes, or as compared to the known state of the art.

The term "coupled," as used herein, is defined as directly or indirectly connected in a chemical, mechanical, electrical or nonelectrical manner. Objects described herein as being "adjacent to" each other may be in physical contact with each other, in close proximity to each other, or in the same general region or area as each other, as appropriate for the context in which the phrase is used. "Directly coupled" objects, structures, elements, or features are in contact with one another and may be attached. Further as used in this written description, it is to be understand that when using the term "coupled" support is also afforded for "directly coupled" and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EMBODIMENTS

Many molecular tests for pathogens (e.g., severe acute respiratory syndrome coronavirus 2 (SARS-CoV-2), the virus responsible for COVID-19) can be limited to the laboratory and thus have significant lag times (>24 hours) to provide a result, preventing their adoption in point-of-care settings. Despite several attempts at developing a point-of-care test for SARS-CoV-2, some limitations remain: i) scalability (the demand for testing is in the order of millions per week, but manufacturing new tests at that scale is difficult), ii) sample processing (many tests still use an extraction operation when using saliva), and iii) readability (molecular tests often use fluorescence and thus, a fluorescence reader to report the results).

The current testing methods can be overcome by using a point-of-care test using paper-based devices and reverse-transcription loop-mediated isothermal amplification (RT-LAMP) that report a color change in the presence of a pathogen (e.g., SARS-CoV-2) within 60 minutes using diluted saliva (e.g., 5% v/v in water) as the sample. RT-LAMP is a nucleic acid amplification technique conducted at a constant temperature with adequate diagnostic performance especially during the acute phase of infection. Since RT-LAMP can be conducted at a constant temperature, expensive thermal cycling equipment is not used. Additionally, existing colorimetric reporters for LAMP products do not use fluorescence readers. Consequently, this test is suitable for use in point-of-care settings and is amenable to rapid development and scale-up, making it appropriate for use in public health emergencies.

RT-LAMP can be implemented on microfluidic paper-based analytical devices (μPADs) to detect various pathogens (e.g., SARS-CoV-2) where image analysis can be performed using a portable electronic device to distinguish between positive and negative responses. In one example, a high-contrast RT-LAMP reaction on paper can provide a color change that can be visible to the naked eye. In addition, instead of using wax-printing—which would have precise alignment of printed areas and dispensing of reagents—polystyrene spacers can be used for preventing crosstalk between samples. The polystyrene spacers can be amenable to roll-to-roll fabrication for scale up of production.

Nucleic-acid-based COVID-19 diagnosis methods use pre-processing to provide results. As disclosed herein, on-paper colorimetric detection of SARS-CoV-2 can be performed with minimal pre-processing. The device can have a sensitivity and specificity that can detect SARS-CoV-2 on paper without pre-amplification. Other assays conducted in solution may not be as scalable during manufacturing as paper-based assays. Additionally, the assay disclosed herein uses a dilution operation that can be completed in seconds, whereas other assays use various operations such as treatment with protease, heat-inactivation, and/or RNA extraction to detect SARS-CoV-2 (operations completed in at least 10 minutes and using additional equipment).

Material Assembly for LAMP Reaction on a Solid-Phase Medium

Conducting a LAMP reaction on a solid-phase medium can be difficult because of the involved performance demands. For example, in order to maximize test accuracy, the solid-phase medium should support the LAMP reaction without interference with it or the LAMP reaction indicator. At a high level, the solid-phase medium is hydrated with a biological sample to allow the LAMP reaction to proceed and thereafter the results are read. However, various reagents can interfere with the LAMP reaction or the subsequent reading of the results. In order to minimize error, care can be taken to minimize or avoid possible challenges that may arise with respect to providing a biological sample, hydrating solid phase medium with a sample, integrating LAMP reagents into the solid phase medium, carrying out the LAMP analysis, and obtaining a clear test output signal that can be interpreted without difficulty.

With the above-described background in mind, in one disclosure embodiment, a loop-mediated isothermal amplification (LAMP) reaction assembly can comprise a substantially hygroscopic agent free LAMP reagent mixture in combination with a solid-phase reaction medium. The LAMP reagent mixture, when substantially free of hygroscopic agents, can minimize or avoid difficulties occurring during drying of the solid-phase reaction medium. When hygroscopic agents are used, they or the solid-phase reaction medium may not dry entirely, or may rehydrate to a degree upon storage and may interfere with the original color of the solid-phase reaction medium which can skew the test results from the LAMP process.

In one example, a hygroscopic agent can be an agent that absorbs more than about 10 wt % when between about 40% and about 90% relative humidity (RH) at 25° C. In one aspect, a hygroscopic agent can comprise but is not limited to, one or more of glycerol, ethanol, methanol, calcium chloride, potassium chloride, calcium sulfate, the like, or combinations thereof. In some examples, a LAMP reaction that contains a hygroscopic agent, such as glycerol can contribute to the instability of reagents in the solid-phase medium because the hygroscopic agent can attract water. Therefore, an excessive amount of hygroscopic agents in the solid-phase reaction medium should be avoided.

Furthermore, in another aspect, the substantially hygroscopic agent free LAMP reagent mixture can comprise one or more of DNA polymerase, reverse transcriptase, target primers, or combinations thereof. DNA polymerase can be included when the LAMP reaction is either a LAMP reaction or a reverse transcription LAMP (RT-LAMP) reaction. Furthermore, when the LAMP reaction is an RT-LAMP reaction, the substantially hygroscopic agent free LAMP reagent can further include reverse transcriptase used to reverse transcribe RNA to cDNA.

In one aspect, the solid-phase reaction medium can be substantially free of magnesium-interfering agents. Magnesium can interfere with the LAMP reaction in a few ways. First, magnesium can be a cofactor for DNA polymerase and should be tightly monitored within a target concentration range to allow the DNA polymerase to facilitate the LAMP reaction. Second, when a magnesium-sensitive indicator is used for the LAMP reaction, then magnesium interfering agents can invalidate the results of the LAMP reaction or complicate the analysis of the results.

As such, in another aspect, the magnesium-interfering agents can include magnesium-containing compounds and chelating agents that interfere with magnesium. In one aspect, the magnesium-interfering agents can be substantially free of magnesium including, but not limited to: $Mg^{2+}$, $Mg^{1+}$, magnesium carbonate, magnesium chloride, magnesium citrate, magnesium hydroxide, magnesium oxide, magnesium sulfate, magnesium sulfate heptahydrate, the like, or combinations thereof. Because some solid-phase reaction medium might have some buffer capacity, residual ions, or chelating agents that can interfere with magnesium, the concentration of magnesium—a cofactor for BST enzymes (e.g., DNA polymerase)—can be affected and interfere with the LAMP reaction. Consequently, the concentration of magnesium should be controlled within a target magnesium range to facilitate the LAMP reaction. In one aspect, the composition can contain less than one or more of: 1.0 wt %, 0.5 wt %, 0.1 wt %, or 0.01 wt % of magnesium.

The solid-phase reaction medium can have several characteristics to facilitate the LAMP reaction. In one aspect, the solid-phase reaction medium can be hydrophilic, absorbent, porous, and inert. The solid-phase reaction medium can be hydrophilic when the contact angle between the surface and edge of a droplet is less than about 90 degrees. The solid-phase reaction medium can be absorbent as measured by the degree to which paper can take up an amount of liquid. The solid-phase reaction medium can be porous when the solid-phase reaction medium has a pore size of greater then at least 1 micron and less than or equal to one or more of about 100 microns, about 75 microns, about 50 microns, about 25 microns, about 10 microns, about 5 microns, or about 1 micron. The solid-phase reaction medium can be inert when the medium does not interfere with the LAMP reaction. The solid-phase reaction medium can also be inert when the medium does not interfere with the indication resulting from the LAMP reaction.

There are various materials that the solid-phase reaction medium can comprise or include. In one aspect, the solid-phase reaction medium can comprise one or more of nylon, polysulfone, polyethersulfone, cellulose acetate, nitrocellulose, hydrophilic polytetrafluoroethylene (PTFE), the like, or combinations thereof. In another aspect, the solid-phase reaction medium can be a cellulose-based medium, such as Grade 1 chromatography paper, Grade 222 chromatography paper, the like, or combinations thereof.

In addition to the type of material for the solid-phase reaction medium, the solid-phase reaction medium can have several physical properties that can accommodate or enhance the LAMP reaction and avoid interference with the indication or signal output resulting from the LAMP reaction. In one aspect, the solid-phase reaction medium can have a surface area to thickness ratio between about 30 and about 600. In another aspect, the solid-phase reaction medium can have a surface area to thickness ratio between about 60 and about 400. In one aspect, the solid-phase reaction medium can have a surface area to thickness ratio between about 100 and about 200. In another aspect, the solid-phase reaction medium can be a cellulose-based medium that can have a surface area to thickness ratio between about 30 and about 600. In one aspect, the cellulose-based medium can have a pore size of greater than at least 1 micron and less than or equal to one or more of about 100 microns, about 75 microns, about 50 microns, about 25 microns, about 10 microns, about 5 microns, or about 1 micron.

The thickness of the solid-phase reaction medium can contribute to the total reaction time for the LAMP reaction, the flow rate through the solid-phase reaction medium, the color contrast when a colorimetric indicator is used, the uniformity of the colorimetric results, the concentration of the reagents in the solid-phase reaction medium, and the like.

In one aspect, the solid-phase reaction medium can comprise grade 222 chromatography paper, which provides increased uniformity relative to the uniformity of grade 1 chromatography paper because grade 222 chromatography paper is thicker than Grade 1 chromatography paper. Consequently, grade 222 chromatography paper can concentrate reagents in a smaller surface area compared to grade 1 chromatography paper. In one aspect, the chromatography paper can be grade 222 having a surface area of about 5 mm by about 5 mm to provide desired surface area to thickness ratio. In one example, the grade 1 chromatography paper can have cross sectional dimensions of 20 mm in length and 5 mm in width with a 0.18 mm thickness to provide a surface area to thickness ratio of about 555. In another example, grade 222 chromatography paper can have cross sectional dimensions of 5 mm in length and 5 mm in width with a 0.83 mm thickness to provide a surface area to thickness ratio of about 30. As such, this example illustrates that a surface area to thickness ratio of about 30 (e.g., for the grade 222 chromatography paper) can provide increased uniformity compared to a surface area to thickness ratio of about 555 (e.g., for grade 1 chromatography paper).

Besides the materials disclosed herein, the solid-phase reaction medium can comprise one or more of paper or glass-fiber. In one example, the paper can comprise one or more of alpha cellulose, beta cellulose, gamma cellulose, the like, or combinations thereof. In another example, the glass-fiber can comprise one or more of A-glass, E-glass, S-glass, R-glass, C-glass, T-glass, D-glass, M-glass, ECR glass, the like, or combinations thereof.

In some examples, the reaction assembly can include an adhesive. For example, the adhesive can be used to adhere various segments of the solid-phase reaction medium to each other. In one example, the reaction assembly can further comprise an adhesive substantially free of magnesium-interfering agents, hygroscopic agents, or combinations thereof. The adhesive can be substantially free of magnesium-interfering agents to avoid interference between magnesium and DNA polymerase and to avoid complications in reading the LAMP results when using magnesium-based indicators.

In some examples, the reaction assembly can also include a spreading layer. The spreading layer can facilitate a uniform spreading of a biological sample throughout the different sections of the solid-phase reaction medium. In another example, the spreading layer can be less hydrophilic than the solid-phase reaction medium. Having a spreading layer that is less hydrophilic than the solid-phase reaction medium can facilitate the uniform spreading of the biological sample because the biological sample will diffuse away from the less hydrophilic spreading layer towards the more hydrophilic solid-phase reaction medium.

The configuration of the reagent mixture with respect to the solid-phase reaction medium can affect the LAMP reaction. In one embodiment, a method of manufacturing a LAMP reaction assembly as recited herein can comprise combining the substantially hygroscopic agent free LAMP reagent mixture with the solid-phase reaction medium such that the reagent mixture is held in contact with the solid-phase reaction medium. In one example, the reagent mixture can be held in direct contact with the solid-phase reaction medium. In another example, the reagent mixture can be held in indirect contact with the solid-phase reaction medium. When the reagent mixture is held in indirect contact with the solid-phase reaction medium, an intervening material (e.g., an antioxidant) can enhance the LAMP reaction.

In some cases, the color of the solid-phase reaction medium can be affected by agents that do not result from the LAMP reaction. For example, volatile agents, such as ammonium sulfate, can form a sulfate ion that can react to form sulfuric acid. When a pH-based indicator is used to read the results of the LAMP reaction, then these non-LAMP reactions can prevent a correct reading of the results or can further complicate interpretation of the results.

In one aspect, the method can comprise controlling discoloration using a non-discoloration additive. The non-discoloration additive can comprise a sugar, a buffer, a blocking agent, the like, or combinations thereof. In one example, the sugar can comprise one or more of trehalose, glucose, sucrose, dextran, the like, or combinations thereof.

In another example, the blocking agent can comprise bovine serum albumin, casein, the like, or combinations thereof.

The sugar can prevent the impact of the non-LAMP reagent pH changes. The buffer can prevent interference with the LAMP reaction or the results of the LAMP reaction by preventing the impact of pH changes that arise from factors other than the LAMP reaction. The blocking agent can prevent the impact from factors other than the LAMP reaction by blocking the actions of various enzymes, such as RNase or DNase, on the nucleic acids to be analyzed (e.g., RNA from a virus or DNA from a pathogen).

In another embodiment, as depicted in FIG. 1, a method 100 of performing a LAMP analysis can comprise providing a LAMP reaction assembly as recited in this disclosure, as shown in block 110. The method can further comprise applying a biological sample to the reaction assembly, as shown in block 120. The method can further comprise heating the assembly to a temperature sufficient to initiate LAMP reaction, as shown in block 130. The method can further comprise maintaining the temperature for a time sufficient to complete the LAMP reaction, as shown in block 140.

In one aspect, the biological sample can be one or more of saliva, mucus, blood, urine, feces, sweat, exhaled breath condensate, or combinations thereof. In another aspect, the biological sample can be saliva. In another aspect, the method can further comprise detecting a viral pathogen. In another aspect, the LAMP analysis can be reverse transcription LAMP (RT-LAMP).

In another aspect, the temperature sufficient to initiate a LAMP reaction can be in a temperature range of from about 50° C. to about 60° C. In another aspect, the temperature sufficient to initiate a LAMP reaction can be in a temperature range of from about 60° C. to about 70° C. In another example, the isothermal temperature can be a temperature within a range that differs by less than 5° C. In another aspect, the temperature can be maintained the temperature sufficient to complete the LAMP reaction for more than one or more of: 15 minutes, 30 minutes, 45 minutes, 60 minutes, 75 minutes, 90 minutes, 105 minutes, or 120 minutes. In another aspect, the temperature can be maintained the temperature sufficient to complete the LAMP reaction for less than one or more of: 15 minutes, 30 minutes, 45 minutes, 60 minutes, 75 minutes, 90 minutes, 105 minutes, or 120 minutes.

The LAMP reaction assembly can be manufactured to enhance its uniformity, its shelf-life or storage life, and its test validity. In one aspect, the LAMP reaction assembly can be manufactured using one or more of: slitting (splitting rolls into thinner rolls), singulation (individual pieces cut by guillotine, rotary die, or laser), reagent coating (reagents dipped, sprayed or dispensed and dried), card lamination (plastic backing added to reels), the like, or combinations thereof. In one example, the LAMP reaction assembly can be manufactured using one or more of: splitting rolls into thinner rolls; individual pieces cut by guillotine or rotary die; reagent coating using reagent dipping, card lamination using plastic backing added to reels, the like, or combinations thereof.

Materials for pH-Based LAMP Analysis on a Solid-Phase Medium

Conducting a LAMP reaction on a solid-phase reaction medium can be difficult when hygroscopic agents and magnesium-interfering agents are present. However, there are other factors that can interfere with the output and interpretation of the LAMP reaction results. When a pH-based indicator is involved, then the reagent mixture should be substantially free of interfering reagents. In some examples, the interfering reagents can include oxidizing agents and pH interfering agents.

In one embodiment, a system for a chromatic loop-mediated isothermal amplification (LAMP) analysis can comprise a substantially non-reactive solid phase reaction medium, and a non-interfering reagent mixture. In one aspect, the substantially non-reactive solid phase reaction medium can be substantially free of oxidizing agents and pH-interfering agents. In one aspect, the non-interfering reagent mixture can comprise one or more target primers, DNA polymerase, a re-solubilization agent, or combinations thereof.

The oxidizing agents can interfere with the LAMP reaction. Therefore, oxidizing agents should not be included in the substantially non-reactive solid phase reaction medium. In one aspect, an oxidizing agent can include, but is not limited to, one or more of: $O_2$, $O_3$, $H_2O_2$, $F_2$, $Cl_2$, halogens, $HNO_3$, nitrates, $H_2SO_4$, $H_2S_2O_8$, $H_2SO_5$, hypochlorite, chlorite, chlorate, perchlorate, chromium compounds, permanganate, sodium perborate, nitrous oxide, $NO_2$, $N_2O_4$, $KNO_3$, $NaBiO_3$, cerium compounds, lead dioxide, the like, or combinations thereof.

In some cases, merely avoiding oxidation agents may not be sufficient to facilitate the LAMP reaction. In such cases, additional agents can be included to prevent undesirable oxidation. In one aspect, the non-reactive solid phase reaction medium can include one or more of: oxygen absorbers, desiccants, the like, or combinations thereof to prevent oxidation of the non-reactive solid phase reaction medium. In another aspect, to prevent oxidation of a non-reactive solid phase reaction medium that comprises cellulose, the cellulose can be pretreated by heat cycling the cellulose to saturate the oxidation sites. In another example, an antioxidant can be added to prevent oxidation. In another aspect, a dye indicator (e.g., phenol red) can have antioxidant effects. In one aspect, the substantially non-reactive solid phase reaction medium can contain less than one or more of: 1.0 wt %, 0.5 wt %, 0.1 wt %, or 0.01 wt % of the oxidizing agents.

Besides oxidation agents, pH-interfering agents can prevent a proper interpretation of the results of the LAMP reaction or further complicate the signal output of the LAMP reaction. In one aspect, a pH-interfering agent can include, but is not limited to, one or more of: volatile reagents, pH-affecting reagents, magnesium-containing reagents, or combinations thereof.

When pH-affecting reagents are included, the resulting change in pH can complicate the analysis of the pH-based results from the LAMP reaction. In some cases, the inclusion of the pH-affecting reagents can be compensated for, and the analysis can be adjusted to allow adequate test interpretation. However, in other cases, the pH-affecting reagents can introduce unclarity into the interpretation of the pH-based results.

In one example, the substantially non-reactive solid phase reaction medium can be substantially free of pH-affecting reagents. In one aspect, the pH-affecting reagents can include acids, bases, or combinations thereof that can interfere with a pH-sensitive signal. In one aspect, the substantially non-reactive solid phase reaction medium can contain less than one or more of: 1.0 wt %, 0.5 wt %, 0.1 wt %, or 0.01 wt % of the pH-affecting reagents.

When volatile reagents are included on the non-reactive solid phase reaction medium, the volatile component can volatize and leave behind a component that can interfere with the pH-sensitive output signal or leave behind a component that can further react to interfere with the pH-sensitive output signal. In one example, ammonium carbonate can form an ammonium ion that volatizes and a carbonate ion that reacts to form carbonic acid. The carbonic acid can interfere with the pH-sensitive output signal by lowering the pH in the absence of a positive result (e.g., presence of a target pathogen and LAMP-induced amplification) from the LAMP reaction. As such, in one example, the non-reactive solid phase medium can be substantially free of volatile agents as defined herein.

When magnesium-containing reagents are included on the non-reactive solid phase reaction medium, the magnesium-containing reagents, when not tightly monitored, can interfere with the operation of the DNA polymerase. Therefore, in one example, the substantially non-reactive solid phase reaction medium can be substantially free of magnesium reagents as otherwise disclosed herein.

The substantially non-reactive solid phase medium can be comprised of various materials. In one aspect, the substantially non-reactive solid phase reaction medium can comprise glass fiber, nylon, cellulose, polysulfone, polyethersulfone, cellulose acetate, nitrocellulose, hydrophilic PTFE, the like, or combinations thereof. In another aspect, the substantially non-reactive solid phase reaction medium can be hydrophilic, absorbent, inert, and porous as disclosed herein.

The buffering capacity of the non-reactive solid phase medium can affect the LAMP reaction. For example, a strong buffer can prevent the changes in pH that are to be detected from the LAMP reaction. However, a weak buffer can lead to large swings in pH even in the absence of LAMP-induced amplification. In one aspect, the substantially non-reactive solid phase reaction medium can have a buffering capacity from about 0.01 mM to about 5 mM. In one example, a heat inactivated virus can be spiked into bio-banked saliva at a limit-of-detection on the order of about 500 copies per 25 μl of sample volume. However, the buffering capacity and pH of bio-banked saliva can differ from freshly collected saliva. Therefore, the limit of detection (LOD) of freshly collected saliva can be adjusted based on the buffering capacity differences and pH differences between bio-banked saliva and freshly collected saliva.

In some examples, the pH-sensitive output signal from the non-reactive solid-phase reaction medium can be interpreted by a technician without specialized instrumentation. However, a colorimetric reader can provide an additional level of precision and accuracy. For example, in one example, the substantially non-reactive solid phase reaction medium can have a maximum absorbance wavelength ($\lambda_{max}$) within a testing range when combined with a pH sensitive dye. In one example, when the pH sensitive dye is phenol red, the $\lambda_{max}$ can be within a testing range of about 443 nm to about 570 nm. Therefore, when the pH-sensitive dye is phenol red and the maximum absorbance wavelength is within a testing range, a technician can use a colorimetric reader to detect a positive or negative result.

In some aspects, the system can further comprise components in addition to the non-reactive solid-phase reaction medium. In one aspect, the system can further comprise an adhesive, a spreading layer, a spacer, a plastic carrier, or combinations thereof. In one aspect, each of the adhesive, spreading layer, spacer, and plastic carrier can be substantially free of oxidizing agents and pH-interfering agents as disclosed herein.

Figure 2:
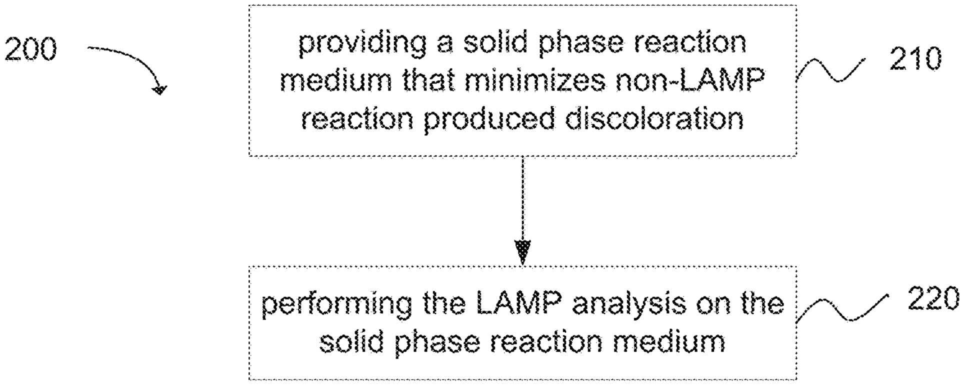
FIG. 2 depicts a method of maximizing accuracy of a chromatic output signal in a solid phase pH-dependent loop-mediated isothermal amplification (LAMP) analysis in accordance with an example embodiment.

In another embodiment, as depicted in FIG. 2, a method 200 of maximizing accuracy of a chromatic output signal in a solid phase pH-dependent loop-mediated isothermal amplification (LAMP) analysis can comprise: providing a solid phase reaction medium that minimizes non-LAMP reaction produced discoloration, as shown in block 210, and performing the LAMP analysis on the solid phase reaction medium, as shown in block 220.

In one aspect, the method can further comprise controlling non-LAMP produced discoloration from non-LAMP reaction produced protons. In another aspect, the method can further comprise controlling non-LAMP reaction produced discoloration using a non-discoloration additive.

A non-discoloration additive can prevent undesirable changes in the colorimetric response due to non-LAMP amplification. In one aspect, the non-discoloration additive can comprise a sugar, a buffer, a blocking agent, the like, or combinations thereof.

In one example, the sugar can comprise one or more of trehalose, glucose, sucrose, dextran, the like, or combinations thereof. In one aspect, the concentration of the sugar can be from about 0.01 mM to about 1 M when used on the solid-phase medium. In another example, the concentration of the sugar can be from about 10 mM to about 500 mM when used on the solid-phase medium. In yet another example, the concentration of the sugar can be from about 200 mM to about 400 mM when used on the solid-phase medium.

In another example, a buffer can include one or more of phosphate-buffered saline (PBS), Dulbecco's PBS, Alsever's solution, Tris-buffered saline (TB S), water, HEPES, BICINE, balanced salt solutions (BSS), such as Hank's BSS, Earle's BSS, Grey's BSS, Puck's BSS, Simm's BSS, Tyrode's BSS, BSS Plus, Ringer's lactate solution, normal saline (i.e. 0.9% saline), ½ normal saline, the like, or combinations thereof. In one aspect, the concentration of the buffer can be from about 10 μM to about 20 mM when used on the solid-phase medium. In another example, the concentration of the buffer can be from about 100 μM to about 10 mM when used on the solid-phase medium. In yet another example, the concentration of the buffer can be from about 100 μM to about 500 μM when used on the solid-phase medium.

In another example, a blocking agent can include one or more of bovine serum albumin, casein, or combinations thereof. In one aspect, the concentration of the blocking agent can be from about 0.01 wt % to about 5 wt % when used on the solid-phase medium. In another example, the concentration of the blocking agent can be from about 0.01 wt % to about 1 wt % when used on the solid-phase medium. In yet another example, the concentration of the blocking agent can be from about 0.02 wt % to about 0.06 wt % when used on the solid-phase medium.

In another embodiment, a method of maximizing a level of detection (LOD) in a loop-mediated isothermal amplification (LAMP) analysis can comprise providing a reaction environment and reagents that minimize non-LAMP reaction products. In some examples, the reaction environment can be substantially free of one or more of oxidizing agents, pH-interfering agents, hygroscopic reagents, magnesium-interfering reagents, the like, or combinations thereof.

In another embodiment, a system for a chromatic loop-mediated isothermal amplification (LAMP) analysis can comprise a combination of a solid phase reaction medium and LAMP reagents which when stored at 25° C. can maintain a coloration of the solid phase reaction medium that is within 10% of an initial shade of the solid phase medium. In one aspect, the combination of the solid phase medium and the LAMP reagents can maintain the coloration when stored for longer than one or more of: 30 days, 90 days, 365 days, 2 years, 3 years, or 5 years. In another aspect, the combination of the solid phase medium and the LAMP reagents can maintain the coloration when stored at a relative humidity between about 40% and 90%.

In another embodiment, a method for manufacturing a chromatic LAMP system can comprise combining the non-interfering reagent mixture with a substantially non-reactive solid-phase reaction medium such that the non-interfering reagent mixture is held in contact with the substantially non-reactive solid-phase reaction medium.

In one example, the non-interfering reagent mixture can be held in direct contact with the solid-phase reaction medium. In another example, the non-interfering reagent mixture can be held in indirect contact with the solid-phase reaction medium. When the non-interfering reagent mixture is held in indirect contact with the solid-phase reaction medium, an intervening material (e.g., an antioxidant) can enhance the LAMP reaction.

In one aspect, the method can include: preparing a solution containing the non-interfering reagent mixture, and coating the reagent mixture onto the substantially non-reactive solid-phase reaction medium. In another aspect, the coating can comprise dropping, spraying, dipping, soaking, or misting the solution onto the substantially non-reactive solid phase reaction medium.

In some cases, the manufacturing process can affect the shelf-life stability or uniformity of the system for the LAMP analysis. In one example, the non-interfering reagent mixture can be combined with the substantially non-reactive solid-phase reaction medium using a reel-to-reel (R2R) process.

Multiplexing Selected Targets to Test for Pathogens Using LAMP on a Solid-Phase Medium When detecting a pathogen using LAMP on a solid-phase medium, there are various ways of multiplexing LAMP. First, the process can be multiplexed by including multiple controls on the same solid-phase medium. For example, the test validity can be verified using a positive control. For example, the LAMP reaction can test a saliva sample for a saliva DNA or RNA biomarker to verify that the LAMP reaction is functioning as expected. In another example, the test validity can be verified using a negative control. For example, the LAMP reaction can test a saliva sample that does not include the pathogen.

A second way of multiplexing LAMP can be by including primers that target multiple, different pathogens on the same solid-phase medium. For example, the test validity can be verified by testing for a viral pathogen and a bacterial pathogen on the same solid-phase medium to further characterize the biological sample.

A third way of multiplexing LAMP can be by testing for the same pathogen using different target primers. In one example, a first section of the solid-phase medium can test using a primer set for a first protein of a viral pathogen, a second section of the solid-phase medium can test using a second primer set for a second protein of the viral pathogen, and a third section of the solid phase medium can test using a third primer set for a third protein of the viral pathogen. Each of the primers can be targeted to distinct regions of the genome of the viral pathogen to eliminate false negatives and false positives.

Figure 3A:
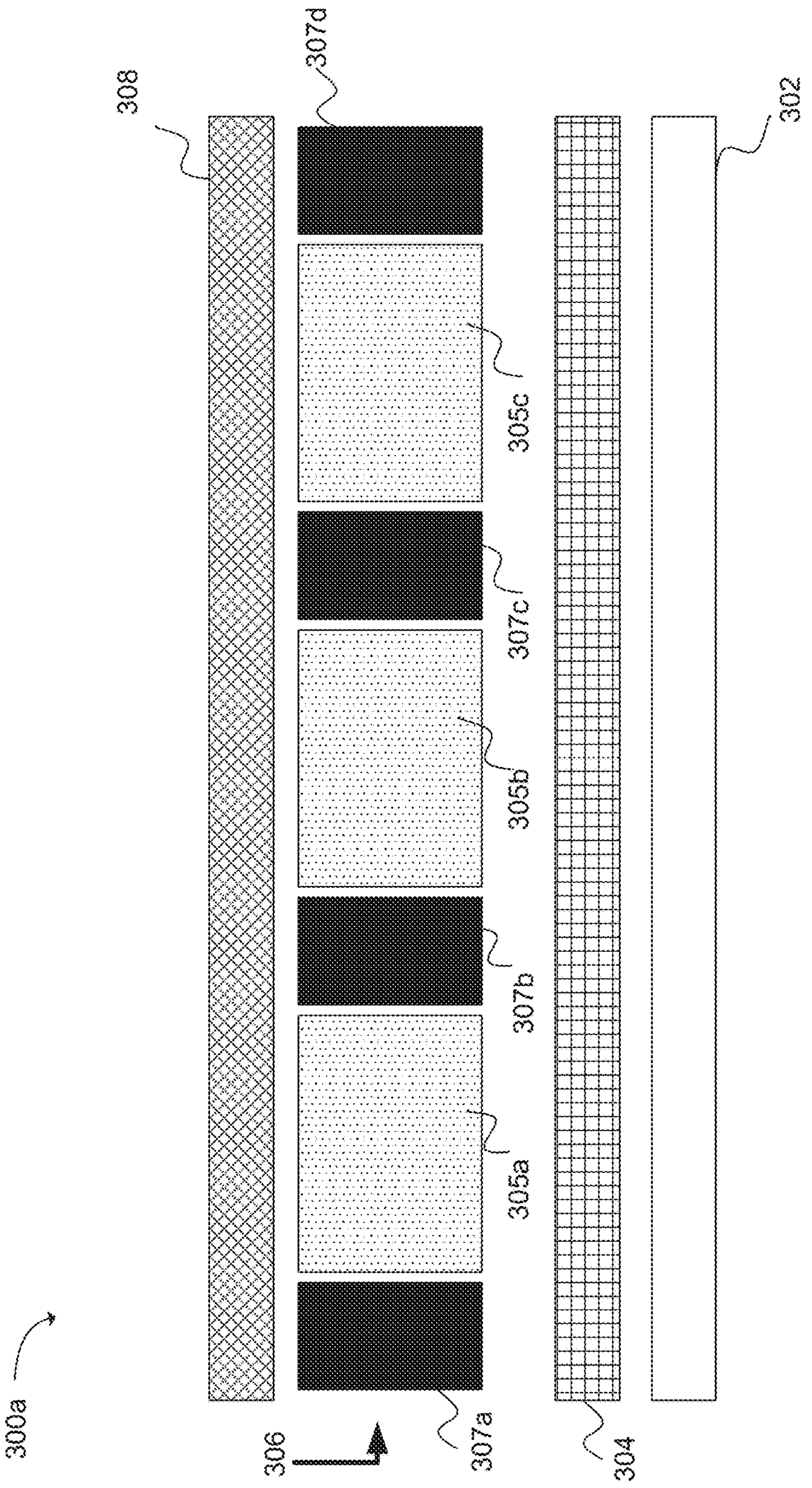
FIG. 3*a* illustrates a solid phase LAMP reaction medium with three testing sections in accordance with an example embodiment.

LAMP can be multiplexed by including various components on the solid phase LAMP reaction medium. In one embodiment, as illustrated in FIG. 3*a*, a solid phase reaction medium 300*a* for conducting a LAMP analysis can comprise a substrate 302, an adhesive layer 304 disposed on the substrate 302, a reaction layer 306 including test spots or reaction locations or segments 305*a*, 305*b*, 305*c* and spacers 307*a*, 307*b*, 307*c* disposed on the adhesive layer 304, and a spreading layer 308 disposed on the reaction layer 306. In one aspect, the test spots 305*a*, 305*b*, and 305*c* can include or otherwise hold reagents including one or more target primers, DNA polymerase, a re-solubilization agent, etc. In one aspect, the reagents can form a composition sufficient to carry out a LAMP reaction.

The spatially discontinuous reaction layer 306 can allow multiplexing of multiple controls or multiple pathogens. For example, test spot 305*a* can be a positive control (e.g., test for a known saliva DNA or RNA biomarker), test spot 305*b* can be negative control (e.g., test for a colorimetric result without including all of the reagents used for the LAMP reaction), and test spot or reaction segment 305*c* can test for the target pathogen.

The spatially discontinuous test spots or reaction locations 305*a*, 305*b*, and 305*c* can also allow for multiplexed detection of multiple pathogens. For example, test spot 305*a* can test for influenza, test spot 305*b* can test for a bacterial infection, and test spot 305*c* can test for a fungal infection.

The dimensions of the reaction locations or segments 305*a*-305*c* can impact the multiplexing potential. In one aspect, the reaction segments 305*a*-305*c* can have a thickness from about 0.05 mm to about 2 mm. In another aspect, the reaction segments 305*a*-305*c* can have a width from about 4 mm to about 12 mm and a length from about 4 mm to about 25 mm. In one example, the reaction locations 305*a*-305*c* can be spatially discontinuous. In another example, the reaction segments 305*a*-305*c* can have a surface area to thickness ratio from about 30 to about 600.

In one example, the solid-phase reaction medium 300*a* can be configured to receive a biological fluid that can flow transversely across the spreading layer 308 and that can migrate vertically down into the test spots 305*a*-305*c* of the reaction layer 306. The test spots 305*a*-305*c* can contain all the components used for a RT-LAMP or LAMP reaction to occur. In one example, the test spots 305*a*-305*c* can contain a re-solubilization agent (e.g., a surfactant), enzymes (e.g., DNA polymerase, reverse transcriptase, DNase inhibitors, or RNase inhibitors), stabilizers (e.g., blocking agents such as BSA or casein), a colorimetric indicator (e.g., a magnesium colorimetric indicator, a pH colorimetric indicator, or a DNA intercalating colorimetric indicator), and a buffer (e.g., 20 mM Tris).

The solid-phase reaction medium 300*a* can be configured to receive an agent that can speed up the reaction, increase sensitivity, or a combination thereof. In one example, BSA can speed up the reaction and increase sensitivity. However, the inclusion of BSA can also introduce pH variations that can interfere with the readability of the results. Therefore, in some examples, the stabilizer can be casein, polysorbate 20, the like, or a combination thereof.

The reaction segments or spots (e.g. test spots) 305*a*-305*c* can comprise any suitable material disclosed herein. In one example, the reaction segments 305*a*-305*c* can comprise one or more of glass fiber, nylon, cellulose, polysulfone, polyethersulfone, cellulose acetate, nitrocellulose, hydrophilic PTFE, the like, or combinations thereof. In one aspect, the pore size of the reaction segments or spots 305*a*-305*c* can be from about 1 to about 100 microns. The reaction segments or spots 305*a*-305*c* can be optically clean and smooth in appearance.

In another aspect, the reaction segments 305*a*-305*c* can provide a uniform end-color in a read zone for accurate and precise signal output or detection. In one example, a biological sample can slowly migrate vertically downward into the reaction segments 305$a$-305$c$. The end-color intensity of the reaction segments 305$a$-305$c$ can be measured by a user with optical observation and comparison to a color chart or scale or with a handheld LED meter as percent reflectance units and converted to copies of RNA or DNA per reaction using a curve set calibrated against a laboratory reference instrument, or as an optical image obtaining RGB values or pixel count which can be calibrated against a laboratory reference instrument. The concentration of RNA or DNA can be determined by the end-color intensity at a selected time or by kinetic rate determination.

In another aspect, the solid phase LAMP reaction medium 300*a* can further comprise reaction segments 305*a-c*. In one example, at least one section can be substantially free of reagents (e.g., 305*a* can be substantially free of reagents). In another aspect, the reaction segments 305*a-c* can be defined by at least three sections of discontinuous adhesive layers 304. The three reaction segments 305*a*, 305*b*, and 305*c* can include designations for testing of the same pathogen, one pathogen with multiple controls, or multiple different pathogens with or without specific positive or negative controls. In short, the reaction segments 305*a-c* can be designated and configured for testing in nearly any array so as to provide any desired parameters or protocols that yield a specific test for a specific outcome with a high degree of accuracy confidence. Furthermore, the reaction layer 306 can be configured with test spots 305*a-c* in a variety of numbers and location arrangements. For example, 2, 3, 4, 5, 6, 7, 8, 9, 10, or any other reasonable number of test spots may be included in reaction layer. Moreover, such test spots or reaction segments can be arranged linearly, side-by-side, or in nearly any other desired spatial arrangement within reaction layer 306.

Figure 3B:
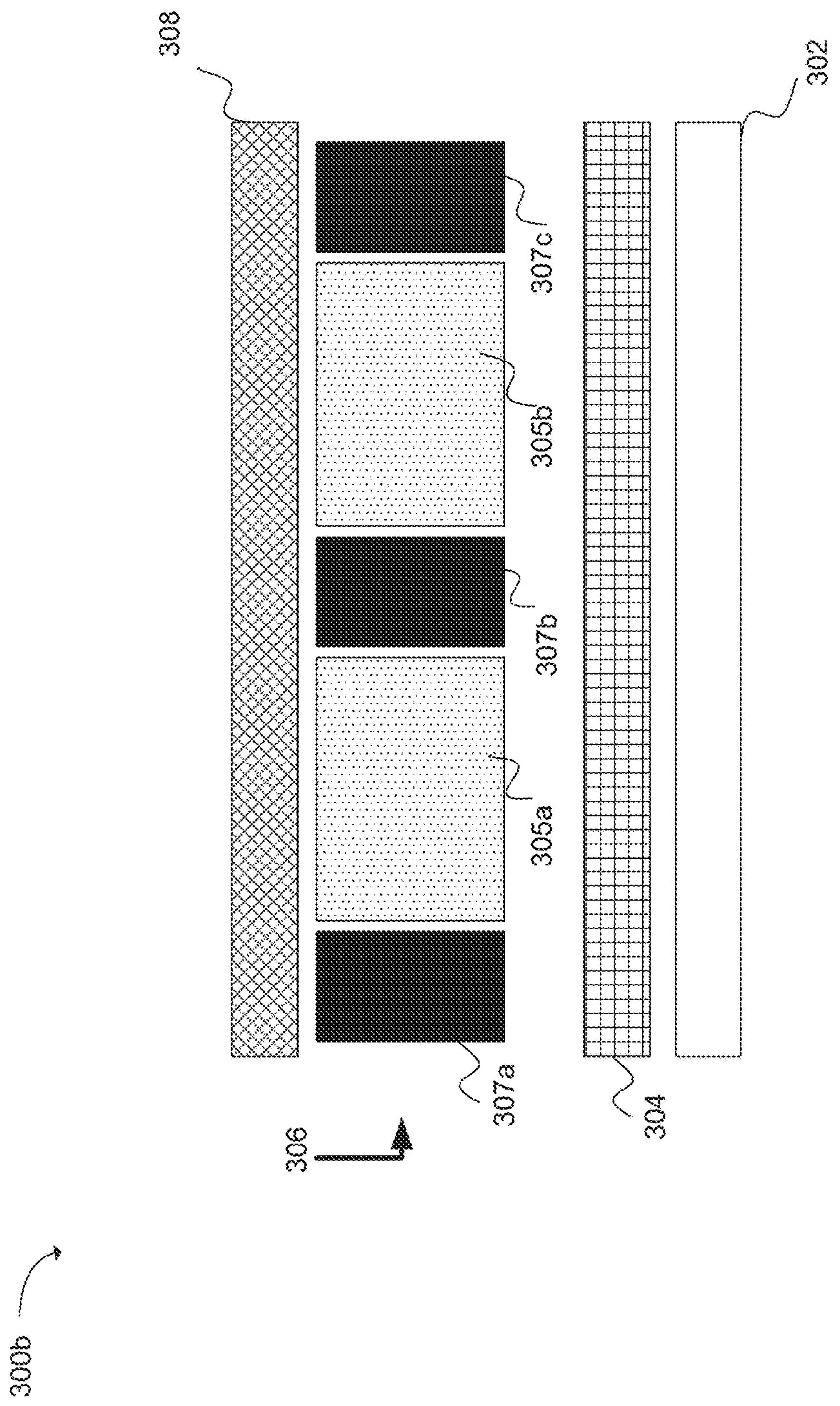
FIG. 3*b* illustrates a solid phase LAMP reaction medium with two testing sections in accordance with an example embodiment.

In one aspect, as illustrated in FIG. 3*b*, a solid phase LAMP reaction medium 300*b* can include the reaction segment 305*a* and 305*b* coupled between adhesive layer 304 and spreading or distribution layer 308. In one aspect, at least one reaction segment (e.g., 305*a* or 305*b*) can be a control section or spot that is substantially free of reagents. In another aspect, at least one of the reaction segments (e.g., 305*a* or 305*b*) can be configured to test for a target pathogen (e.g. will contain or otherwise support the reagents for a selected LAMP reaction).

Figure 3C:
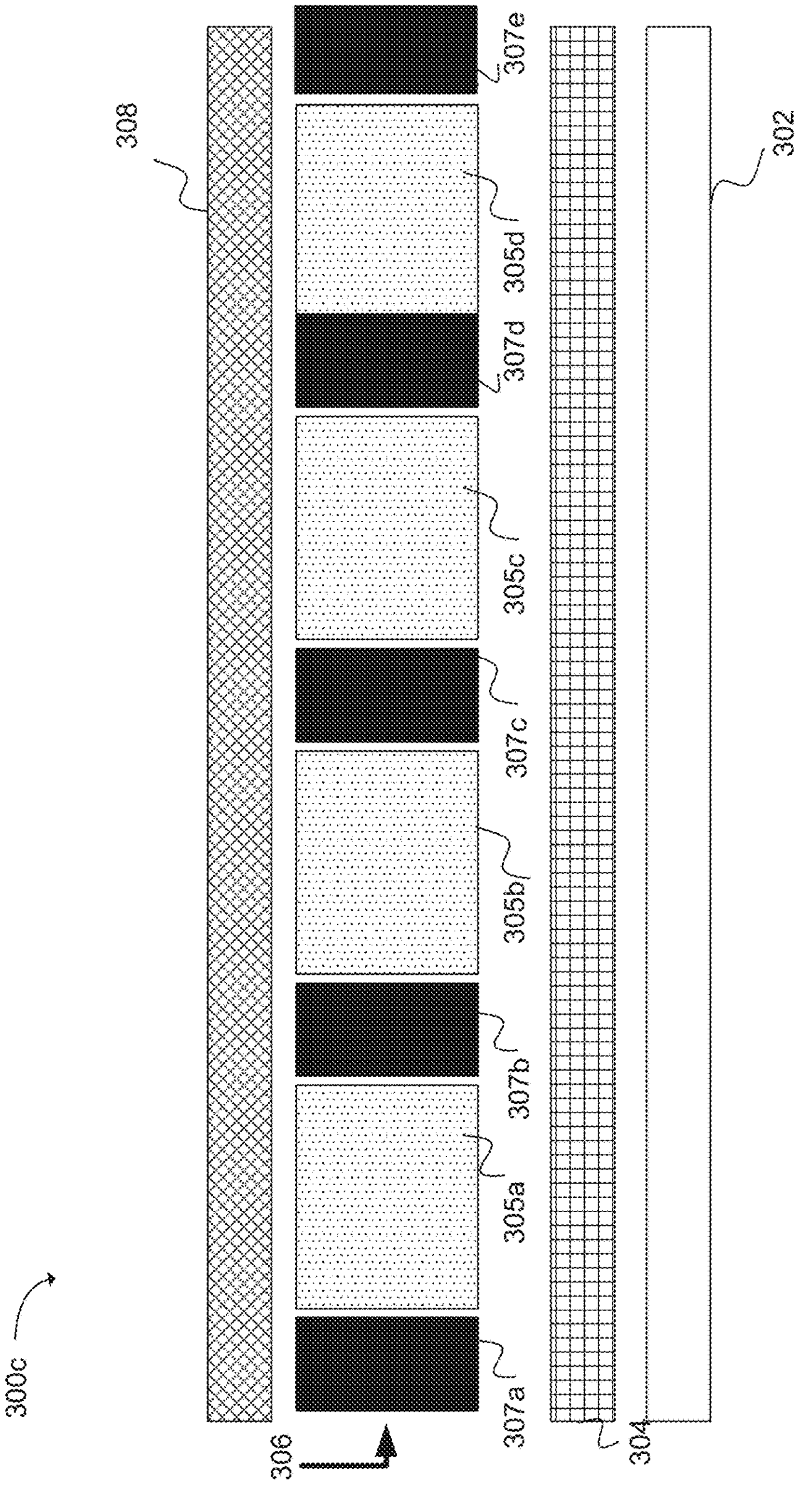
FIG. 3*c* illustrates a solid phase LAMP reaction medium with four testing sections in accordance with an example embodiment.

In yet another aspect, as illustrated in FIG. 3*c*, a solid phase LAMP reaction medium 300*c* can comprise a reaction layer 306 with reaction segments or spots 305*a*, 305*b*, 305*c*, 305*d* coupled between adhesive layer 304 and spreading layer 308. Each reaction segment can be separated by a spacer (e.g., 307*a*, 307*b*, 307*c*, 307*d*, 307*e*) from an adjacent reaction segment or spot.

Figure 3D:
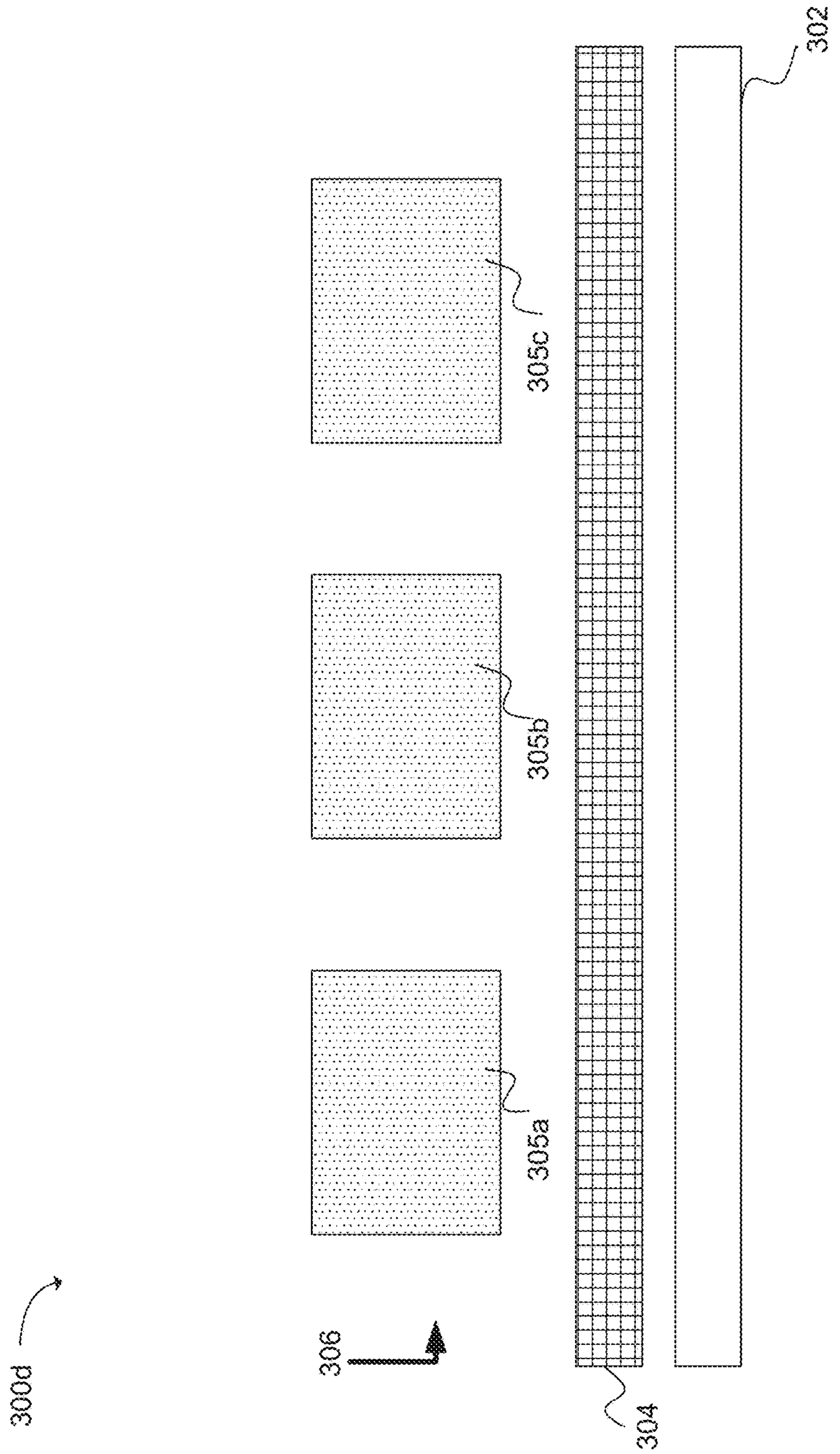
FIG. 3*d* illustrates a solid phase LAMP reaction medium with three testing sections and without a spreading layer in accordance with an example embodiment.

In yet another aspect, as illustrated in FIG. 3*d*, a solid phase LAMP reaction medium 300*d*, can comprise a substrate 302, an adhesive 304, a reaction layer 306 with reaction segments or spots 305*a*, 305*b*, and 305*c* without including a spreading layer. In this example, the sample can be deposited on each section of the reaction layer 305*a*, 305*b*, 305*c* separately, or simultaneously. Additionally, in this embodiment, no spacers are present between the adjacent reaction segments. However, in some embodiments, spacers can be included without the spreading layer 308 present.

Figure 3E:
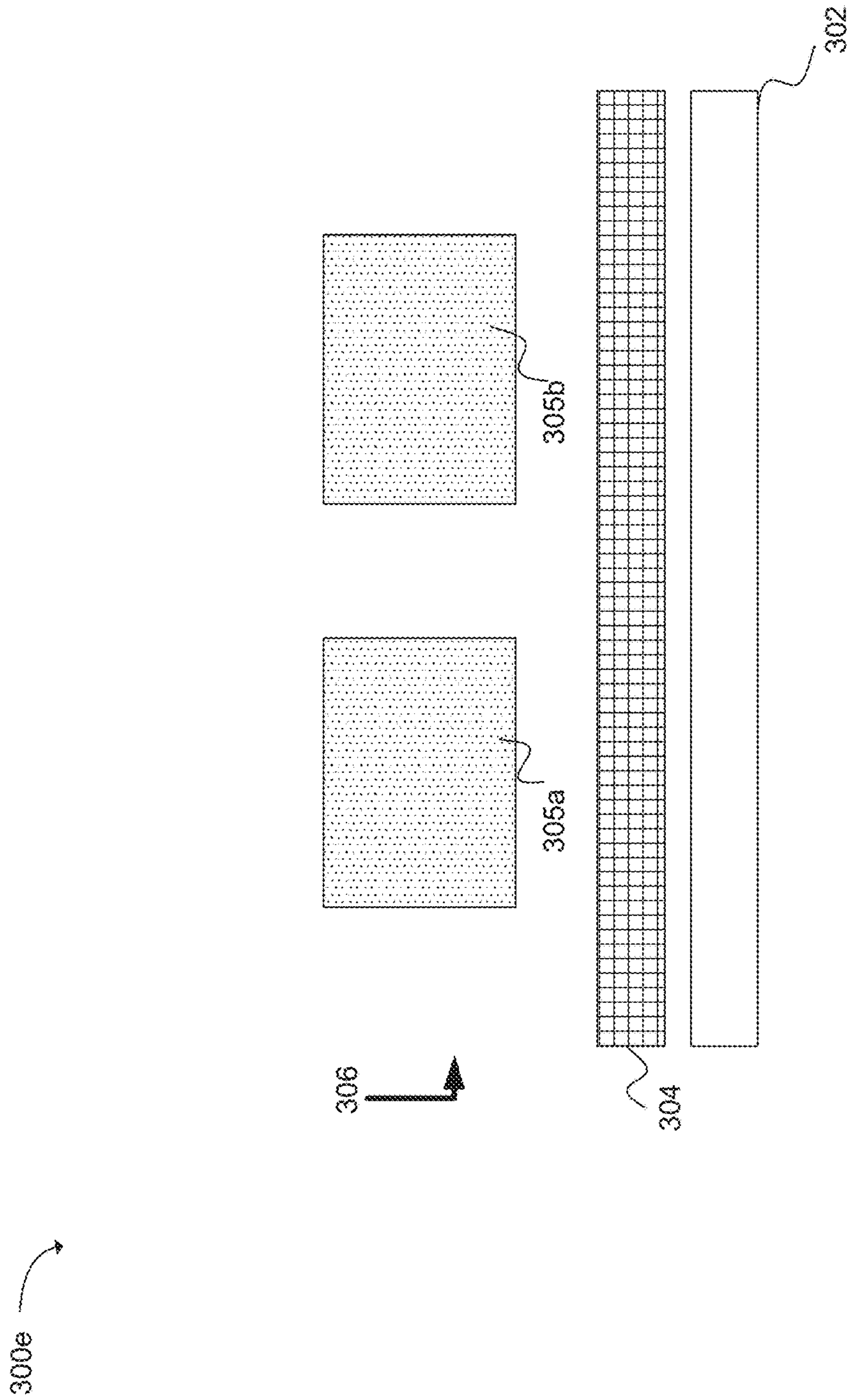
FIG. 3*e* illustrates a solid phase LAMP reaction medium with two testing sections and without a spreading layer in accordance with an example embodiment.

In yet another aspect, as illustrated in FIG. 3*e*, a solid phase LAMP reaction medium 300*e*, can comprise a substrate 302, an adhesive 304, and a reaction layer 306 having reaction segments or test spots 305*a* and 305*b* without including a spreading layer or any spacers. Again, spacers may still be included in another embodiment without also including the spreader layer 308. In this example, the sample can be deposited on each section of the reaction layer 305*a* and 305*b* separately and/or collectively.

Figure 3F:
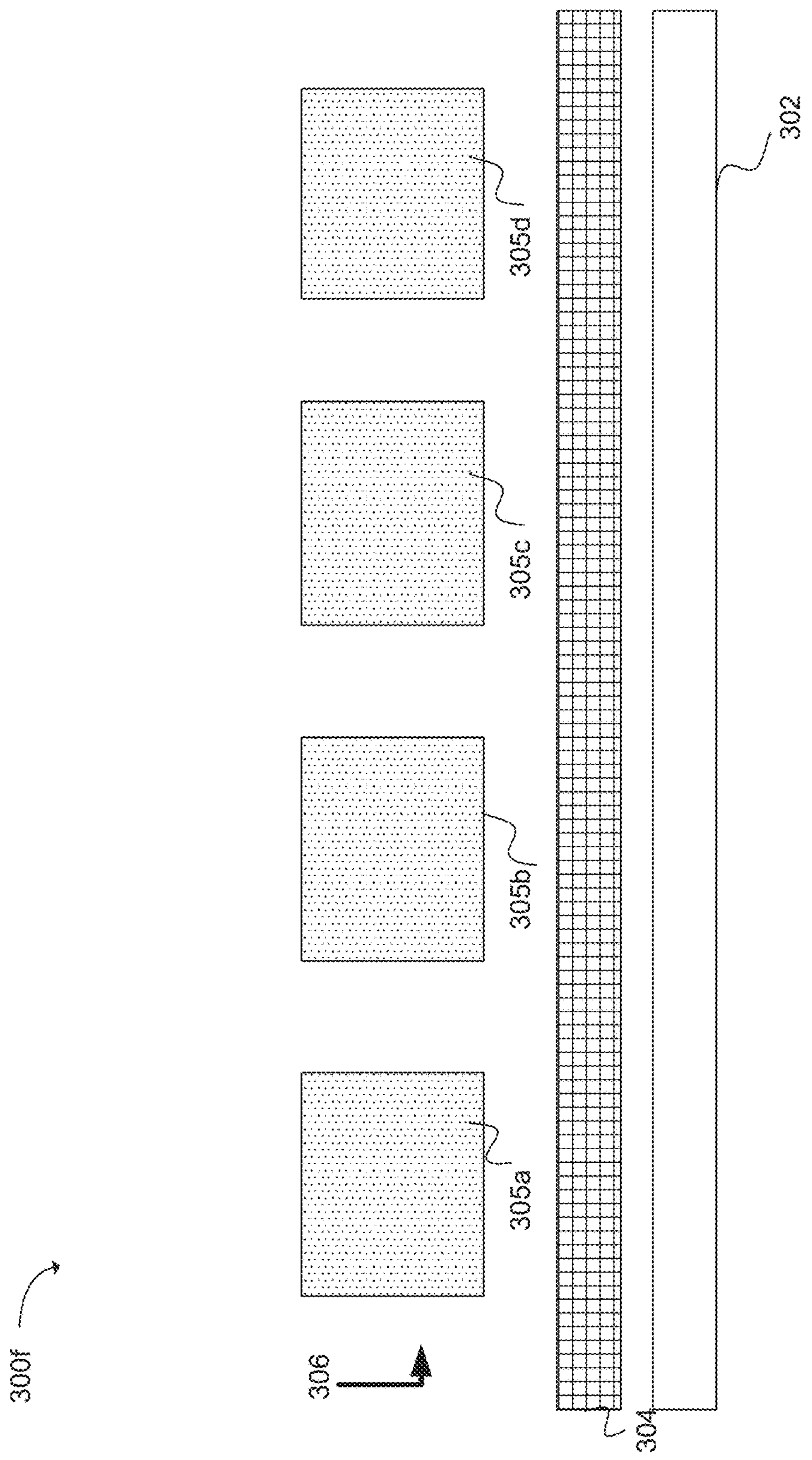
FIG. 3*f* illustrates a solid phase LAMP reaction medium with four testing sections and without a spreading layer in accordance with an example embodiment.

In yet another aspect, as illustrated in FIG. 3*f*, a solid phase reaction medium 300*f* that can be used for a LAMP analysis, can comprise a substrate 302, an adhesive 304, a reaction layer 306 having reaction segments 305*a*, 305*b*, 305*c*, and 305*d* without including a spreading layer and without having any spacers. Again, it is to be understood that spacers could be included between the adjacent reaction segments if desired, yet without including a spreading layer. In this example, the sample can be deposited on each section of the reaction layer 305*a*, 305*b*, 305*c*, 305*d* separately and/or collectively.

It is also to be understood that in other embodiments (not shown) a spreading layer 308 can be present with test spots or reaction segments coupled between the spreading layer and an adhesive 304, but without including any spacers. In short, depending on the specific test to be performed, the components of the solid phase reaction medium can be selected to accommodate the needs of the test in order to provide the most accurate outcome or in order to accommodate any manufacturing needs or reap certain other benefits.

In another aspect, the substrate 302 can be an optically transparent material. In another aspect, the substrate 302 can be an optically clear plastic carrier. In another aspect, the adhesive layer 304 can be substantially free of volatile agents. In another aspect, the adhesive layer 304 can be substantially free of agents that can interfere with a LAMP reaction. In another aspect, the adhesive layer 304 can be either continuously or discontinuously disposed on the substrate.

The adhesive layer can comprise various materials. In one example, the reaction layer 306 can comprise one or more of glass fiber, nylon, cellulose, polysulfone, polyethersulfone, cellulose acetate, nitrocellulose, hydrophilic PTFE, the like, or combinations thereof. In one example, an adhesive layer 304 can comprise an inert adhesive that does not affect the color change of the reaction segments or test spots in the reaction layer. In one example, the reaction layer 306 can be substantially free of chelating agents, magnesium, excess buffering capacity, pH-affecting reagents, or combinations thereof. In another example, the amount of adhesive can be minimized to prevent interference between the adhesive layer 304 and the reaction segments 305*a-c*.

The spreading layer can be configured to enhance the distribution and uniformity of the biological sample over the reaction segments 305*a*-305*c*. In another aspect, the spreading layer 308 can distribute or meter the saliva sample across the surface of the reaction layer 306. The spreading layer 308 can provide a uniform or substantially uniform concentration of saliva sample between the interface of the spreading layer 308 and the reaction layer 306. The spreading layer 308 can be one or more of a mesh material, an isotropic porous material having the same porosity throughout, or an anisotropic layer having a gradient in porosity, the like, or combinations thereof. In one aspect, an anisotropic layer can have pore sizes in the range of about 1 to about 100 microns. In one aspect, the spreading layer 308 can be hydrophilic to a degree sufficient to absorb and spread the sample. In another aspect, spreading layer 308 can be less hydrophilic than the reaction layer 306 underneath to allow the sample to be drawn out of the spreading layer 308 and into the reaction layer 306.

Precise permeability of the spreading layer 308 can be used for uniformly distributing the biological sample across the surface of the reaction layer 305*a-c* equally and evenly when a homogeneous biological sample is provided. In one aspect, the surface of the spreading layer 308 can be in direct contact with the reaction layer 305*a-c* for uniform vertical transfer of the biological sample through a lateral migration of the biological sample. In another aspect, the spreading layer 308 can comprise one or more of glass fiber, nylon, cellulose, polysulfone, polyethersulfone, cellulose acetate, nitrocellulose, polyester, hydrophilic polytetrafluoroethylene (PTFE), the like, or combinations thereof. In one example, the spreading layer 308 can be optically transparent. In one aspect, the material can be chemically treated to enhance the distribution of the biological sample across multiple reaction segments 305*a*-305*c*.

Adequate spacing between reaction segments or test spots 305*a*-305*c* can minimize or eliminate the probability of cross-contamination between each reaction segment. For example, reaction segment 305*a* may contaminate an adjoining segment such as 305*b* when the spacing between the two sections allows reagents from 305*a* to flow into 305*b*. In another aspect, the solid phase LAMP reaction medium 300*a* can further comprise spacers 307*a*, 307*b*, 307*c*, and 307*d* that can enforce a minimum space between reaction segments 305*a-c* that is from about 1.0 mm mm to about 3.0 mm (e.g., 2.5 mm).

In some embodiments, spacers 307*a*-307*d* can have a height that is greater than or equal to the reaction segments or test spots 305*a*-305*d* to create a physical barrier therebetween (e.g., when sample is separately administered to each test spot). In one example, the spacer height can be determined as a measure of the distance between the substrate 302 and a top surface of the spacer(s). Likewise, the reaction segment height can be determined as a measure of the distance between the substrate 302 and a top surface of the reaction segment. In some aspects, the spacers can have a height that is from 0 to 50% greater than a height of the reaction segments.

In other embodiments, spacers 307*a*-307*d* can have a height that is less than or equal to the reaction segments or test spots 305*a*-305*d* to create a physical barrier therebetween (e.g., when sample is separately administered to each test spot). Likewise, the reaction segment height can be determined as a measure of the distance between the substrate 302 and a top surface of the reaction segment. In some aspects, the spacers can have a height that is from 0 to 50% less than a height of the reaction segments.

In one example, the spacers 307*a-d* can include, but are not limited to, one or more of polysulfone, polyethersulfone, cellulose acetate, nitrocellulose, polystyrene, polyester, hydrophilic polytetrafluoroethylene (PTFE), the like, or combinations thereof. In another example, the spacers 307*a-d* can include, but are not limited to, glass fiber, nylon, cellulose, the like, or combinations thereof. In another example, the spacers 307*a-d* can comprise a hydrophobic material (e.g., polysulfone, polyethersulfone, cellulose acetate, nitrocellulose, polystyrene, polyester, hydrophilic polytetrafluoroethylene (PTFE), or the like) but not a hydrophilic material (glass fiber, nylon, cellulose, or the like). In one aspect, the spacers 307*a-d* can be oriented in the same plane as the reaction segments 305*a-c* and can be oriented therebetween.

In another example, as illustrated in FIG. 3*a*, a solid phase LAMP reaction medium can include a spreading layer 308, and a reaction layer 306, joined by adhesive layer 304. In one example, the material type of spacers 307*a*-307*d* can enhance or otherwise positively affect the degree of spreading. For example, polystyrene spacers can result in more spreading than other material types. A solid phase reaction medium without a spreading layer 308 may simplify manufacturing at the cost of user simplicity. The user could apply the saliva sample to each of the test spots 305*a-c* individually in this case. However, spacers of a material that repels or minimally absorbs the sample such as polystyrene can assist the spreading layer in providing uniform spreading results. Moreover, such spacers of such materials can also assist in spreading a sample when a spreading layer 308 is not used.

Figure 4:
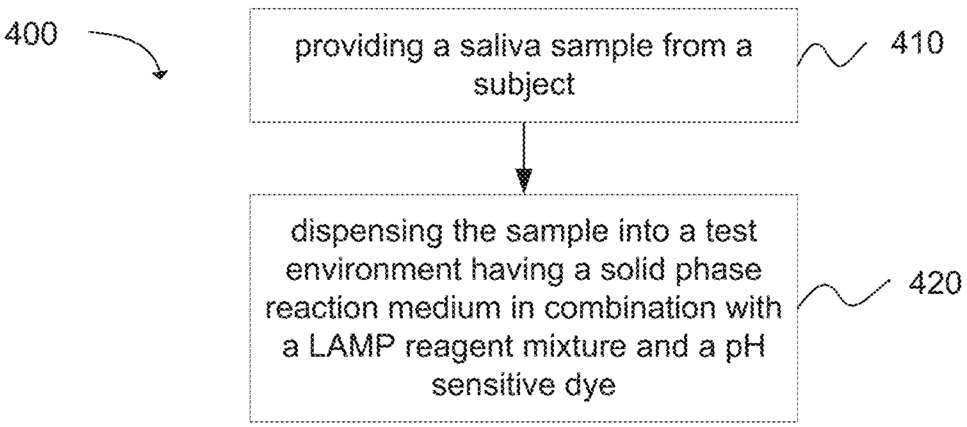
FIG. 4 depicts a method of testing for a presence of a viral pathogen in accordance with an example embodiment.

Referring to FIG. 4, a method 400 of testing for a presence of a viral pathogen is shown and can comprise providing a saliva sample from a subject, as shown in block 410, and dispensing the sample into a test environment having a solid phase reaction medium in combination with a LAMP reagent mixture and a pH sensitive dye, as shown in block 420.

In one aspect, the method can comprise minimizing the amount of volatile agents, hygroscopic agents, and non-pH sensitive agents capable of discoloring the solid phase medium. In another aspect, the method can comprise providing an amount of one or more target primers, DNA polymerase, and a re-solubilization agent sufficient to facilitate a LAMP reaction. In another aspect, the method can comprise providing an amount of reverse transcriptase sufficient to facilitate an RT-LAMP reaction. In another aspect, the method can comprise providing an amount of one or more target primers sufficient to detect the viral pathogen. In another example, the method can comprise generating a test result in less than one hour after dispensing the sample into the test environment.

Figure 5:
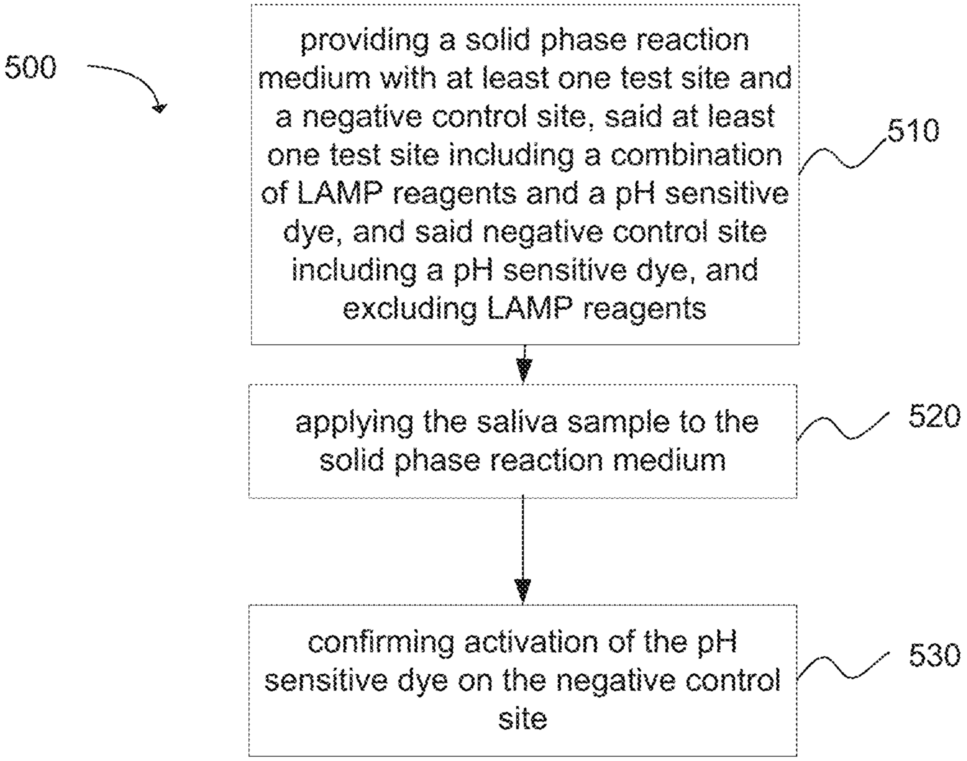
FIG. 5 depicts a method of confirming suitability of a saliva sample for testing with a solid phase LAMP reaction in accordance with an example embodiment.

In yet another embodiment, as depicted in FIG. 5, a method 500 of confirming suitability of a saliva sample for testing with a solid phase LAMP reaction can comprise providing a solid phase reaction medium with at least one test site or spot said at least one test site or spot including a combination of LAMP reagents and a pH sensitive dye. In another aspect, the method can further comprise providing a solid phase reaction medium with at least one negative control site, said negative control site including a pH sensitive dye, and excluding LAMP reagents, as shown in block 510. In another aspect, the method can further comprise applying the saliva sample to the solid phase reaction medium, as shown in block 520. In another aspect, the method can further comprise confirming activation of the pH sensitive dye on the negative control site, as shown in block 530.

In one example, the pH sensitive dye can be at least one of phenol red, phenolphthalein, azolitmin, bromothymol blue, naphtholphthalein, cresol red, or combinations thereof. In another example, the LAMP reagents can be substantially free of volatile reagents, pH-affecting reagents, magnesium-containing reagents, or combinations thereof. In another aspect, the LAMP reagents can comprise non-interfering LAMP reagents including DNA polymerase, reverse transcriptase, primers for a target region, or combinations thereof.

In another aspect, the method can further comprise providing the test site or spot defined by at least two sections of discontinuous adhesive layers. In another example, the method can further comprise providing the test site or spot defined by at least three sections of discontinuous adhesive layers.

Figure 6:
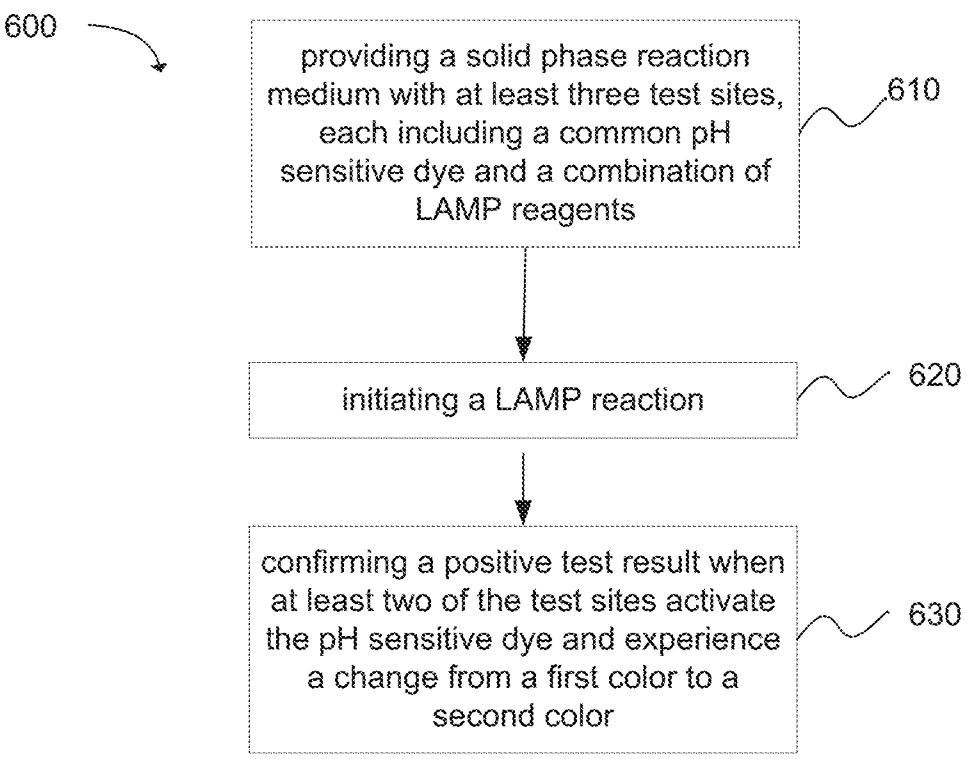
FIG. 6 depicts a method of maximizing accuracy of a positive test result from a solid phase LAMP reaction in accordance with an example embodiment.

In yet another embodiment, as depicted in FIG. 6, a method 600 of maximizing accuracy of a positive test result from a solid phase LAMP reaction can comprise providing a solid phase reaction medium with at least three test site or spots, each including a common pH sensitive dye and a combination of LAMP reagents, as shown in block 610. In one aspect, each site can include a different primer sequence from a target pathogen. In another aspect, the method can comprise initiating a LAMP reaction, as shown in block 620. In another aspect, the method can comprise confirming a positive test result when at least two of the test site or spots activate the pH sensitive dye and experience a change from a first color to a second color, as shown in block 630. In another aspect, the method can further comprise providing an amount of reverse transcriptase sufficient to facilitate an RT-LAMP reaction.

In one example, the pH sensitive dye can be at least one of phenol red, phenolphthalein, azolitmin, bromothymol blue, naphtholphthalein, cresol red, or combinations thereof. In another aspect, the LAMP reagents can be substantially free of volatile reagents, pH-affecting reagents, magnesium-containing reagents, or combinations thereof.

In another aspect, the target pathogen can comprise a viral pathogen, a bacterial pathogen, a fungal pathogen, or a protozoa pathogen. In one aspect, the target pathogen can comprise a viral pathogen. In another aspect, the viral pathogen can comprise a dsDNA virus, an ssDNA virus, a dsRNA virus, a positive-strand ssRNA virus, a negative-strand ssRNA virus, an ssRNA-RT virus, or a ds-DNA-RT virus. In another aspect, each primer sequence can match a sequence from a viral target comprising H1N1, H2N2, H3N2, H1N1pdm09, or SARS-CoV-2.

In another aspect, the specific target nucleotide sequences to be detected can be target nucleotides corresponding to human biomarkers. Any disease that has a target nucleotide corresponding to a human biomarker for a disease can be detected. Various types of diseases can be detected including one or more of: breast cancer, pancreatic cancer, colorectal cancer, ovarian cancer, gastrointestinal cancer, cervix cancer, lung cancer, bladder cancer, many types of carcinomas, salivary gland cancer, kidney cancer, liver cancer, lymphoma, leukemia, melanoma, prostate cancer, thyroid cancer, stomach cancer, the like, or combinations thereof. For example, biomarkers for various types of diseases can be detected by detecting target nucleotides corresponding to one or more of: alpha fetoprotein, CA15-3 and CA27-29, CA19-9, C!-125, calcitonin, calretinin, carcinoembryonic antigen, CD34, CD99MIC 2, CD117, chromogranin, chromosomes 3, 7, 17, and 9p21, cytokeratin, cesmin, epithelial membrane antigen, factor VIII, CD31 FL1, glial fibrillary acidic protein, gross cystic disease fluid protein, hPG80, HMB-45, human chorionic gonadotropin, immunoglobulin, inhibin, keratin, lymphocyte marker, MART-1, Myo D1, muscle-specific actin, neurofilament, neuron-specific enolase, placental alkaline phosphatase, prostate-specific antigen, PTPRC, S100 protein, smooth muscle action, synaptophysin, thymidine kinase, thyroglobulin, thyroid transcription factor-1, tumor M2-PK, vimentin, the like, or combinations thereof.

In one example, the positive control can include a synthetic DNA target as one of the test sections to confirm that the DNA template is stable. In another aspect, the negative control can include: (a) enzyme reagents without primers, or (b) enzyme reagents with primers that are targeted to a distinct virus.

In another example, 3 test sections can be used to achieve an enhanced coverage of different viral strains (e.g., SARS-CoV-2). The timing and limit of detection can be selected for each primer. In one example, with a first primer, 97% coverage of a virus (e.g., SARS-CoV-2) can be achieved. In another example, including 2 additional primers that are slower and less sensitive compared to the first primer may not enhance the coverage for the virus. In another example, the plurality of test sections can be used to achieve coverage of different viral pathogens (e.g., SARS-CoV-2, H1N1, H2N2, H3N2, H1N1pdm09, and the like).

Solid-Phase Medium LAMP Testing Process and Methodology

LAMP testing on a solid-phase medium can be enhanced in several ways. First, the test environment can be monitored to prevent variations that might impact the testing process. Second, the storage conditions of the biological sample testing apparatus can impact the validity of the biological sample testing apparatus. When these conditions are tightly monitored, the biological sample testing apparatus can have enhanced operability in comparison to liquid-based LAMP tests.

Figure 7:
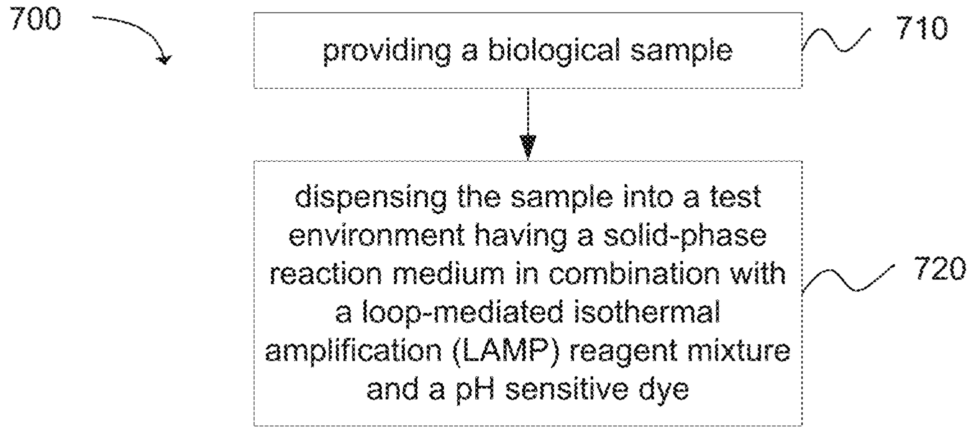
FIG. 7 depicts a method of testing for a presence of a target nucleotide sequence in accordance with an example embodiment.

Various methods can be used that relate to the testing environment. In one embodiment, as depicted in FIG. 7, a method of testing for a presence of a target nucleotide sequence can comprise: providing a biological sample, as shown in block 710, and dispensing the sample into a test environment having a solid-phase reaction medium in combination with a loop-mediated isothermal amplification (LAMP) reagent mixture and a pH sensitive dye, as shown in block 720. In one aspect, the method can comprise providing an amount of reverse transcriptase sufficient to facilitate an RT-LAMP reaction.

The type of biological sample can affect the test environment. For example, a saliva sample can have a buffering capacity that can reduce the contrast of the test output. In one example, the biological sample can be at least one of: saliva, mucus, blood, urine, sweat, exhaled breath condensate, or feces. In another example, the method can further comprise collecting the biological sample using one or more of a saliva collection device, a nasal swab, a blood collection device, a urine collection device, a sweat collection device, an exhaled breath collection device, or a stool collection device.

The test environment can be controlled to provide consistent test outputs. In one aspect, the test environment can be substantially free of volatile reagents, pH-affecting reagents, drying agents, or combinations thereof. Each of these reagents can reduce the consistency of the test results by introducing variables that might be compensated for with additional analysis.

Another test environment variable that can be monitored is the rate that the temperature increases when the biological test apparatus is used to heat the biological sample. In one aspect, the method can comprise raising a test environment temperature at a rate of about 0.1° C. per second. In one example, test environment temperature can be raised at a rate of about 0.1° C. per second to about 0.2° C. per second. In one example, the reverse transcriptase can be activated at about 55° C. and the DNA polymerase can be activated at about 65° C. Consequently, a ramp rate higher than about 0.2° C. per second can interfere with the coordinated action of reverse transcriptase and DNA polymerase in a LAMP reaction. In one example, the ramp rate can be raised until the test environment temperature is in a range from about 60° C. to about 67° C. In some examples, when the test environment is increased to about 55° C. (i.e. the temperature at which the reverse transcriptase can be activated), with a ramp rate of about 0.1° C. from 55° C. to about 65° C., the biological sample test apparatus can provide invalid results. Therefore, the ramp rate should be monitored not just in the testing environment temperature range from about 55° C. to about 65° C., but also as the biological sample is being heated to about 55° C.

The variability of the testing environment can also affect the results from the biological sample test apparatus. In one aspect, the method can comprise providing a heating uniformity in the testing environment that has a variability of less than 1° C. The spatial variability of the temperature around the testing cartridge should not be greater than about 0.5° C. to avoid interference with the LAMP reaction.

In another aspect, the method can comprise a testing time of from about 15 minutes to about 30 minutes for a saliva sample. In another aspect, the method can comprise a testing time of from about 30 minutes to about 45 minutes for a saliva sample. In another aspect, the method can comprise a testing time of from about 45 minutes to about 60 minutes for a saliva sample. In another aspect, the method can comprise a testing time of from about 60 minutes to about 90 minutes for a saliva sample. In another aspect, the method can comprise a testing time of from about 20 minutes to about 30 minutes for a nasopharyngeal sample. In another aspect, the method can comprise a testing time of from about 30 minutes to about 40 minutes for a nasopharyngeal sample.

In another aspect, the method can further comprise providing a solid phase reaction medium comprising glass fiber, nylon, cellulose, polysulfone, polyethersulfone, cellulose acetate, nitrocellulose, hydrophilic PTFE, the like, or combinations thereof. In another aspect, the solid phase reaction medium can comprise a material as otherwise disclosed herein.

In one aspect, the target nucleotide sequence can be from at least one of a viral pathogen, a bacterial pathogen, a fungal pathogen, or a protozoan pathogen. In one aspect, the target nucleotide sequence can be from a viral pathogen. In another aspect, the viral pathogen can be from the group consisting of: Coronoviridae, Orthomyxoviridae, Paramyxoviridae, Picornaviridae, Adenoviridae, and Parvoviridae. In another aspect, the viral pathogen can be selected from the group consisting of: severe acute respiratory syndrome coronavirus (SARS-CoV-1), severe acute respiratory syndrome coronavirus 2 (SARS-CoV-2), Middle East respiratory syndrome (MERS), influenza, and H1N1. In one aspect, the target nucleotide sequence can be from a severe acute respiratory syndrome coronavirus 2 (SARS-CoV-2) pathogen.

The test accuracy of the biological sample testing apparatus can be affected by the length of storage before testing and the storage conditions (e.g., storage temperature, humidity, and the like). In one embodiment, a biological sample testing apparatus can comprise a substrate engaging a solid phase reaction medium in combination with a dehydrated loop-mediated isothermal amplification (LAMP) reagent mixture and a dehydrated pH-sensitive dye. In one aspect, the apparatus can provide a degree of test accuracy of at least about 95%, 96%, 97%, 98%, or 99% after storage for 6 months when stored at a selected temperature (e.g., room temperature of about 25° C.). In one aspect, the apparatus can provide a degree of test accuracy of at least about 95%, 96%, 97%, 98%, or 99% after storage for 12 months when stored at a selected temperature. In another aspect, the apparatus can provide a degree of test accuracy of at least about 95%, 96%, 97%, 98%, or 99% after storage for 2 years when stored at a selected temperature. In another aspect, the apparatus can provide a degree of test accuracy of at least about 95%, 96%, 97%, 98%, or 99% after storage for 3 years when stored at a selected temperature. In another aspect, the selected temperature can be any temperature in a range between about −20° C. and about 37° C.

The biological sample testing system can include a housing. In yet another embodiment, a biological sample testing system can comprise: a substrate engaging a solid phase reaction medium in combination with a dehydrated loop-mediated isothermal amplification (LAMP) reagent mixture and a dehydrated pH-sensitive dye, said housing operable to receive a biological sample. In one aspect, the biological sample testing system can further comprise a heater configured to isothermally heat the container to an internal temperature sufficient to initiate and sustain a LAMP reaction between the LAMP reagent mixture and a biological sample for a time used to generate a test result via the pH-sensitive dye.

In one aspect, the substrate can comprise an optically transparent material. In another aspect, the substrate can engage the solid phase reaction medium via an adhesive. In another aspect, the adhesive can be substantially optically transparent. In another aspect, the substrate can comprise a portion of a housing. In another aspect, the biological sample testing system can further comprise an adhesive layer disposed on the substrate, a reaction layer disposed on the adhesive layer, and a spreading layer disposed on the reaction layer. In another aspect, the biological sample testing system can further comprise a spacer layer oriented in the same plane as the reaction layer. In another aspect, the biological sample testing system can further comprise a housing disposed against the substrate. In one example, the housing can be further disposed against the spreading layer. In another example, the housing can substantially enclose the substrate, adhesive layer, reaction layer, and spreading layer.

In one example, an operation for a biological testing system, as illustrated in FIG. 8, can include: (a) using the sponge to collect saliva, (b) plunging the sponge into a collection tube, (c) diluting the collection tube with water to dilute the saliva sample down to 5% to stabilize the saliva pH and to reduce the buffering capacity of the saliva, (d) transferring the saliva sample to the test strip which in the cartridge using a pipette by applying the saliva sample to a single location so that a capillary and a mesh layer can spread the saliva sample to the discrete segments of the reaction layer; (e) putting the cover onto the cartridge and locking the cover in place; (f) verifying that the pH of the saliva sample is within a testing range by examining the segments of the reaction layer; (g) inserting the cartridge into the heater, and (h) verifying the proper positioning of the cartridge within the heater; (i) activating the heater; (j) reading the results after about 30 minutes when the testing has been completed; (k) determining whether the results are valid, and (1) determining whether the result is positive or negative.

Operation (a) can be performed by collecting the saliva via a sponge-collection device or a passive drool device. When a sponge-collection device is used, the sponge can be plunged into the collection tube to release the saliva into the collection tube (operation (b)). The collection tube can be diluted with water to decrease the buffering capacity of the saliva, reduce the viscosity of the saliva, and allow for an increased uniformity in the sample (operation (c)). The saliva sample, when transferred to the test strip, can be individually applied to each section of the test strip or can be applied to the center of the test strip with the spreading layer spreading the sample throughout the testing area of the test strip (operation (d)). The test strip can be covered to avoid contamination with the test environment (operation (e)). The pH of the saliva sample can be tested through various means such as a colorimetric device, a fluorescent reader, or by a simple comparison with a pH color chart for the pH indicator in use (operation (f)). The cartridge can be placed into the heater and activated (operations (g), (h), and (i)) with the time recorded in order to measure the total reaction time and time to reach a positive or negative result. The results can be read after 30 minutes (operation (j)), or the results can be read as soon as the results show a positive result. The speed with which a positive result appears can be correlated to the concentration of the pathogen. The results can be determined to be valid (operation (k)) based on the positive controls, negative controls, other pathogen results, or a combination thereof. The results can be determined to be positive or negative, when a pH-based indicator is used, by comparing the color of the results with a color comparison chart for the pH-based indicator. The results can also be determined to be positive or negative by measuring the wavelength of the color absorbed.

Figure 8A:
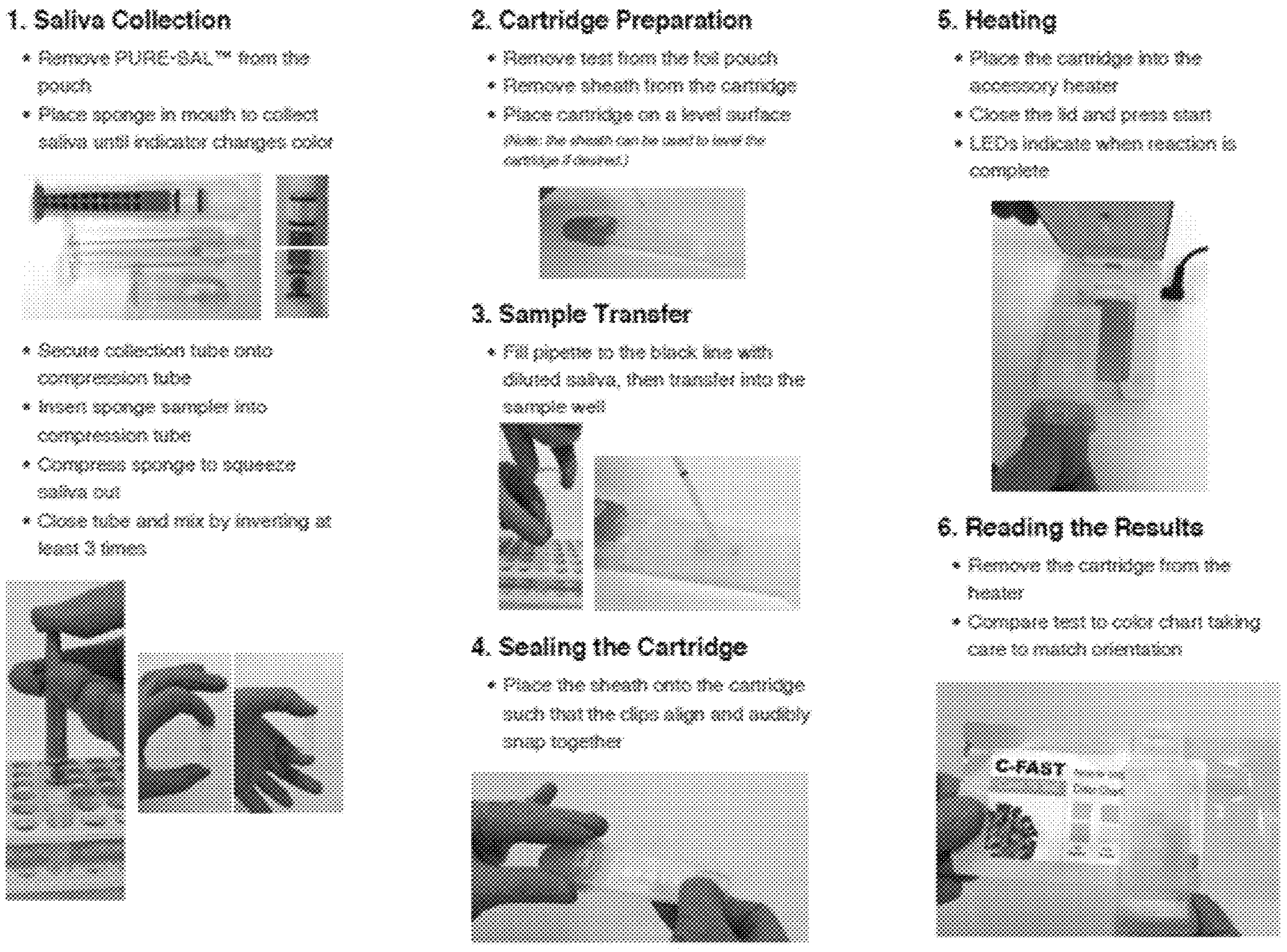
FIG. 8*a* depicts operations for a biological testing kit in accordance with an example embodiment.
Figure 8B:
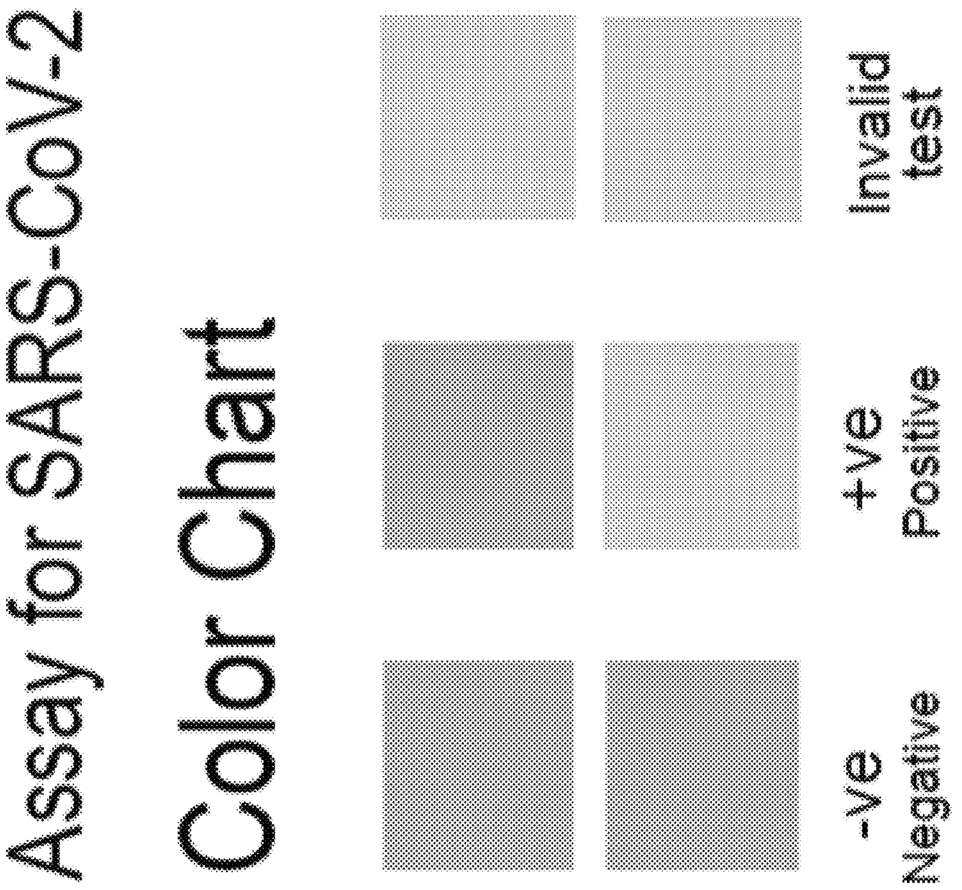
FIG. 8*b* illustrates a color chart for a biological testing kit in accordance with an example embodiment.

In another disclosure embodiment, a biological testing kit can comprise one or more of a saliva collection device, a collection tube, a cartridge, a pipette, a heater, a color chart, or combinations thereof, as illustrated in FIGS. 8*a* and 8*b*. The saliva collection device can be a sponge-collection device or a passive-drool device.

In one example, as illustrated in operation 1 from FIG. 8*a*, a user can collect saliva using one or more operations including: (a) removing a Pure-Sal™ from a pouch of a biological testing kit, (b) placing the sponge of the Pure-Sal™ to collect saliva until the indicator changes color or some other indication is provided that shows the end of the saliva collection process, (c) securing the collection tube into a compression tube, (d) inserting the sponge sampler into the compression tube, (e) compressing the sponge to squeeze the collected saliva (without some of the degradative saliva enzymes) into the compression tube, (f) closing the tube, and (g) mixing the tube by inverting a number of times (e.g., 1 to 10 times).

After the saliva has been collected in a tube and adequately mixed, the user can prepare the cartridge, as illustrated in operation 2 from FIG. 8*a*. The user can (i) remove the test from the foil pouch, (ii) remove the sheath from the cartridge, and (c) place the cartridge on a level surface. The user can also transfer the sample, as illustrated in operation 3 from FIG. 8*a*, by filling the pipette to the black line with diluted saliva (e.g., diluted with water), and transferring into the sample well. The user can also seal the cartridge, as illustrated in operation 4 from FIG. 8*a*, by placing the sheath onto the cartridge such that the clips align and snap together. The user can also heat the cartridge, as illustrated in operation 5 in FIG. 8*a*, by placing the cartridge into the accessory heater, closing the lid and initiating the accessory heater, which can indicate via LEDs when a reaction has been completed.

After the reaction has been completed, as illustrated in operation 6 of FIG. 8*a*, a user can remove the cartridge from the heater and compare the cartridge to a color chart while also ensuring that the orientation between the color chart and the cartridge is correct. As further illustrated in FIG. 8*b*, a color chart, as illustrated with reference to the viral pathogen SARS-CoV-2, can include 6 squares in 2 rows and 3 columns. A first column can (−ve) can indicate a negative result, a second column (+ve) can indicate a positive result, and a third column (invalid test) can indicate an invalid result.

For example, the first column can indicate a negative result because both the top row square and the bottom row square are approximately a red-orange color, which can occur when nucleotide amplification for a LAMP reaction does not occur in either square. The second column can indicate a positive result because the top row square is approximately a red-orange color, which can occur when nucleotide amplification for a LAMP reaction does not occur, but the bottom square is approximately an orange-yellow color, which can occur when nucleotide amplification for a LAMP reaction occurs, and indicates that the viral pathogen was present. The third column can indicate an invalid result because the top row square is approximately an orange-yellow color, which can occur when nucleotide amplification for a LAMP reaction occurs, but the bottom square is approximately an orange-yellow color, which can occur when nucleotide amplification for a LAMP reaction occurs. But for the third column, the reason for the color change from the red-orange color to the orange-yellow color can be inconclusive because the negative control (e.g., the top row) also changed color.

Therefore, a user can compare the color chart to the test in the cartridge to determine a test result. The color chart illustrated in FIG. 8*b* is one example. The color chart can include additional rows or columns to accommodate any number of tests for additional controls, additional pathogens, or different primers directed to the same pathogens. Moreover, the test can be self-administered by the subject, or can be administered by a trained technician, a nursing assistant, a nurse, a physician assistant, a medical doctor, or any other person qualified to administer the test and interpret the results.

EXAMPLES

The following examples are provided to promote a more clear understanding of certain embodiments of the present invention, and are in no way meant as a limitation thereon.

Material Assembly for Paper Based LAMP Reaction

Example 1—Paper-Based Lamp Assembly

For the paper-based LAMP assembly, several materials were screened to design a portable and compact assembly. For screening of the spreading layer, two paper strips, one with primers and one without primers, were placed together and 50 μL of RNA at a concentration of 0.2 ng/μL was loaded to saturate both strips. Materials might not have a substantial effect on the paper's pH for a few reasons: (a) either the paper was too acidic to change color before incubation, or (b) the paper was too basic which would prevent any color change from the reaction. Materials that prevented cross-talk between the two paper strips were further tested with the other device components.

Figure 9:
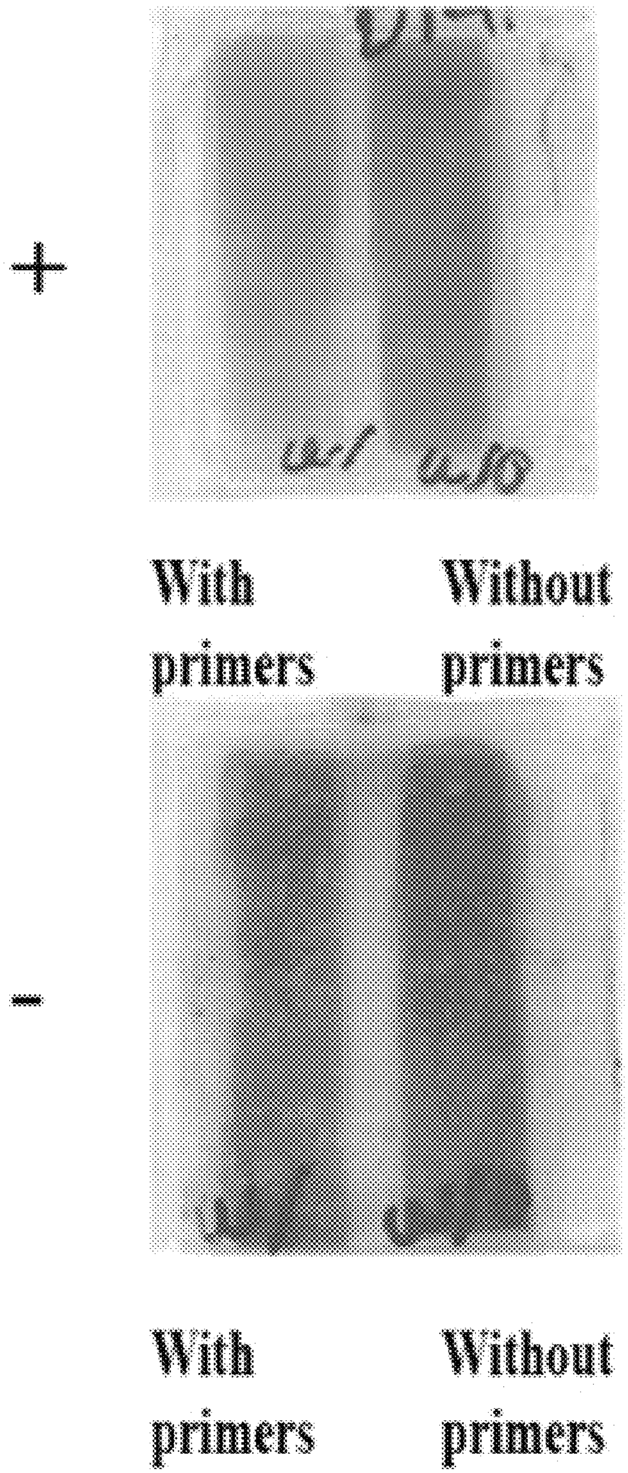
FIG. 9 illustrates a paper-based LAMP assembly in accordance with an example embodiment.

The paper-based LAMP assembly had dimensions of about 24×54 mm. The paper-based LAMP assembly comprised: (i) a reading layer, (ii) 2 reaction strips, and (iii) a spreading layer. The reading layer comprised a transparent 3 millimeter Melinex® backer for support. The Melinex® backer was attached to the 2 reaction strips, which were each formed of 5 mm×20 mm chromatography paper (e.g., Whatman® Grade 1 chromatography paper) contacted by a double-sided adhesive (ArClean® 90178). The two test strips were separated by 2.5×20 mm 10-millimeter polystyrene spacers to prevent cross-talk between the two test strips. The spreading layer comprised a polyester sulfone mesh (Saaticare® PES 105/52). The sample was loaded on the spreading layer. FIG. 9 shows an example of the assembly.

Example 2—Material Screening

Paper-based materials were selected based on five criteria: (a) stability of formulation when dried on the substrate, (b) intensity of color change when rehydrated with sample, (c) ability of the sample to evenly wick throughout the paper-based substrate, (d) ability of the material to remain inert throughout the reaction, and (e) ability of the paper-based material to demonstrate a color change upon amplification. Whatman® Grade 1 chromatography paper was tested and used for optimization. When assembling two test strips together, it was observed that the distribution of fluid was uneven because the LAMP reaction used a large area of the Grade 1 chromatography. Selecting a chromatography paper that is thicker than the Grade 1 chromatography paper (e.g., Ahlstron Grade 222 chromatography paper) allowed the test strips to be about 5 mm×6 mm in surface area while also carrying the same amount of sample and reagents as the Grade 1 chromatography paper, which allowed greater uniformity of spreading during rehydration.

Example 3—Material Screening—Grade 1 and Grade 222 Chromatography Paper

Figure 10:
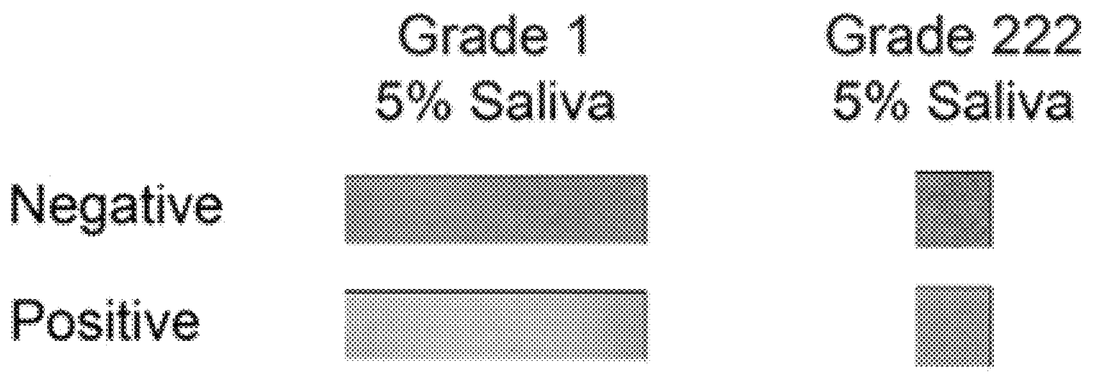
FIG. 10 illustrates material screening of grade 1 and grade 222 chromatography paper in accordance with an example embodiment.

In one example, as shown in FIG. 10, the images illustrate examples of the color contrast that can be generated. In one example, grade 1 chromatography paper was used. In the other example, grade 222 chromatography paper was used. In both cases, RT-LAMP reagents were dried and rehydrated with 25 μL of 5% saliva and 95% water. The positive samples contained heat-inactivated SARS-CoV-2 spiked in at 10 k copies per reaction, and negative samples were 5% saliva (without virus) and 95% water. The images were captured at the 90-minute time point incubation at 65° C.

As illustrated in FIG. 10, the color contrast between the negative result for grade 1 paper and the positive result for grade 1 paper is less pronounced than the color contrast between the negative result for grade 222 paper and the positive result for grade 222 paper. Therefore, the thicker paper produced enhanced color contrast.

Example 4—Paper Assembly Protocol

A paper assembly protocol can include: (1) cut out polyethylene terephthalate (PET) into rectangles having dimensions of 80 mm×7 mm to create 2 per device; (2) cut out chromatography paper into rectangles having dimensions of 33 mm×5 mm to create 1 per device; (3) cut out a large sheet of double-sided tape and tape the PET rectangles onto it so that there are 2 cm in between each PET rectangle; (4) cut out all of the rectangles so that there is extra tape on all sides; (5) peel off the tape with the PET on it and tape the chromatography paper on the opposite side of the PET leaving about 1 cm outside the tape; (6) add 25 ul of sample onto the chromatography paper by using a single spot that is close to the inside of the device; (7) tape the other PET strip to cover the sample (i.e. the side with the tape should touch the sample and the PET should be on the outside); (8) fold any tape that is sticking out onto the PET tape to further seal; (9) add 1 ml of solvent to the bottom of a 15 ml tube; (10) put the assembled paper device in the tube so that the chromatography paper sticking out is in the solvent; (11) close the tube; and (12) incubate at 65° C. for 1 hour.

Materials for pH-Based Paper Based LAMP Analysis

Example 5—Limit of Detection (LoD)

An LoD study used a primer set targeted for various regions of SARS-CoV-2 and 2-fold serial dilutions of heat-inactivated SARS-CoV-2 at concentrations of 2.5, 5, 10, 20, and copies/μL in a reaction volume of 25 Using a liquid-based colorimetric assay in water, the estimated LoD was about 20 copies/μL with 4/4 replicates showing a change of color from red to yellow, therefore confirming that amplification occurred.

Example 6—Limit of Detection (LoD)

The LOD for a liquid-based LAMP reaction can be a concentration of about 20 copies of virus per μL of sample volume. For a solid-phase reaction medium (e.g., chromatography paper), each reaction area can hold a sample volume of about 25 μL.

Example 7—Validation of LoD

After determining that the LoD was about 20 copies/μL in saliva, the following samples with associated concentrations were created: (1) 20 copies/μL (1×LoD—10 samples), (2) 40 copies/μL (2×LoD—10 samples), (3) 100 copies/μL (2 samples), (4) 1000 copies/μL (2 samples), (5) 10,000 copies/μL (2 samples), (6) 100,000 copies/μL (2 samples), and (7) 1,000,000 copies/μL (2 samples). The negative samples were aliquots of pooled saliva (30 aliquots). The results were also confirmed using image processing.

Example 8—LoD, Sensitivity, and Specificity

Multiple serial dilutions of heat-inactivated SARS-CoV-2 in water were made (at a range of about 100 copies/reaction–$10^5$ copies/reaction). These serial dilutions were used as a template in liquid reactions to establish a baseline LoD for potential primer set candidates. Reactions were run in triplicate on a white qPCR plate (e.g., Thermo Scientific® AB-0800W) for each viral concentration and heated to 65° C. in a standard 75 L biological incubator (e.g., Fisherbrand® Isotemp Microbiological Indicator, 15-103-0513) for 60 minutes. The color of the reaction mixtures at different time points were recorded by scanning the plate on a tabletop scanner (Epson® Perfection V800 Photo Color). The LoD for a primer set was determined by the lowest viral concentration that resulted in a strong color change in all three replicates. Any candidate that was able to provide amplification at $10^3$ copies/reaction or lower was then subjected to the same procedure with virus dilutions (e.g., diluted by factors of 2×) and spiked into pooled, healthy saliva to check for matrix interference. Saliva LoD studies were then conducted on the paper-based device to check for primer compatibility on a paper substrate.

Figure 11:
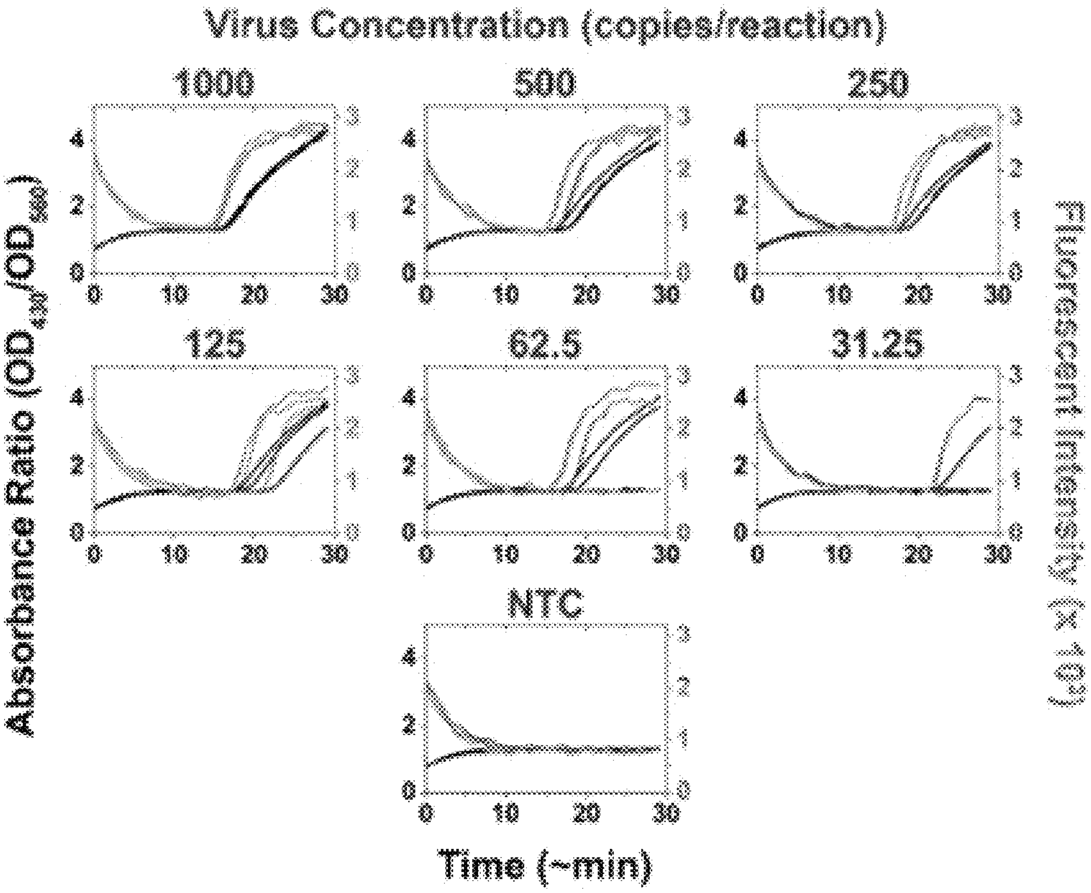
FIG. 11 shows a reaction in liquid using heat-inactivated SARS-CoV-2 spiked into water in accordance with an example embodiment.

As illustrated in FIG. 11, the reactions on the right were conducted in liquid using heat-inactivated SARS-CoV-2 spiked into water with a colorimetric mixture combined with a fluorescent dye using a reaction volume of 25 μL. The black lines indicated a color change as measured by the absorbance ratio ($OD_{430}/OD_{560}$) and the light blue lines indicated a fluorescent change as measured by the fluorescence intensity in units of $10^3$. The time of detection could be faster when used with a built-in color/fluorescence reader.

For a virus concentration of about 1000 copies/reaction, the absorbance ratio and fluorescent activity spikes after about 17 minutes. For a virus concentration of about 500 copies/reaction, the absorbance ratio and fluorescent activity spikes after about 18 minutes. For a virus concentration of about 250 copies/reaction, the absorbance ratio and fluorescent activity spikes after about 19 minutes. For a virus concentration of about 125 copies/reaction, the absorbance ratio and fluorescent activity spikes after about 18 minutes. For a virus concentration of about 62.5 copies/reaction, the absorbance ratio and fluorescent activity spikes after about 17 minutes. For a virus concentration of about 31.25 copies/reaction, the absorbance ratio and fluorescent activity spikes after about 22 minutes. For the no template control, the absorbance ratio and fluorescent activity never spikes as expected.

The sensitivity and specificity were determined using 30 contrived positive samples at varying multiples of the LoD (1×, 2×, 4×, 40×, and 400× with 10, 10, 4, 3, and 3 replicates, respectively) and 30 non-template control (NTC) negative saliva samples. The colorimetric response intensity was determined using ImageJ to extract the average green channel intensity of each reaction zone. A receiver-operating characteristic (ROC) curve was generated by varying the threshold cutoff between positive and negative reactions and calculating the sensitivity and specificity at each threshold value. The sensitivity was calculated as a ratio of the number of true positives to total positives, including false positives. The specificity was calculated as a ratio of true negatives to total negatives, including false negatives.

Multiplexing Selected Targets to Test for Viral Pathogens Using Paper LAMP

Example 9—Paper Strip Format

Figure 12:
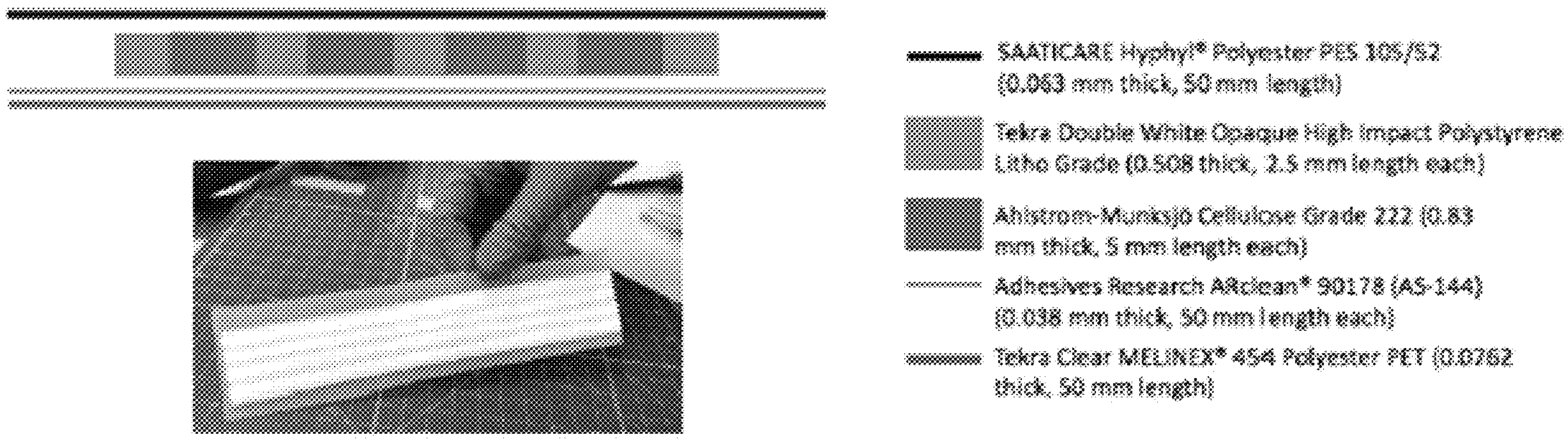
FIG. 12 illustrates a paper strip format in accordance with an example embodiment.

FIG. 12 illustrates a paper strip format. The black lines indicate SAATICARE Hyphyl® Polyester PES 105/52 having a thickness of 0.063 mm and a length of 50 mm. The red lines indicate Tekra Clear MELINEX® 454 Polyester PET having a thickness of 0.0762 and a length of 50 mm. The green lines indicate Adhesives Research ARclean® 90178 (AS-144) having a thickness of 0.038 mm and a length of 50 mm. The orange block indicates Tekra Double White Opaque High Impact Polystyrene Litho Grade having a thickness of 0.508 mm and a length of 2.5 mm. The blue block indicates Ahistrom-Munksjo Cellulose Grade 222 having a thickness of 0.83 mm and a length of 5 mm. In this example, the paper strip has 5 spacers (in orange) and 4 reaction layer sections (in blue), along with a spreading layer (in black), an adhesive layer (in green), and a substrate (in red).

Example 10—RT-LAMP Process

Figure 13:
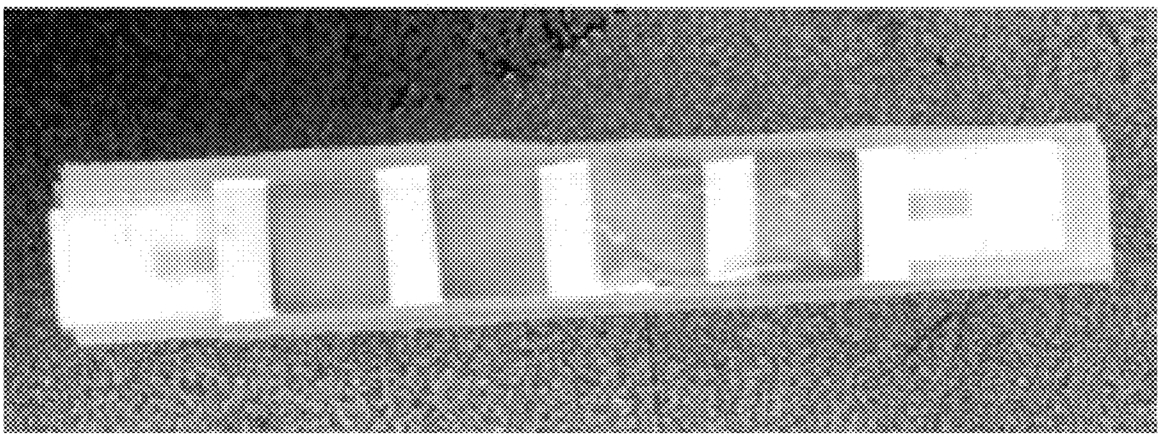
FIG. 13 illustrates a solid phase LAMP reaction medium in accordance with an example embodiment.

As illustrated in FIG. 13, a solid phase LAMP reaction medium can include: a 6 mm×50 mm clear 3 mm Melinex® 454 with Arclean® 90178; a reaction layer comprising 5 mm Ahlstrom 222 reagent material (including 4 discontinuous reaction layer sections in pink); spacers comprising 2.5 mm 20 mil polystyrene (including 5 discontinuous spacers), a spreading layer comprising Saaticare® PES 105/52 hyphyl, and a substrate comprising a capillary created with 14 mm Melinex, Arclean® 90178, and 3M 9962.

Figure 14:
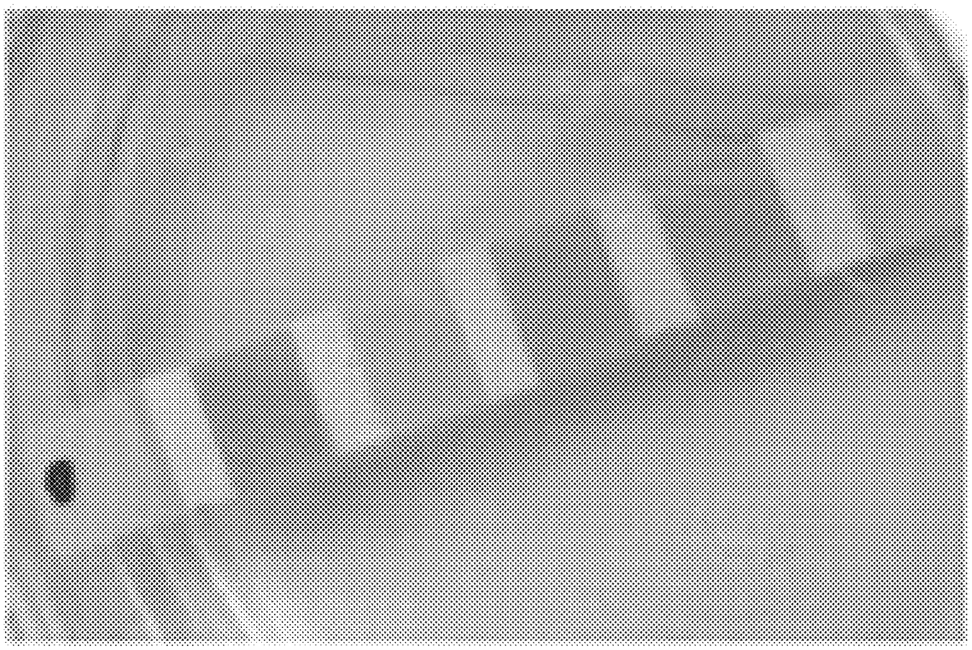
FIG. 14 illustrates a solid phase LAMP reaction medium in accordance with an example embodiment.

As illustrated in FIG. 14, cross talk between reaction zones can be avoided by having sufficient space between each reaction section or test area. In this example, the four reaction sections in orange remain free from cross-contamination because the 5 spacers are free of color changes.

Example 11-A—Paper Contrast

Figure 15A:
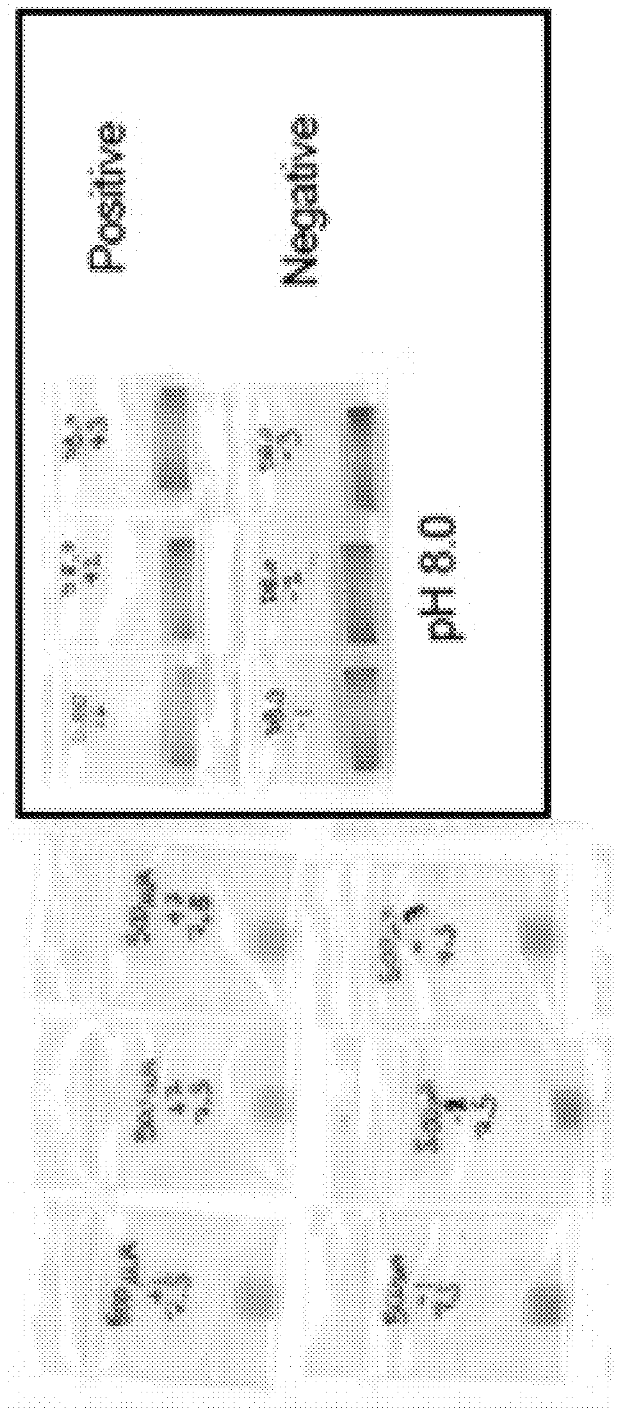
FIG. 15A illustrates a comparison between grade 1 chromatography paper and grade 222 chromatography paper in accordance with an example embodiment.

In another example, as illustrated in FIG. 15, grade 222 chromatography paper can provide greater contrast than grade 1 chromatography paper. The positive results for the 222 paper (on the left) show a greater contrast between the positive results on the top left (yellowish orange) and the negative results on the bottom left (dark orange) compared to the positive results for the on the top right (orange) and the negative results on the bottom right (dark orange). Each paper strip was tested with about 500 μM of buffer with a pH ranging from 8.0 for the negative test to 7.5 for the positive test.

Example 11-B—Effect of Phenol Red Concentration on Paper

To distinguish differences between negative results and positive results without inhibiting the reaction itself, phenol red concentration was tested on both Grade 1 and Grade 222 chromatography paper. For both types of chromatography paper, 250 μM of phenol red per reaction displayed a consistent result. Lower dye concentration demonstrated relatively faint and pale color after 60 min of incubation, whereas longer incubation time was used for higher concentration phenol red paper pads to differentiate positives from negatives.

Figure 15B:
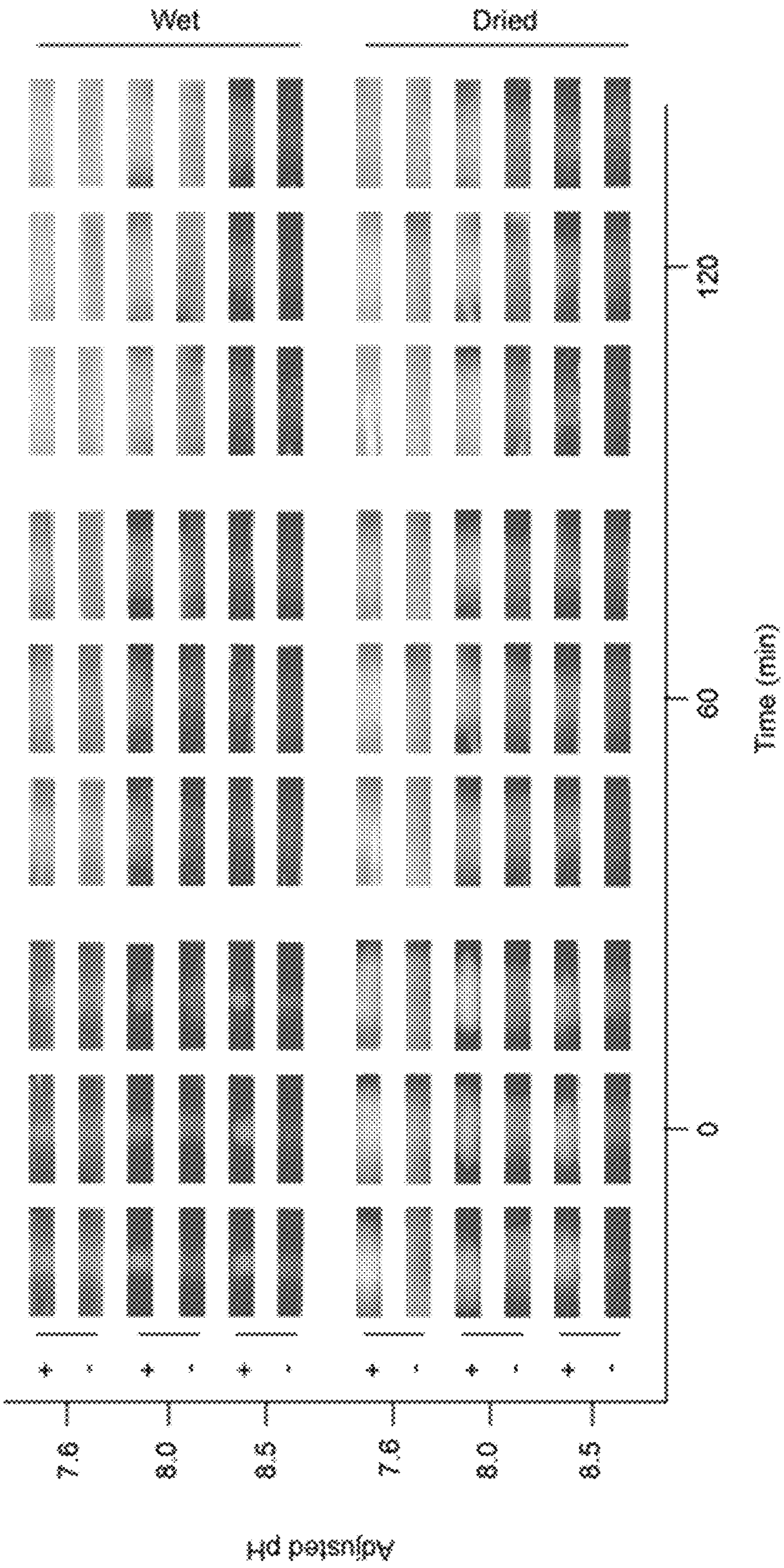
FIG. 15B illustrates RT-LAMP when incorporating drying at different starting pH of the RT-LAMP reaction mixture in accordance with an example embodiment.

Example 11-C—Effect of Initial pH and Drying on Colorimetric RT-LAMP Response on Paper Using Phenol Red FIG. 15B illustrates RT-LAMP when incorporating drying at different starting pH of the RT-LAMP reaction mixture. In this example, pH 7.6 is the unadjusted pH of the RT-LAMP reaction mixture. Wet setup indicated 5 μL of synthetic RNA (N gene, 0.2 ng/μL, '+') or water ('−') were added immediately after adding 20 μL of LAMP reaction master mix. Dried setup indicated paper strips were left to dry for 30 minutes at room temperature after applying 20 LAMP master mix and then rehydrated with 25 μL synthetic RNA ('+') or water ('−'). LAMP reactions contained 12.5 μL NEB 2× colorimetric master mix, 2.5 μL of primer mix, and 5 μL of phenol red prepared in nuclease-free water (1 mM). The pH of the resulting mix was adjusted with KOH. Grade 1 chromatography paper was used. Heating was carried out in an incubator set at 65° C. for 120 minutes and scanned with a flatbed scanner at time points of 45, 60, 90, and 120 minutes during the reaction.

Example 12—Test Strip Format

Figure 16:
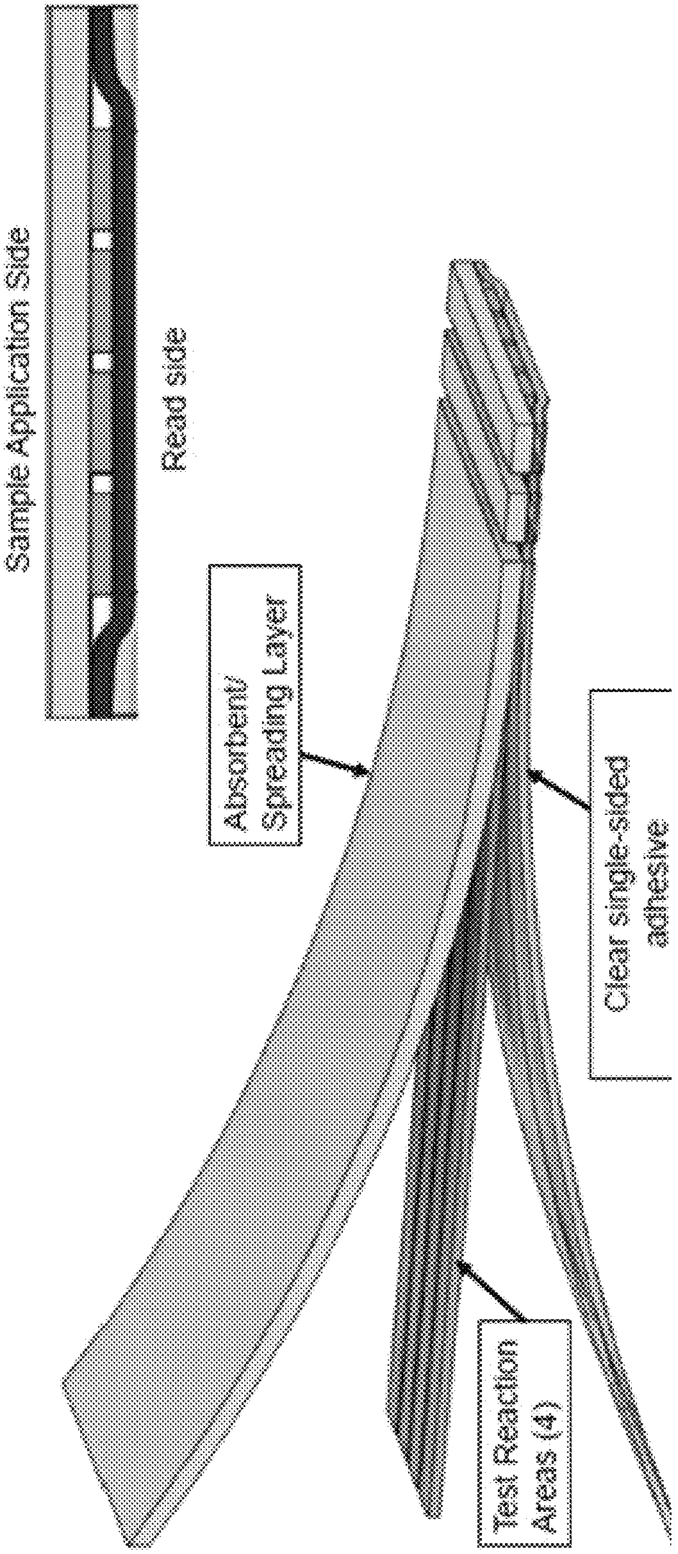
FIG. 16 illustrates a test strip format in accordance with an example embodiment.

As illustrated in FIG. 16, a test strip format has a sample application side and a read side (top right of the Figure). The sample can be applied to the sample application side in one position when the spreading layer is present. In other examples, without a spreading layer, the sample can be applied to the sample application layer over each section of the reaction layer (orange). The read side can be read without specialized instrumentation or with a colorimetric detector or fluorescent detector.

As further illustrated in FIG. 16, the test strip format also has 4 test reaction areas, an absorbent/spreading layer, and clear single-sided adhesive that will conform to shape and contact the absorbent layer.

Example 13—Test Strip Assembly Process

Figure 17:
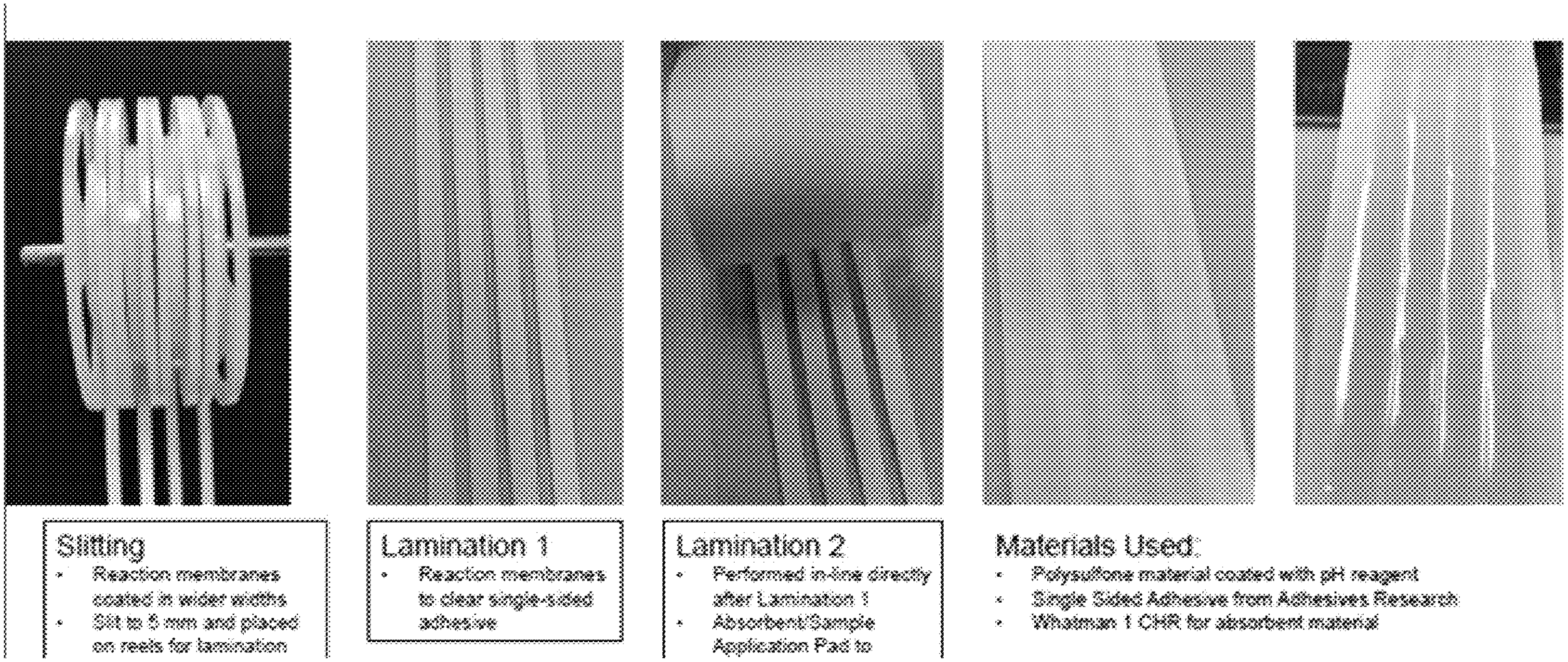
FIG. 17 illustrates a test strip assembly process in accordance with an example embodiment.

FIG. 17 illustrates a test strip assembly process including slitting in which the reaction layers are coated in wider widths and slit to 5 mm and placed on reels for lamination. The process also includes a first lamination process of reaction layers to clear single-sided adhesive. The process also includes a second lamination process that is performed in line directly after the first lamination process, and wherein the spreading layer is laminated to the reaction layer and the adhesive layer. The test strip assembly process can comprise materials including polysulfone material coated with pH reagent, a single-sided adhesive, and chromatography 1 paper.

Example 14—RT-LAMP Process

The RNA from the SARS-CoV-2 virus in saliva was extracted, reverse-transcribed, and amplified in a one-pot mixture by heating the saliva and reagent mixture at 65° C. The four primer sets used for LAMP include: one targeting the SARS-CoV-2 RdRp gene, one targeting the SARS-CoV-2 envelope gene (E), one targeting the SARS-CoV-2 ORF lab region, and finally one targeting the human RNaseP (RP) gene which serves as an on-board control. Each primer set was comprised of 6 individual primers, targeting specific regions of viral or human RNA which are reverse-transcribed and amplified during isothermal incubation using a reverse transcriptase and a strand-displacing polymerase.

Example 15—Positive Control

A positive control reaction is included on-board the test device as one of the test regions which is run together with the three test strips for viral RNA. The positive control simultaneously serves as a positive template control and extraction control. If a red-to-yellow color change occurs on the control region of the test strip, this indicates that viral RNA, if it were present in the specimen, has been successfully extracted from the virus, and that the reagents in the test are all performing as expected in order to produce an amplification signal. If the color change does not occur, then the test should be considered invalid and repeated.

The positive control detects human RNase P, a ubiquitous marker in human clinical specimens and a standard control in many RT-PCR kits. Amplification of this marker indicates that lysis of human cells has successfully occurred under the test conditions, and that viral lysis can also be inferred.

The scientific basis of the control is as follows. Unlike assays based on RT-PCR, our assay does not use chemical extraction of viral RNA; rather heat treatment was sufficient. Polymerases in RT-PCR are sensitive to reaction inhibitors in biological sample matrices. Thus, these tests usually have an RNA extraction and purification operation. In contrast, the Bst 2.0 polymerase enzyme used in LAMP assays is extremely robust in biological matrices, so extraction and purification are not used. The 65° C. temperatures achieved in the instrument are sufficient to lyse virus particles, expose viral RNA, and support robust amplification.

Example 16—Negative Control

A negative, no template control test is performed by using the test device with a blank test solution in lieu of a saliva specimen. The blank test solution is a sterile, pH-buffered solution without any RNA or DNA template. If a color change were observed in this test, it would suggest a likelihood of false positives and therefore invalidate any positive results obtained since the last control was run. Therefore, instructions to the user will have the user site perform this negative control upon receipt of the test kits using one such representative test kit. This confirmation can also be repeated at a defined interval.

The most likely cause of false positives in a negative control is carryover of amplified DNA product from sequential tests. The negative-control test is the last in a line of control measures to prevent false-positives due to carryover contamination, including manufacturing controls of cartridges with tight seal tolerances and routine disinfecting wipe-cleaning of the heater apparatus by the operator.

Example 17—Internal Control

The test assembly employs a unique control designed for the use of saliva as the test substrate. Each test strip includes pH indicator dye which serves as an internal control that validates that the initial pH of the saliva specimen is within the expected range. If a color change from red to yellow is observed on all four test strips when the sample is applied (prior to heating), then the user should conclude that the specimen is invalid and not proceed with the test. External factors such as eating, drinking, or use of oral hygiene products prior to sampling can skew the initial pH of the specimen. In the presence of a failed pH indicator, if the operator determines that one of these factors has affected the specimen, then a re-test can be performed after allowing 5 minutes for the patient's saliva pH to return to their normal state. Other external factors such as some forms of illness can also systemically affect saliva pH, in which case use of an alternative testing means is indicated.

Example 18—Result Confirmation

The Paper LAMP test is a qualitative test. The test is a color-based visual result that can be read by the operator with the aid of an interpretative color chart. A positive reaction result yields a yellow color. All test controls should be examined prior to interpretation of patient results. If the controls are not valid, the test is invalid and patient results cannot be interpreted.

Since this is an isothermal RNA amplification, the presence of the target SARS CoV-2 RNA at levels defined by the LoD experiments will produce results indicative of a positive test. In some cases, a positive test interpretation may be confirmed by a positive result in 2 of the 3 target gene primer regions of Orflab, E Gene or RdRp Gene. The color of the test strip can be compared to a supplied color interpretation chart to identify positive results. The RNaseP region of the test strip should turn yellow to indicate a valid test. If that region does not turn yellow the test is invalid and should be repeated.

The first indicator of a reliable and legitimate test strip is the confirmation that the 4 test strip regions do not turn yellow upon application of the saliva before heating of the test strip. If this occurs the saliva pH is outside an acceptable range likely due to recent food or fluid intake. The patient should rinse their mouth with water, wait at least 5 minutes, and re-sample the saliva.

Once the test reaction is completed in the heater apparatus, the on-board control should show a positive yellow color change in the RNaseP region. Once that has been confirmed then each strip region should be examined for color change versus the supplied color interpretative chart. Each strip region is classified as positive (e.g., a yellow change) or negative (e.g., pink color). In one example, a confirmation of SARS CoV-2 can be indicated when 2 of the test regions are positive.

Example 19—Sources of False Positives

False positives can often occur in RT-LAMP assays if proper care is not taken to address them in assay procedure.

Sources of these false positives can stem from DNA aerosols formed by previous RT-LAMP reactions that remain in the environment for extended periods of time and that contaminate future experiments. These aerosols can either contaminate individual reagents during reaction prep or contaminate reaction mixtures when they are being transported, handled, loaded with samples, or incubated. Aside from reducing the accuracy of RT-LAMP related tests, aerosols can add noise to experiments that use specific concentrations of template, such as LoD studies. To address these various points of contamination, all RT-LAMP related procedures can be separated into stages (i.e. reaction preparation, transport, loading/sealing, incubation for amplification, and gel electrophoresis) to be performed in different locations. By spatially separating operations in the protocol, the likelihood of aerosols being introduced before reaction sealing can be minimized or troubleshooted if false positives occur.

Example 20—Screening of Plates, Caps, Sealers, and Tubes

Given that RT-LAMP is prone to contamination and therefore, false positives, extensive screening was conducted on qPCR 96-well plates, sealing methods, and PCR tubes. We first screened Thermo Scientific® 96-well Full Skirted PCR Plates, both Clear (ThermoScientific® AB-0800) and White (AB-0800W), along with FrameStar 96-well skirted optical bottom plates (Brooks Life Sciences® 4TI-0970). The clear plates were primarily used to aid in the scanning of colorimetric assays. Of these clear plates, the white bottomed Thermo Scientific® 96-well Full Skirted PCR plates had the best performance based on the average number of false positives.

Figure 22A:
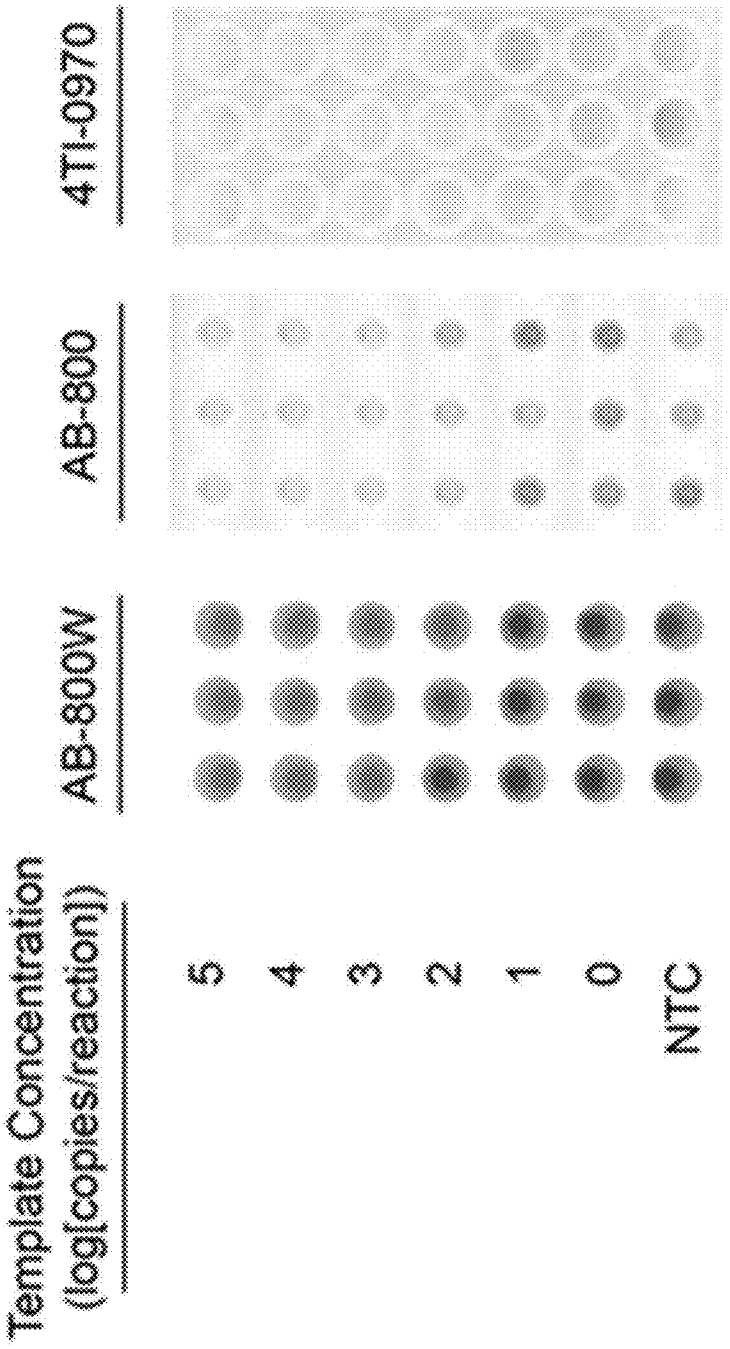
FIG. 22A illustrates the effect of plate on RT-LAMP colorimetric response in accordance with an example embodiment.

FIG. 22A shows colorimetric RT-LAMP scan images for the limit of detection (LoD) of orflab.II. Titles of scans are catalog numbers that correspond to different plate types that were used to run colorimetric LoD. Yellow wells indicate a successful LAMP reaction taking place whereas red/orange wells indicate absent or low-level amplifications respectively. 20 μL reaction mixtures were spiked with 5 μL of heat-inactivated virus dilutions in water at the labeled concentrations. Reaction master mixes consisted of 12.5 μL of NEB Colorimetric 2× master mix, 2.5 μL of primer mix, and 5 μL of water. Endpoint images were taken after heating in an incubator set at 65° C. for 60 minutes. Three replicates for each viral concentration were run per primer set.

For sealing methods, we investigated the following products: MicroAmp® Optical 8-cap strips (Thermo Fisher® 43-230-32), Thermo Scientific VersiCap Mat Cap Strip (Thermo Fisher® AB1820), Thermo Scientific Adhesive Plate Seals (Thermo Fisher® AB-0558), and MicroAmp Optical Adhesive Seal (Thermo Fisher® 43-119-71). Of the caps, the VersiCap Mat Cap Strip sealed the best when observing the false positive rate; however, for colorimetric scans, the caps made it difficult to get accurate images of the reaction progress because they are not entirely transparent. As a result, adhesive seals were tested, and they both performed equally in comparison to each other. Additionally, when pressure was applied simultaneously and evenly across the plate, the adhesive seals performed better than the VersiCaps based on false positive rates.

Figure 22B:
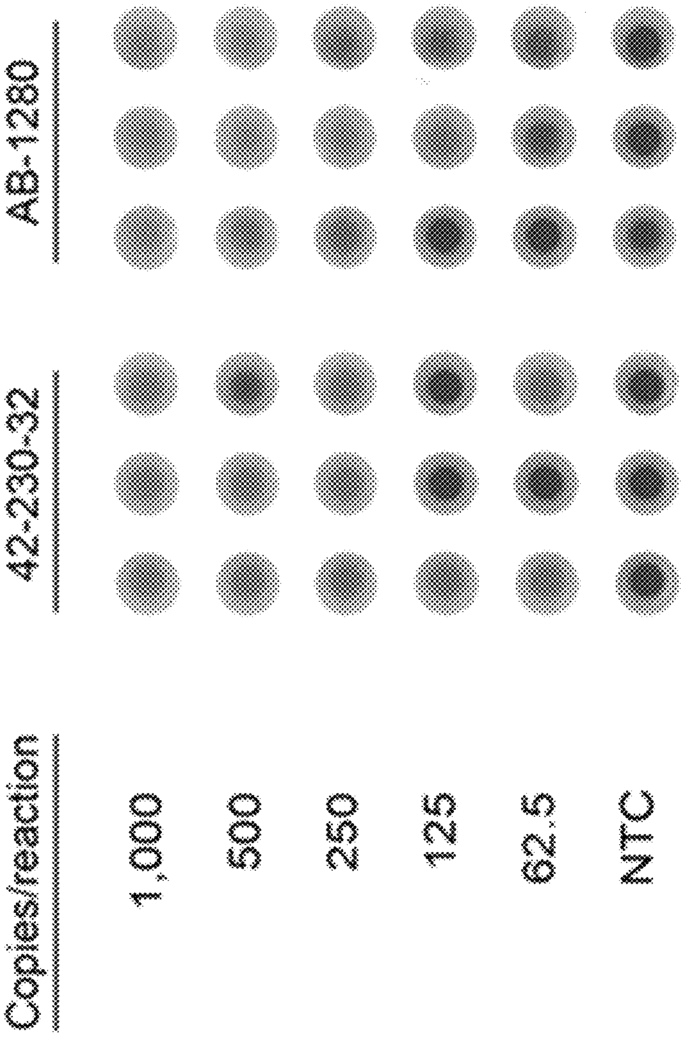
FIG. 22B illustrates the effect of caps on RT-LAMP colorimetric response in accordance with an example embodiment.

FIG. 22B shows colorimetric RT-LAMP scan images for limit of detection (LoD) of orflab.II. Titles of scans are catalog numbers that correspond to different cap types that were used to run colorimetric LoD. Yellow wells indicate a successful LAMP reaction taking place whereas red/orange wells indicate absent or low-level amplifications, respectively. 20 reaction mixtures were spiked with 5 μL of heat-inactivated virus dilutions in water to result in the final labeled concentrations (positive reactions) or nuclease-free water (negative). Reaction master mixes included 12.5 μL of NEB Colorimetric 2× master mix, 2.5 μL of primer mix, and 5 of water. Endpoint images were taken after incubating the plate at 65° C. for 60 minutes. Three replicates for each viral concentration were run per primer set.

As an alternative to plates during imaging, we investigated the following PCR tube products: MicroAmp™ Optical 8-Tube Strip with Attached Optical Caps (Thermo Fisher® A30588) and MicroAmp™ Optical 8-Tube Strip (Thermo Fisher® 4316567) using the same caps as those used to seal the plates. The tubes with the attached optical caps performed the best with regards to false-positive rate.

A fully assembled, 4-plex test strip can include a spreading mesh, adhesive, and see-through Melinexbacker. The test strip can also include a DNA template in water at a concentration of 0.2 ng/uL which corresponds to about $10^8$ copies/uL. The sample volume can be 100 uL. An N-gene primer can be used with alternating conditions of primers and no-primers. The adhesive might have a buffering effect that inhibits color response so the formulation should be to compensate.

Paper LAMP Testing Process and Methodology

Example 21-A—Paper LAMP Test Process

Figure 18A:
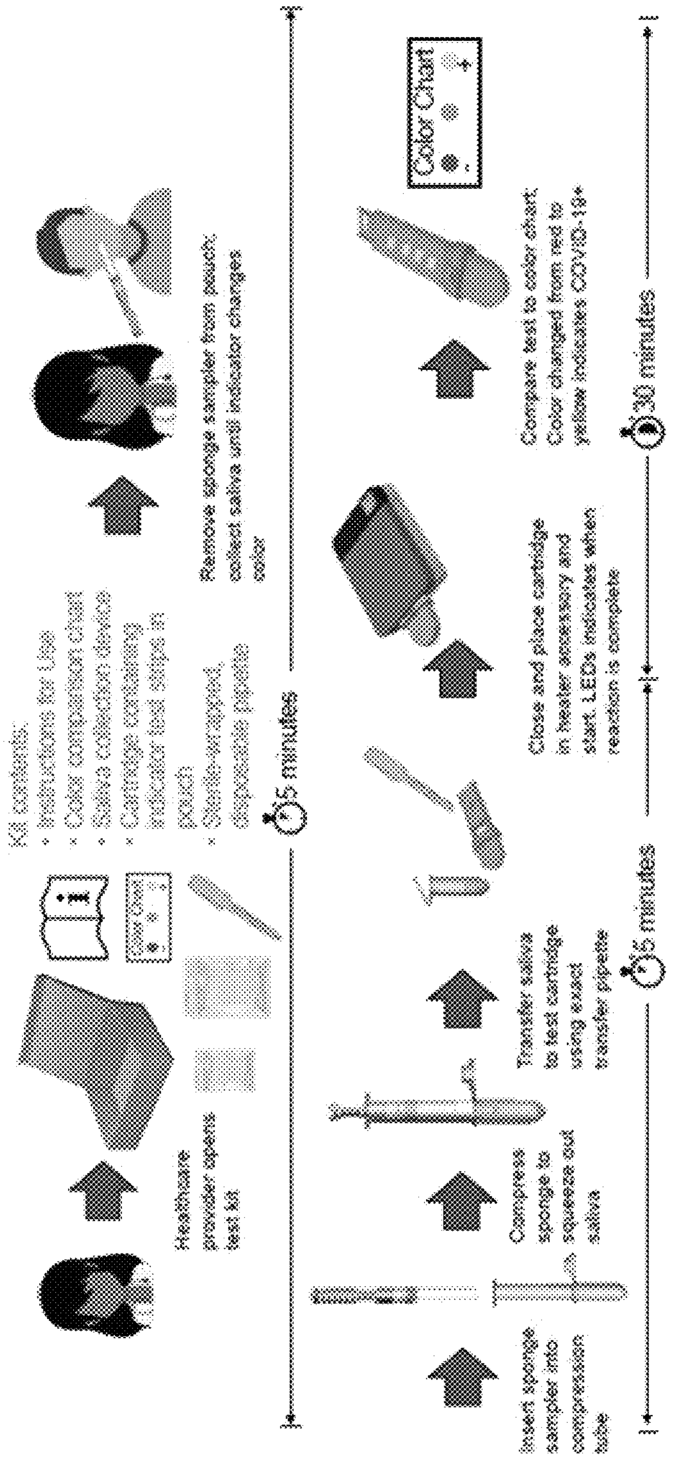
FIG. 18A illustrates operations for a biological testing system in accordance with an example embodiment.

The Paper LAMP test is designed for simple point of care use by trained healthcare professionals. The entire testing process is described in FIG. 18. The patient collects a saliva specimen under the guidance of the healthcare professional. The saliva sample is collected into a specialized collection vessel which contains no additives and is thus safe for the patient to use in the collection. The volume of saliva is approximately 100 μL, which is easily collected by the patient. The test strip which contains the specific RNA detection regions as noted above is entirely contained in a plastic strip holder. After collection of the saliva sample the patient hands the collection vessel to the operator. The operator then applies the saliva sample to the test strip at the indicated locations and closes the cartridge housing. The cartridge with the strip which contains the sample is then placed in the heater apparatus which is designed to securely hold the cartridge in place to achieve the desired heating to 65° C. The Paper LAMP assay proceeds on the test strip at an isothermal temperature. During the LAMP reaction, the nucleic acids are identified in the saliva sample and, under a temperature of 65° C., the resulting change of pH from the amplification of nucleic acids causes a color change on the strip.

The heater apparatus is designed to provide uniform heating across the test strip. The heating apparatus can have (red-yellow-green) colored LED lights to show the user the progress of the heating in terms of time of incubation and alert the operator when the test has reached conclusion. While the test is progressing the heater apparatus can contain a feature, e.g., a magnetic or mechanical lock to ensure the test is not interrupted. The test reaction can proceed for approximately 15 to 30 minutes at the isothermal 65° C. temperature. At the conclusion of the assay, the test carrier with the test strip contained therein can be removed from the heater and visually read.

Example 21-B—Paper LAMP Test Process

Figure 18B:
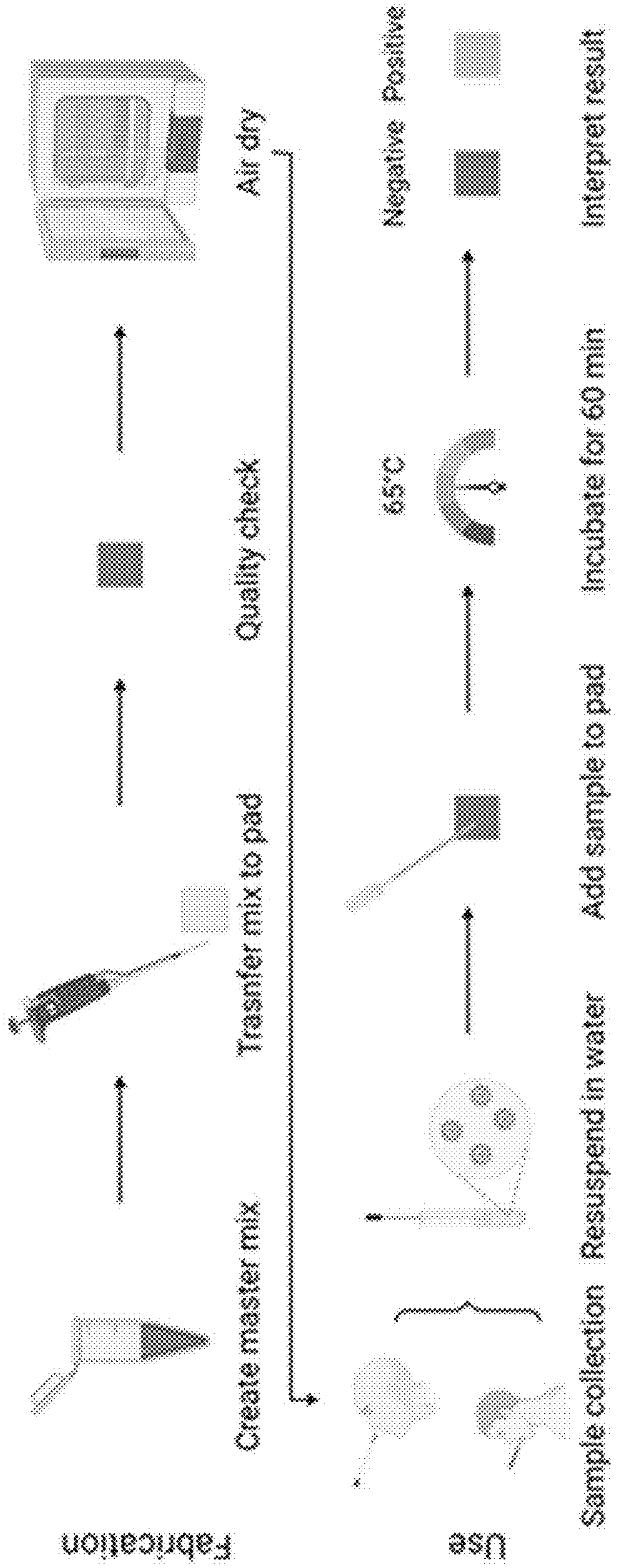
FIG. 18B illustrates operations for a biological testing system in accordance with an example embodiment.

FIG. 18B illustrates fabrication and use of a paper-based colorimetric molecular test for SARS-CoV-2. The fabrication of the paper-based colorimetric molecular test for SARS-CoV-2 includes: (1a) Creating a master mix, (1b) transferring the mix to a pad, (1c) performing a quality check, and (1d) air drying the test device. The use of the paper-based colorimetric molecular test for SARS-CoV-2 includes: (2a) sample collection, (2b) resuspension in water, (2c) adding the sample to the pad, (2d) incubation for about 60 minutes at 65° C., and (2e) interpreting the results.

Example 21-C—Paper LAMP Test Process

The workflow of the assay is illustrated in FIG. 19A: collect saliva, transfer sample to paper-based device, incubate at 65° C., and read a result; a typical result is shown in FIG. 19D. FIG. 19C provides a schematic of our paper device's structure. The paper device included several Grade 222 cellulose reaction pads separated by 20 mil polystyrene spacers to prevent crosstalk between reaction zones. These components were attached to a transparent backing for structural support via a double-sided adhesive. Reagents to conduct RT-LAMP were dried onto the reaction pad during fabrication. These reagents were rehydrated when the user added the sample to the reaction zones.

FIG. 19 illustrates schematics and colorimetric characterization of the paper-based device. FIG. 19A provides a schematic illustration of the workflow for device use. The control zone indicates the no-primer control. FIG. 19B provides colorimetric LoD on paper using heat-inactivated severe acute respiratory syndrome coronavirus 2 (SARS-CoV-2) at the indicated concentration in 5% saliva. The negative replicates are RT-LAMP reactions using nuclease-free water in lieu of heat-inactivated SARS-CoV-2. Data was taken from FIG. 21A.

FIG. 19C provides a schematic layout of the paper device. FIG. 19D provides typical colorimetric results of a negative and positive run. Controls are RT-LAMP reactions without LAMP primers included. Positive reactions have 800 copies/μL spiked into 5% saliva. FIG. 19E provides a color gradient of possible results derived from the colorimetric results of panel B. FIG. 19F provides a summary table of observations used to calculate the analytical sensitivity and specificity of the paper device based on survey responses.

Each operation of the assay (FIG. 19A) was designed to reduce complexity and mitigate user errors in point-of-care settings. The sample collection operation uses a sponge-based collection device which allows for self-collection by the patient, removes particulates from the collected saliva, and minimizes variance in results from patient to patient. The transfer operation involved placing 25 μL of diluted saliva onto each of the two reaction zones on the device. For the incubation operation, the paper device with the sample loaded is sealed in a resealable plastic bag and placed in an incubator set at 65° C. for 60 minutes. Finally, for the read operation, the user compared the color of the control and reaction zones to the color bar in FIG. 19C to determine if the results are valid and if the pathogen of interest is present.

The platform comprises three main components: primer sets imposing specificity to the assay, a paper device containing two reaction zones (one control and one reaction), and a heating source used to heat the paper device to reaction temperatures. The primer sets determine what pathogen the assay targets. Therefore, the platform can be reconfigured to target a different pathogen by redesigning the primer sets while keeping all other aspects of the device and formulation the same. Additionally, the paper-based device can be configured to accommodate numerous reaction zones allowing for multiple targets to be detected simultaneously.

The direct detection of SARS-CoV-2 in saliva is shown via a distinct colorimetric response that can be read using the naked eye (FIG. 19). This format is amenable to roll-to-roll fabrication and is anticipated to cost —$10/test. The limit of detection (LoD) of the test is 200 copies/μL saliva. The analytical sensitivity (positive predictive value) is 76%, the specificity (negative predictive value) is 100%, and the accuracy is approximately 91% as determined using contrived samples (freshly collected saliva spiked with heat-inactivated SARS-CoV-2) when evaluated visually (FIG. 19F). Due to subjectivity in color perception of the control pad, respondents incorrectly identified a total of 20 out of the 80 devices presented as invalid, resulting in a false invalid rate of 25%. The sensitivity increases to 97% with an accuracy of 98% when the color change is quantified using image processing (FIG. 19C).

The device (FIG. 19C) had dimensions of 6 mm×20 mm and included: a reading layer, two reaction strips, and spacers to prevent crosstalk. The reading area included an optically clear 3 mil MELINEX (Tekra MELINEX® 454 Polyester (PET)) backer for support. This was attached to two reaction strips of 5 mm×6 mm chromatography paper (Ahlstrom-Munksjo Grade 222) using a double-sided adhesive (Adhesives Research acid-free ARclean® 90178). The strips were separated by 2.5×6 mm 20 mil polystyrene spacers (Tekra Double White Opaque High Impact Polystyrene (HIPS) Litho Grade). 25 μL of sample was added to saturate the strips when rehydrating.

A color bar was created by averaging RGB values of phenol red on Grade 222 chromatography paper over a range of pH values. A linear gradient was created using these average RGB values and the optimal threshold value determined from the ROC curve was annotated on the color bar (FIG. 19 C).

After loading the sample onto the paper-based device, the device was placed into a 1"×1" re-sealable plastic bag to prevent contamination during the RT-LAMP reaction. The plastic bag containing the paper device was then placed into an incubator at 65° C. for 60 minutes. The bag was removed, scanned with a flatbed scanner (FIG. 19D), and compared against a color chart (FIG. 19E) created by averaging RGB values from the phenol red response on grade 222 pads in buffers at known pH values from 6-9 (FIG. 21B). The threshold value in the color chart corresponds to the threshold determined from ROC analysis (FIG. 19B).

Figure 21A:
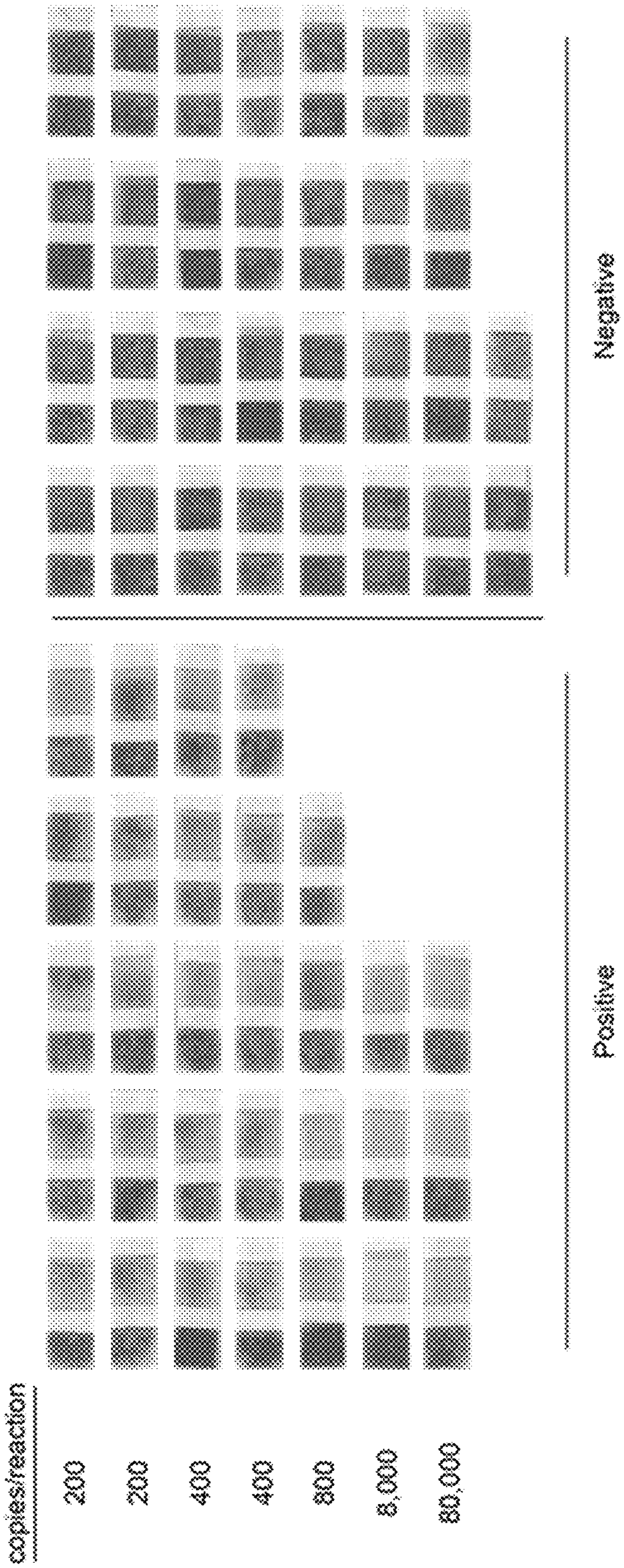
FIG. 21A illustrates validation of a device at various concentrations of heat-Inactivated SARS-CoV-2 in accordance with an example embodiment.
Figure 21B:
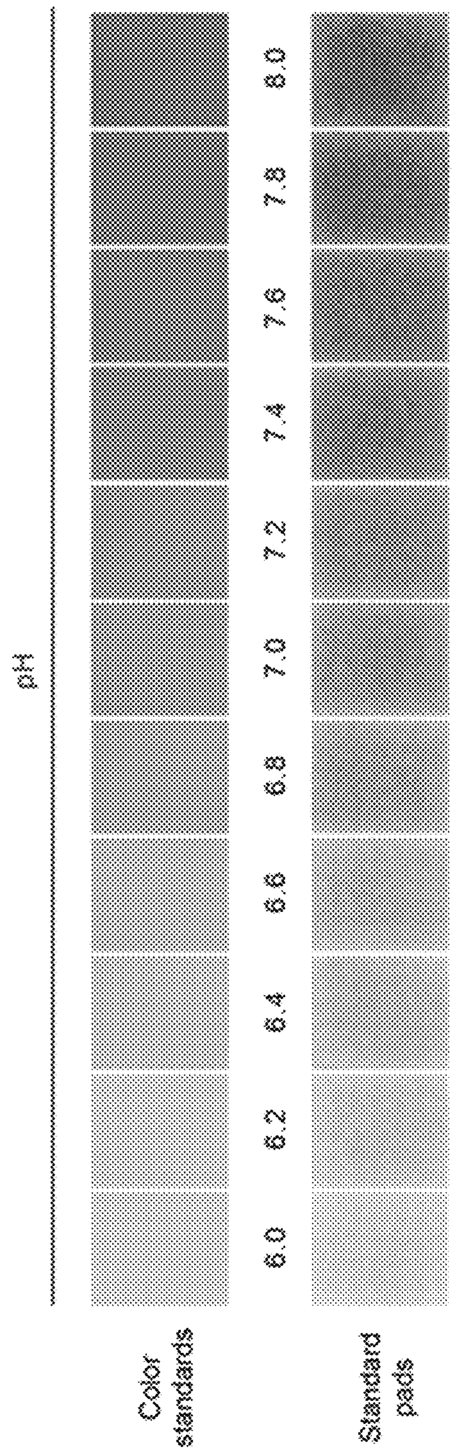
FIG. 21B illustrates phenol red color calibration at various pH values in accordance with an example embodiment.
Figure 21C:
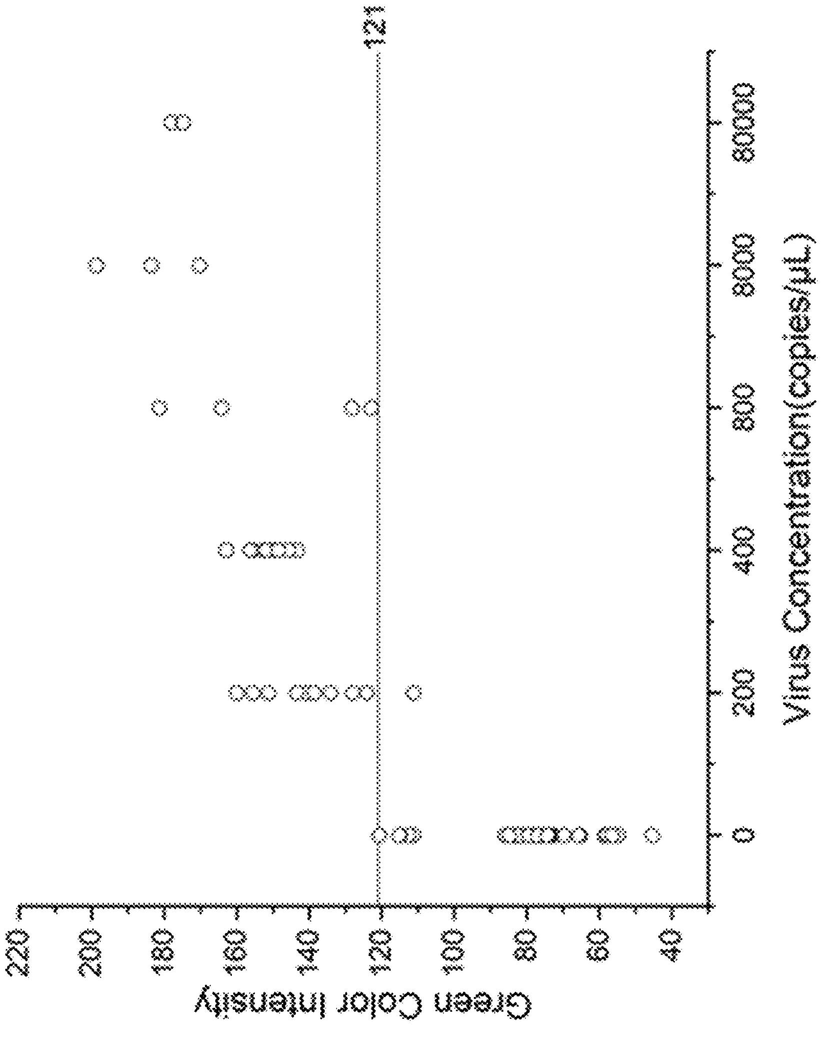
FIG. 21C illustrates green channel color intensity of RT-LAMP colorimetric response at varying template concentrations in accordance with an example embodiment.

After determining an LoD of 200 copies/μL in saliva (FIG. 19B), contrived samples of 1×, 2×, 4×, 40×, and 400× LoD were created. 30 aliquots of freshly collected saliva were used as negative samples (FIG. 21A). The results were quantified using image processing (FIG. 19A and FIG. 21C). A Difference between the green channel intensity of the negative and positive colorimetric reaction pads was found to be significant ($p<0.001$) using a two-tailed student's t-test.

Figure 20A:
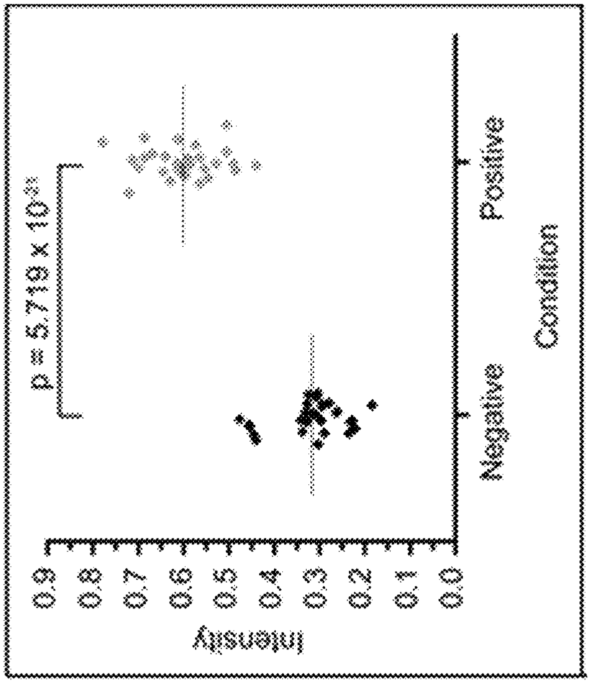
FIG. 20A-20C illustrate digital analysis of colorimetric responses on paper in accordance with an example embodiment.
Figure 20B:
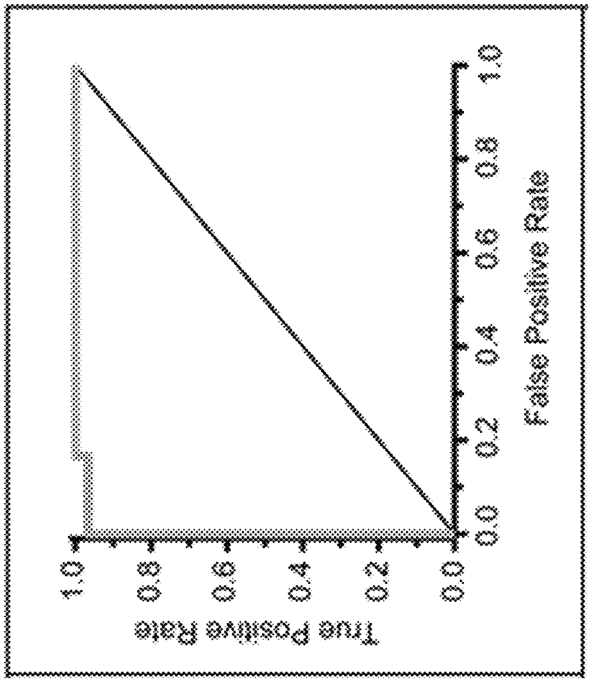
Figure 20C:
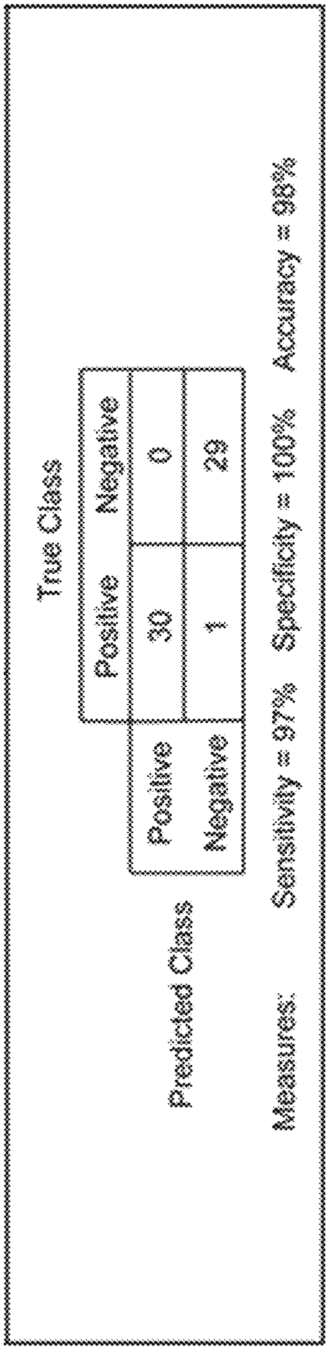

The specificity using image analysis was 100%, the sensitivity was 97%, and the accuracy was 98% (FIG. 20C). FIG. 20 illustrates digital analysis of colorimetric responses on paper. FIG. 20A shows a box plot for the green channel intensity of 30 positive and 30 negative results of RT-LAMP on paper. FIG. 20B shows a receiver-operator (ROC) curve for 30 positive and 30 negative results of RT-LAMP on paper. FIG. 20C shows a summary table for the observations based on image analysis.

Figure 23A:
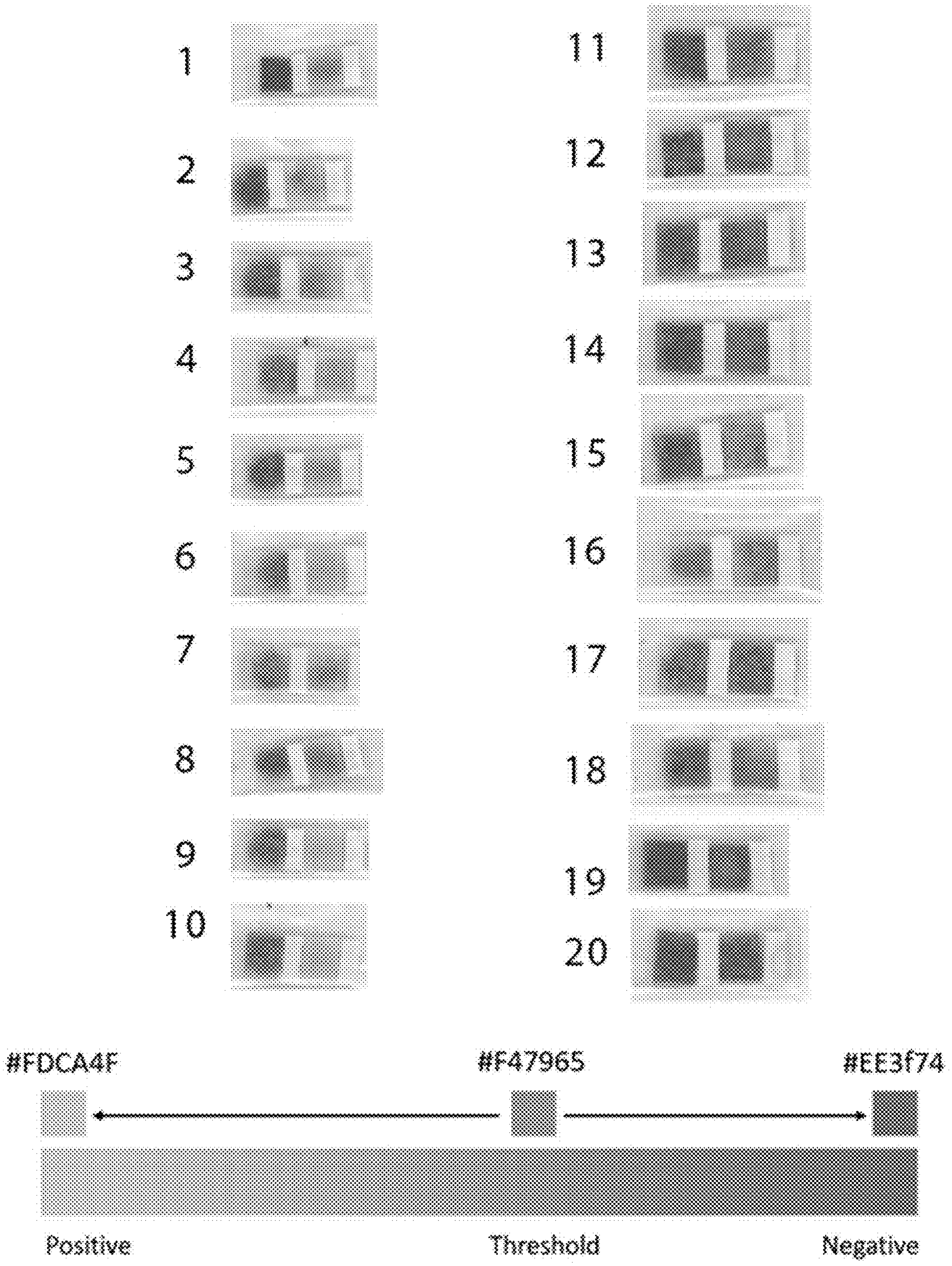

Colorimetric perception surveys (FIGS. 23A and 23B) were collected from participants enrolled in the study in accordance with Purdue University IRB Protocol #IRB-2021-375. Participants were given a color bar with a threshold annotated (FIG. 19E). Participants were given multiple paper device scans and were asked to classify the control pad (left reaction zone) as valid or invalid and the SARS-CoV-2 reaction (right reaction zone) as positive or negative. Observations classified as invalid were discarded from assay performance analysis and the proportion of incorrectly identified invalid assays was reported as the false invalid rate.

Four participants were asked to classify 10 positive and 10 negative reactions presented in FIG. 21A as valid or invalid (according to the left control zone) and positive or negative for SARS-CoV-2 (according to the right reaction zone) using a color bar (FIG. 19). Observations deemed invalid by the participants were discarded. Of the 40 true positive observations (all valid using image analysis), participants incorrectly classified 19 as invalid. This contrasts with the 40 true negative observations (36 of which were valid using image analysis) where 1 observation was incorrectly classified as invalid. Thus, the calculated specificity and sensitivity of our device while accounting for colorimetric interpretation were 100% and 76%, respectively, with an accuracy of 91% (FIG. 19F) and a false invalid rate of 25%.

Example 22—Sample Stability

The standard time from saliva collection to test strip application is within 2 hours. Sample stability with an allowance for testing for up to 24 hours from the sample collection can be based on repeat testing of samples (e.g., 15 positives and 15 negatives) at 0-2 hours, 8-12 hours, and 20-24 hours. Samples collected from patients in a rapid manner in a collection center or clinic setting can then be tested hours later. Collection at one site (e.g., in an outpatient facility or in a drive-thru collection area with subsequent transport of the saliva specimen to second location such as a location) can also be evaluated.

Example 23—Manufacturing

Dip coating and drying at elevated temperatures did not appear to negatively impact the LAMP reaction. This has positive implications for manufacturing throughput and scalability. The test strip was designed so that it can be manufactured at scale on existing converting equipment without significant tooling costs. The design is simple enough to meet the goal of a fast and simple path from prototyping to full-scale production to meet the emerging market needs.

Example 24—Design of Paper-Based Device

Figure 21D:
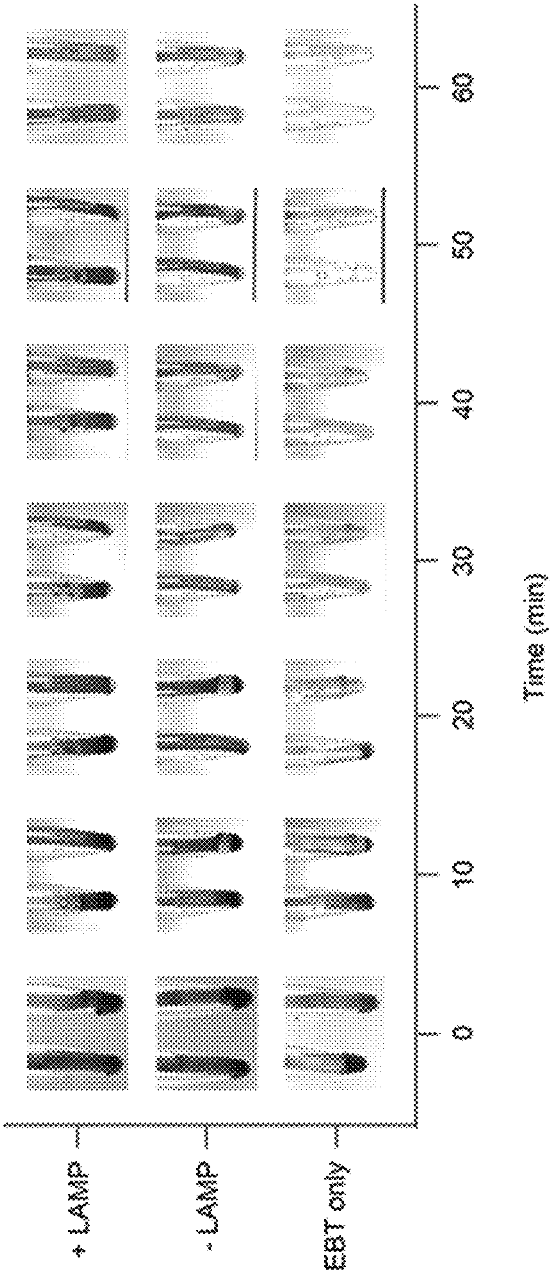
FIG. 21D illustrates LAMP on chromatography paper using EBT as a colorimetric reporter in accordance with an example embodiment.
Figure 21E:
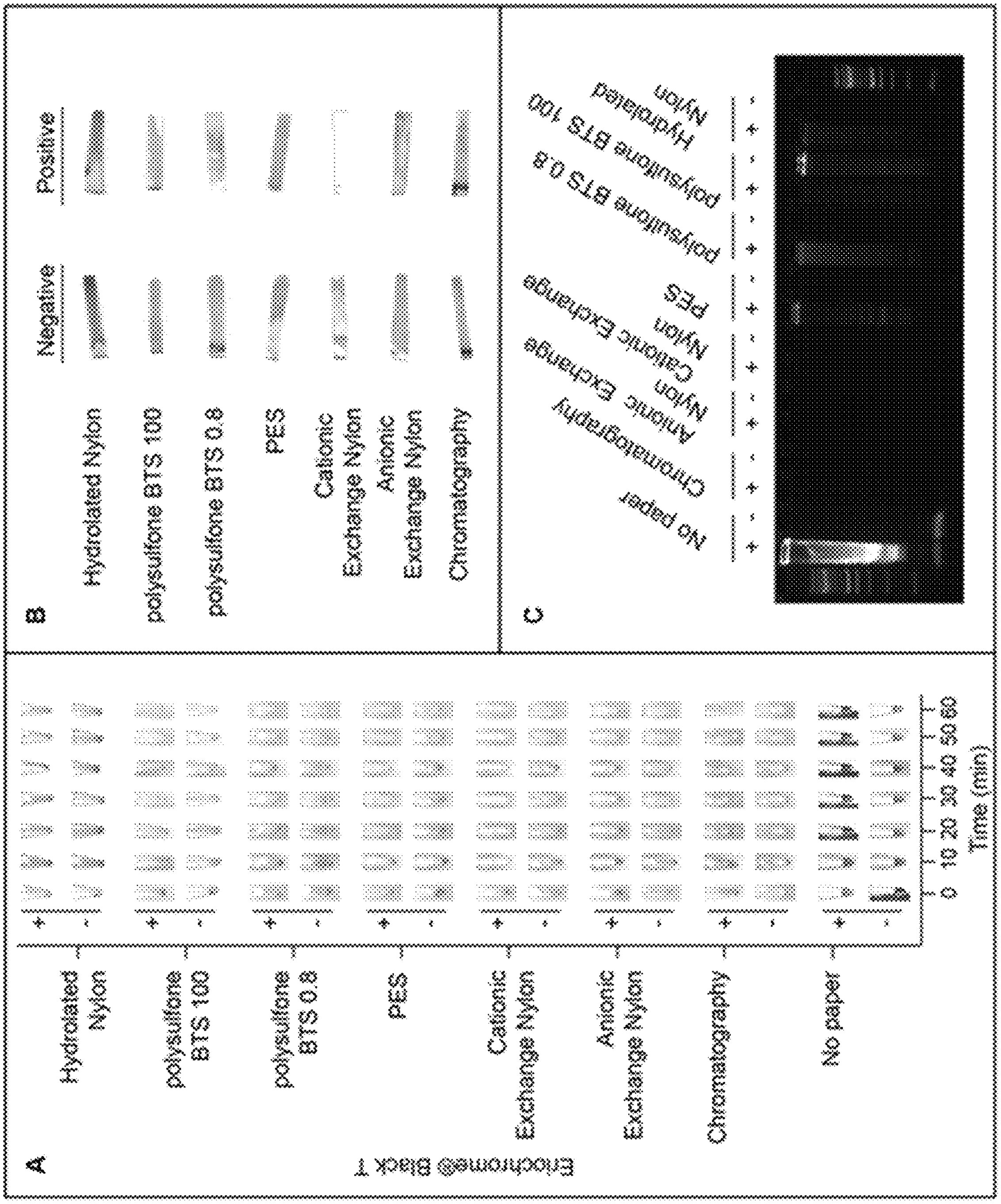
FIG. 21E illustrates the colorimetric response of LAMP on various papers using EBT as an indicator in accordance with an example embodiment.
Figure 21F:
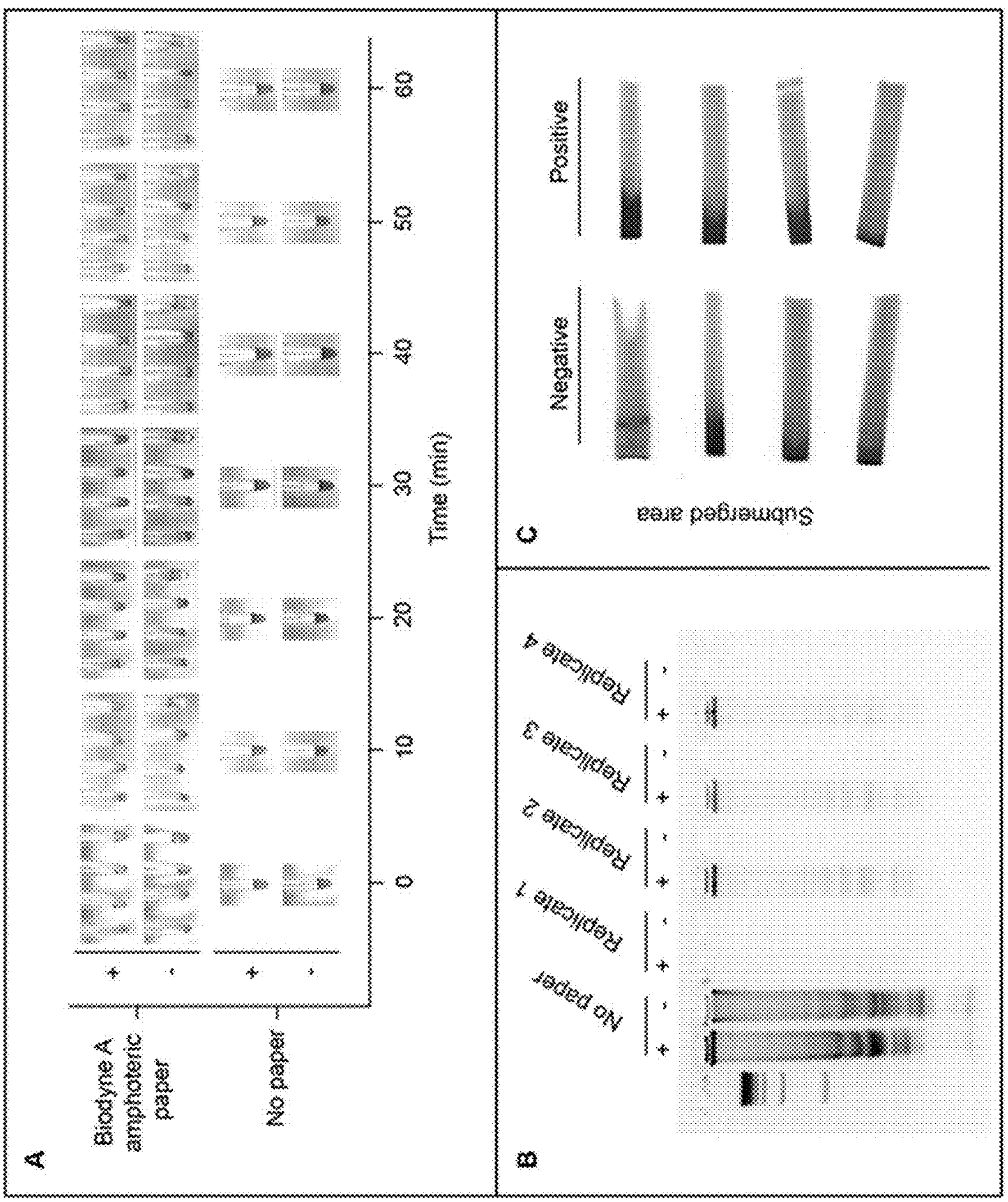
FIG. 21F illustrates LAMP detection on biodyne A amphoteric paper using EBT as a colorimetric indicator in accordance with an example embodiment.

Paper is widely used in pH indicators and urine strips primarily due to the inexpensive cost, low technical complexity, and ease of production using roll-to-roll manufacturing. For the devices disclosed herein, the use of several types of papers and selected chromatography paper was evaluated (FIGS. 21D-21F). Chromatography paper can be used in paper-based biosensors due to its improved wicking ability compared to other papers. Many paper-based devices use Grade 1 chromatography paper; however, due to the large area (5 mm×20 mm) of the Grade 1 chromatography paper, the distribution of solution across the paper was uneven. Thus, a different type of chromatography paper was selected, Grade 222 (0.83 mm), which is approximately 4.6 times thicker than Grade 1 (0.18 mm). Due to its increased thickness, the same volume of liquid can be loaded onto a 70% smaller reaction area by reducing the size of the device (5 mm×6 mm), allowing for even distribution.

Figure 21G:
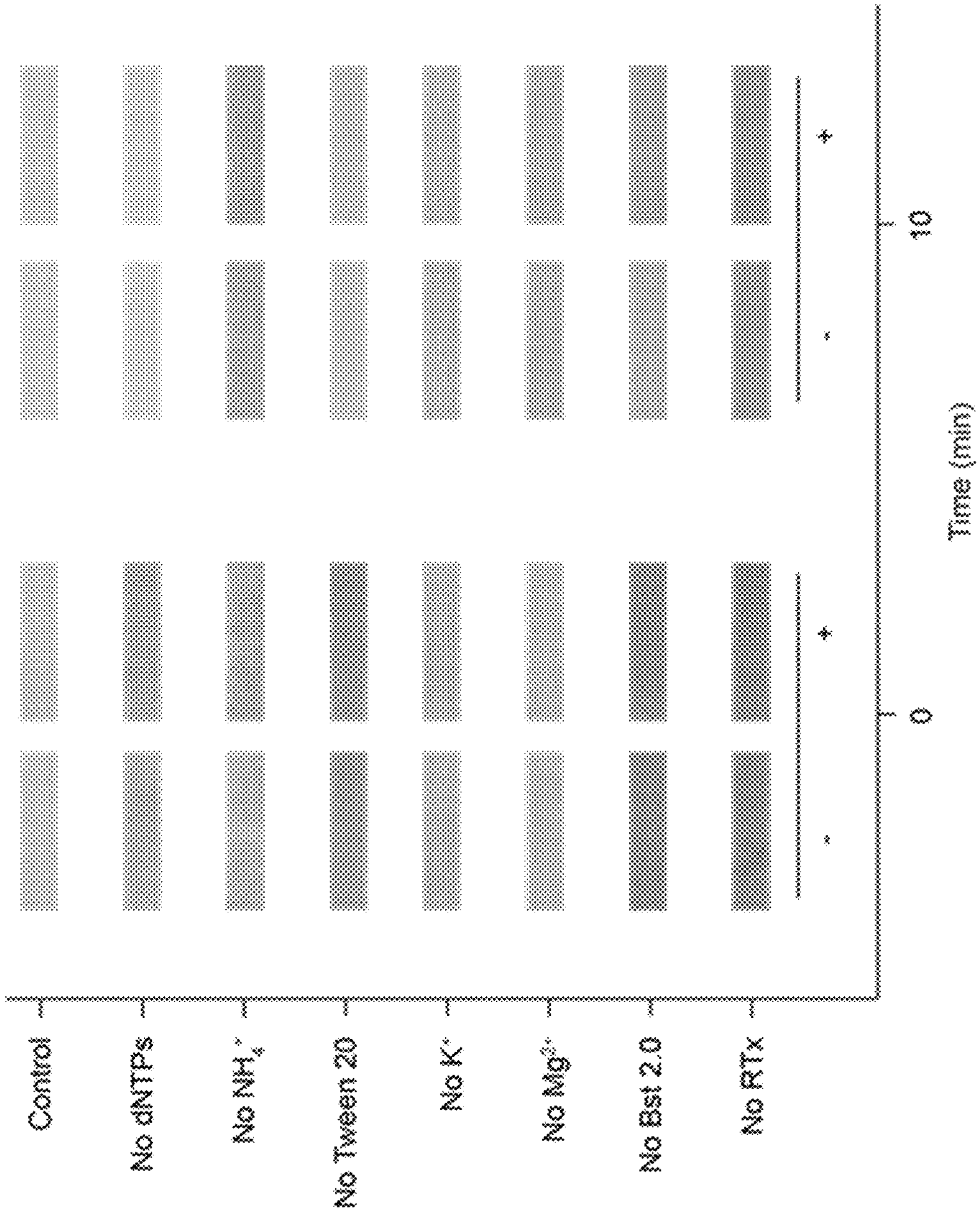
FIG. 21G illustrates the effect of elimination of single reactant on initial color of paper after drying in accordance with an example embodiment.
Figure 21H:
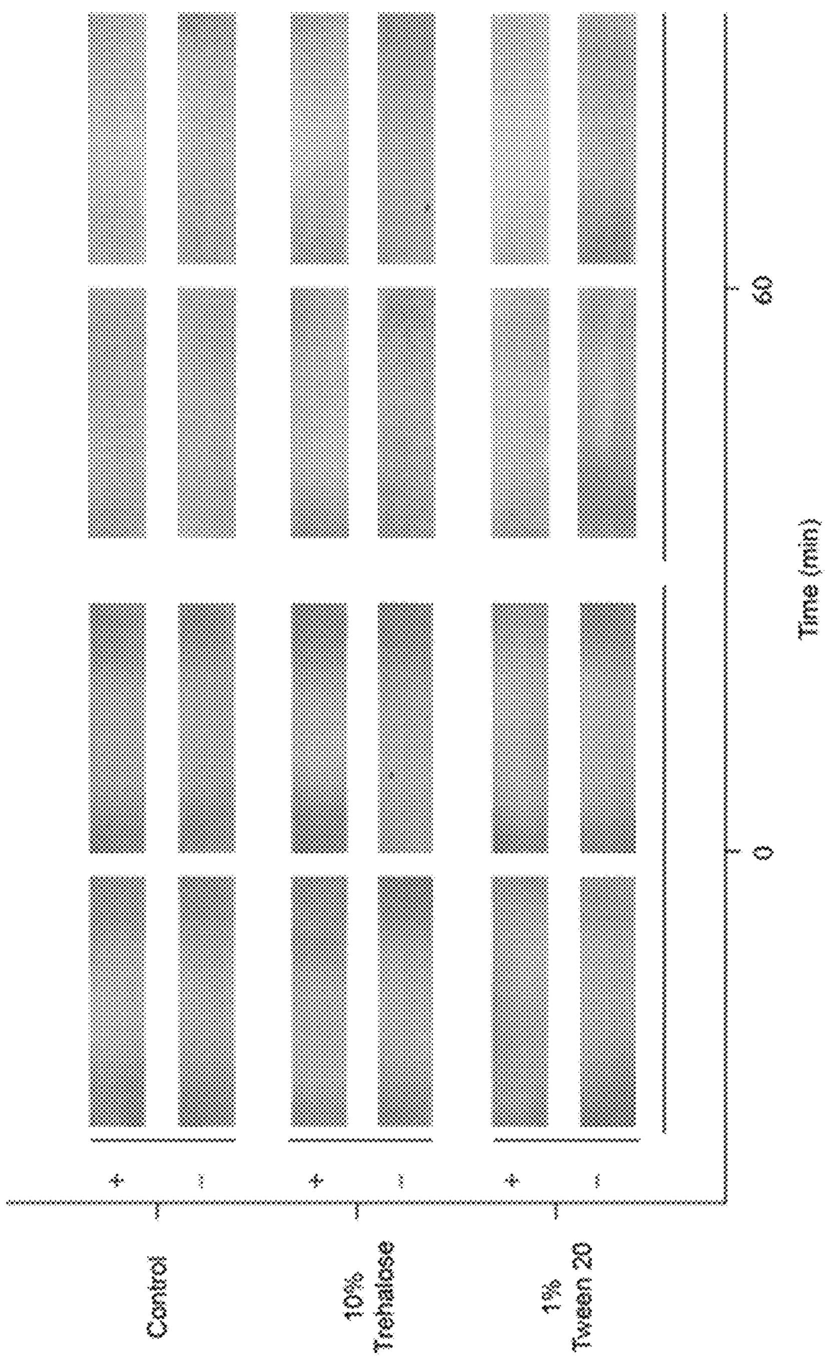
FIG. 21H illustrates the effect of Trehalose and Tween 20 on RT-LAMP colorimetric response in accordance with an example embodiment.

To reduce the complexity of the device, the components of the RT-LAMP reaction (without the template) were dried on the paper. Drying allows for stable distribution of the device and easy operation without compromising diagnostic performance; the user simply adds the sample to rehydrate the reagents. Upon drying the reagents on paper, the papers changed color from red to yellow over time without any template being present, indicating a decrease in the pH of the paper. Through a series of leave-one-out experiments, it was determined that ammonium sulfate was responsible for this change (FIG. 21G). This color change could result from the oxidation of cellulose caused by heating and the oxidizing nature of ammonium sulfate or the acidification of reagents by degassing of ammonia from the RT-LAMP mixture. To prevent the color change in the absence of amplification, ammonium sulfate was replaced with betaine and the concentration of phenol red was increased (which acts as an antioxidant) (FIG. 21H).

The effectiveness of betaine in LAMP reactions varies; however, betaine can reduce oxidative damage, and thus was included. Both trehalose and BSA were added to the formulation on paper (FIG. 21H).

Figure 21I:
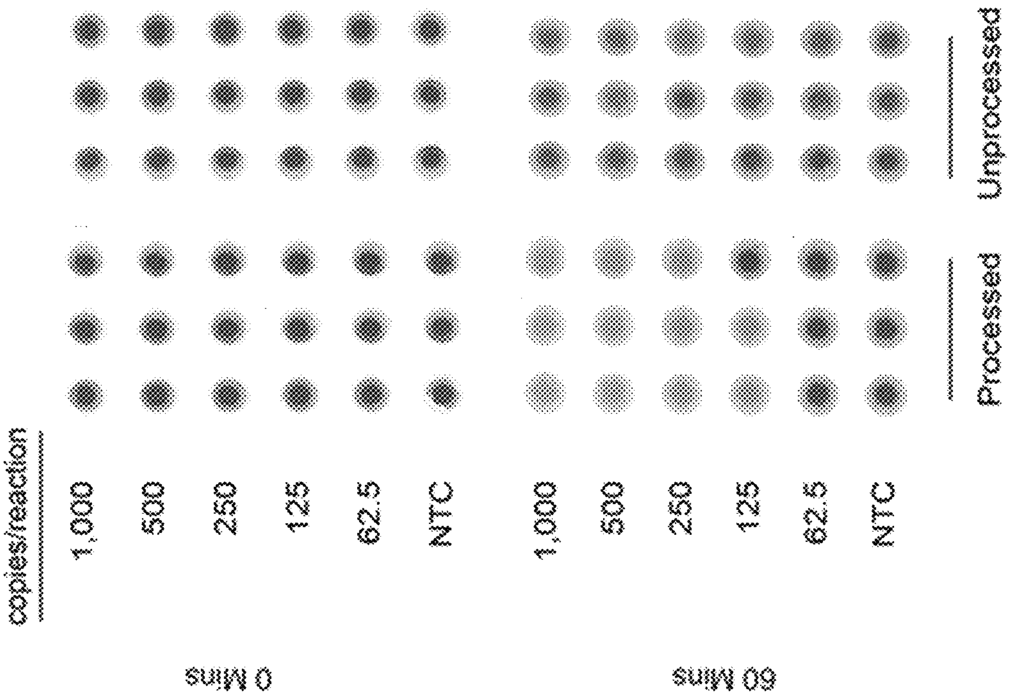
FIG. 21I illustrates the effect of saliva processing on colorimetric response in accordance with an example embodiment.

For the device, two reaction zones were used; one targeting SARS-CoV-2 and one providing a no-primer control to determine the stability of our reagents on paper (which should not react with any sample). A schematic of the final device is shown in FIG. 19C and results from the device with and without heat-inactivated SARS-CoV-2 spiked into saliva at 5% reaction concentration are shown in FIG. 19D. As shown in FIG. 19B, the LoD of the assay on paper (250 copies/reaction) is comparable to the LoD observed in solution for the colorimetric RT-LAMP formulation (FIG. 21I)

For the construction of the device, a Melinex® backing was used to provide structural support. Using a double-sided adhesive, two reaction pads were attached to the backing without altering their pH. The number of reaction zones can be arbitrarily increased to allow for multiplexed detection without altering the design of the device. 20 mil polystyrene spacers were added between reaction pads to provide a physical barrier inhibiting leakage from one reaction zone to an adjacent reaction zone, thus eliminating crosstalk during both reagent and sample addition. In some cases, the reaction zones can be separated by hydrophobic barriers resulting from wax printing preventing sample from crossing; however, to enable roll-to-roll manufacturing, wax usage was eliminated and spacers were used.

Example 25—Validation of Contrived Samples

To evaluate the analytical sensitivity and specificity of our assay on paper, contrived samples were generated with heat-inactivated SARS-CoV-2 at multiples of the LoD for orf7ab.I to run the RT-LAMP assay on paper. A total of 30 positive samples and 30 corresponding negative samples were used which is the minimum number for emergency use authorization (EUA) in the United States. To determine the colorimetric threshold to differentiate positive from negative reactions, an ROC curve was constructed by calculating the sensitivity and specificity at varying green channel intensity threshold values (FIG. 20). At the threshold, the assay had the following analytical metrics: sensitivity of 97%, specificity of 100%, and accuracy of 98% (FIG. 20A and FIG. 20B). The difference between the positive and negative groups were found to be significantly different ($p<0.001$). The paper strips were cut by hand and small differences in the size of the paper can cause differences in the colorimetric response. Therefore, large-scale fabrication and quality control can further enhance the consistency within the two groups (positive and negative). This sensitivity is comparable to assays using RNA extracts (sensitivity ~95%), and better than that reported for crude samples where significant decreases in sensitivity (to ~80%) are common.

Example 26—Colorimetric Interpretation of Paper-Based Device

To observe the effect of color perception on the performance of our device, four participants were surveyed and asked to interpret the results of the device. Each participant was provided with a color bar and scans of the device after 60 minutes (FIGS. 23A and 23B) and asked to classify the result as valid or invalid (using the control pad) and positive or negative based on the threshold marked on the color bar. The sensitivity and accuracy of the device decreased to 76% and 91%, respectively when user interpretation was introduced to the analysis (FIG. 19F). This low sensitivity stems from respondents identifying many positive reactions as invalid based on the control pad, leading to a false invalid rate of 25%, which may be attributed to contamination of the control pad with amplicons during the reaction. Additionally, user interpretation of the pads where regions of both yellow and red exist could introduce ambiguity, resulting in an increased false-positive rate or false invalid rate. Recent findings suggest this ambiguity is due to a third, intermediate color cluster (along with positive/negative clusters), that is not adequately addressed in colorimetric assays. Since invalid results were discarded from further analysis, this elevated false invalid rate may artificially influence the specificity and accuracy metrics of the device.

Example 27—Effect of Elimination of Single Reactant on Initial Color of Paper after Drying FIG. 21G shows that a 20 L of RT-LAMP master mix containing a base formulation of KCl (50 mM), $MgSO_4$ (8 mM), equimolar dNTP mixture (1.4 mM each dNTP), WarmStart BST 2.0 (0.32 U/μL), WarmStart RTx (0.3 U/μL), Phenol red (0.25 mM), dUTP (0.14 mM), Antarctic UDG (0.0004 U/μL), Tween 20 (1% v/v), $(NH_4)_2SO_4$ (10 mM), and Trehalose (10% w/v) along with 5 μL of nuclease-free water was added Grade 1 chromatography paper and allowed to dry inside a PCR preparation hood for 10 minutes. Reactants were left out of the base formulation as indicated to determine the cause of the observed color change upon drying. RT-LAMP primers and templates were not included in this study.

Example 28—Phenol Red Color Calibration at Various pH Values

FIG. 21B shows calibration of 250 μM phenol red at different pH values on paper buffered by 20 mM Tris. pH values were adjusted using HCl or KOH. The images of Grade 222 Chromatograph paper (5 mm×6 mm) were cropped in the shape of a rectangle such that colors could be compared easily across multiple strips.

Example 29—Validation of Final Device at Various Concentrations of Heat-Inactivated SARS-Cov-2

FIG. 21A shows RT-LAMP using orf7ab.I primer set and final formulation of colorimetric RT-LAMP master mix. The left reaction zone on each device is the no primer control wherein all orf7ab.I primers were replaced with water and not included in the master mix. The right reaction zone either contains heat-inactivated virus spiked into processed saliva at the indicated concentrations in the case of positive reactions, or processed saliva in the case of negative reactions. All processed saliva resulted in a final reaction concentration of 5%. Master mix consisted of KCl (50 mM), $MgSO_4$ (8 mM), equimolar dNTP mixture (1.4 mM each dNTP), WarmStart BST 2.0 (0.32 U/μL), WarmStart RTx (0.3 U/μL), Phenol red (0.25 mM), dUTP (0.14 mM), Antarctic UDG (0.0004 U/μL), Tween 20 (1% v/v), Betaine (20 mM), BSA (40 mg/mL), and Trehalose (10% w/v). Grade 222 chromatography paper was used.

Example 30—Green Channel Color Intensity of RT-LAMP Colorimetric Response at Varying Template Concentrations FIG. 21C shows a scatter plot of the colorimetric response of paper pads in at varying concentrations. The green color intensity threshold is showed with reference line 121.

Example 31—Effect of Heating Method on RT-LAMP Colorimetric Response

Figure 22C:
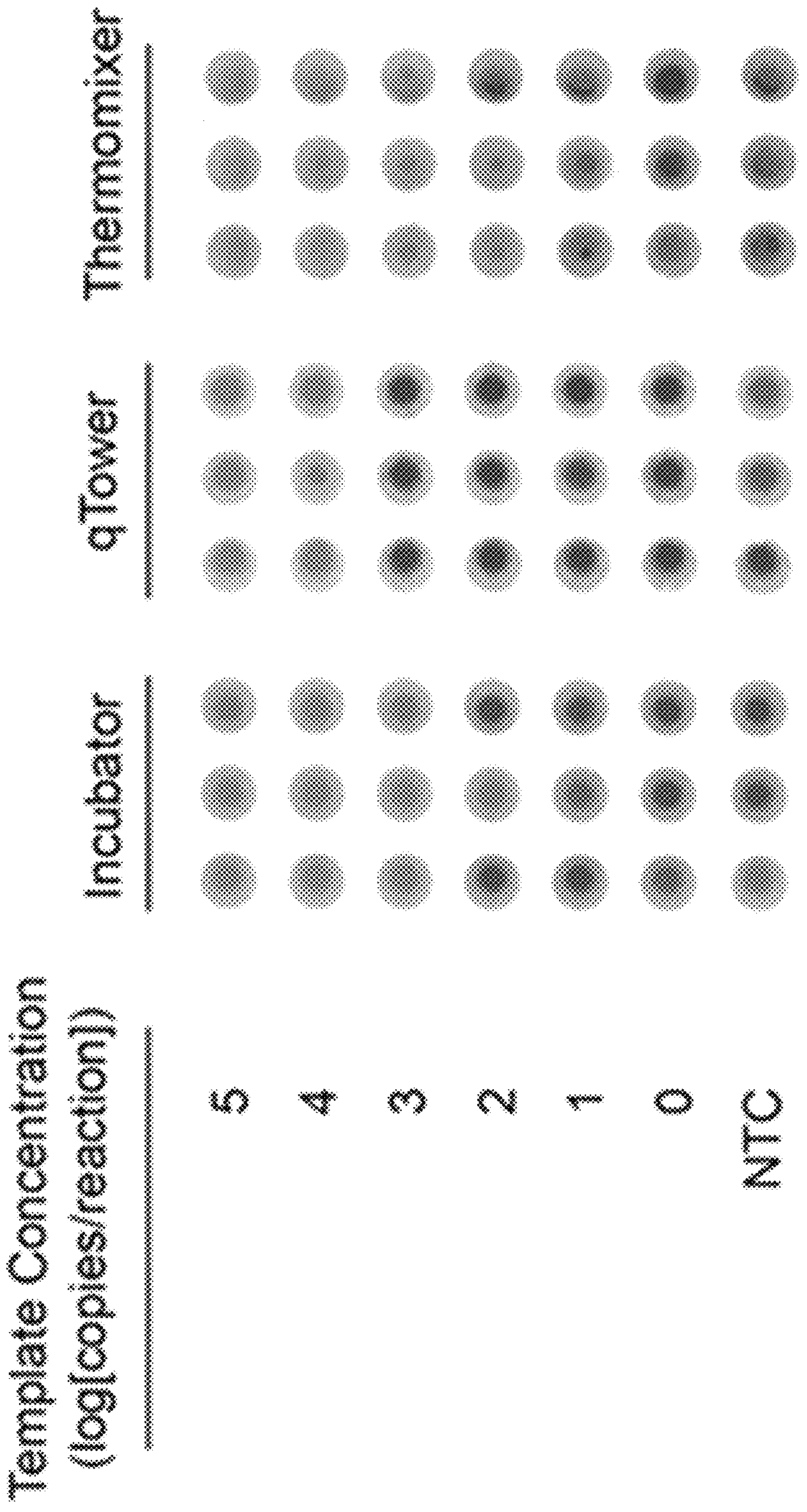
FIG. 22C illustrates the effect of the heating method on RT-LAMP colorimetric response in accordance with an example embodiment.

FIG. 22C shows colorimetric scans for limit of detection (LoD) of LAMP for 25 uL reactions across different heating devices after 60 minutes of incubation at 65° C. The primer set used for these reactions was orflab.II. 20 μL reaction mixtures were spiked with 5 μL of heat-inactivated virus dilutions in water to result in the final labeled concentrations (positive reactions) or nuclease-free water (negative). Reaction master mixes included 12.5 μL of NEB Colorimetric 2× master mix, 2.5 μL of primer mix, and 5 μL of water.

Example 32—Effect or Ramp Rate on RT-LAMP Colorimetric Response

Figure 22D:
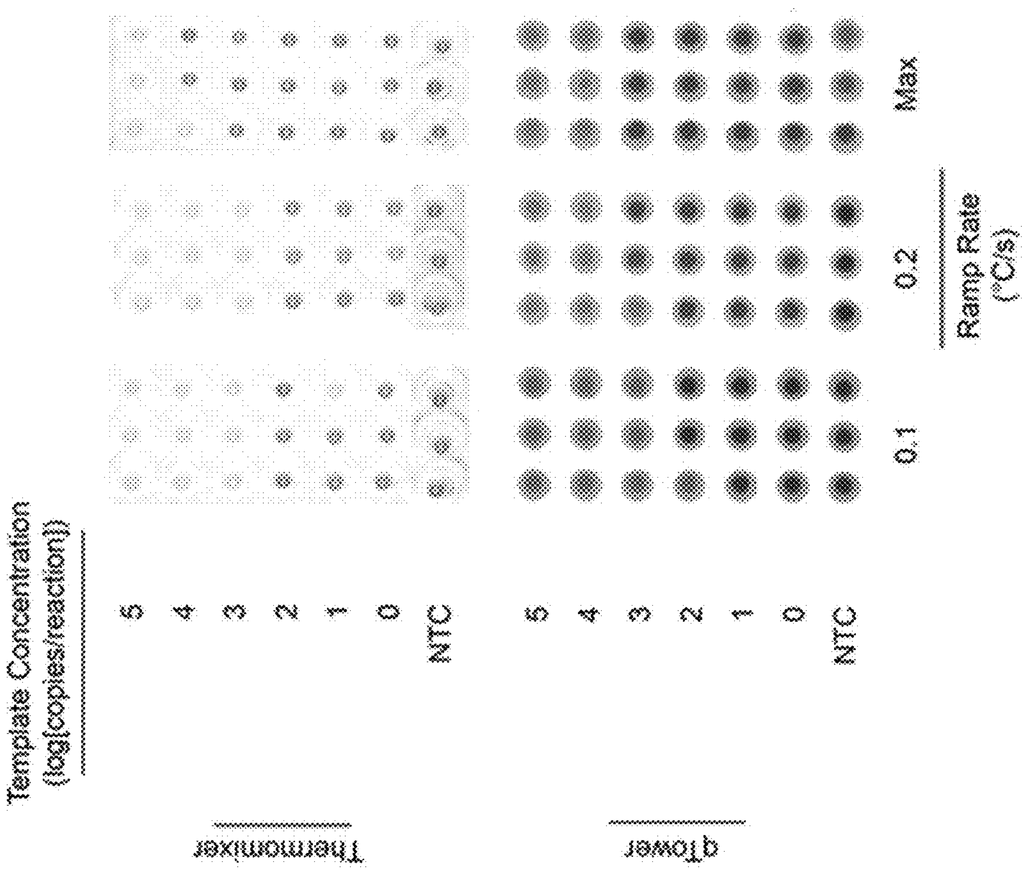
FIG. 22D illustrates the effect of the ramp rate on RT-LAMP colorimetric response in accordance with an example embodiment.

FIG. 22D shows colorimetric scans after 60 minutes of incubation at 65° C. for 254, reactions on the qTower (96-well plate) and thermocycler (PCR tubes) with varying ramp rates. The primer set used was orflab.II. 20 μL. Reaction mixtures were spiked with 5 μL of heat-inactivated virus dilutions in water to result in the final labeled concentrations (positive reactions) or nuclease-free water (negative). Reaction master mixes included 12.5 μL of NEB Colorimetric 2× master mix, 2.5 μL of primer mix, and 5 μL of water.

Example 33—Effect of Trehalose and Tween 20 on RT-LAMP Colorimetric Response

FIG. 21H shows colorimetric RT-LAMP results with the inclusion of Trehalose or Tween 20 at the given concentration. The orflab.II primer set was used. 20 μL of RT-LAMP master mix containing a base formulation of KCl (50 mM), $MgSO_4$ (8 mM), equimolar dNTP mixture (1.4 mM each dNTP), WarmStart BST 2.0 (0.32 U/μL), WarmStart RTx (0.3 U/μL), Phenol red (0.25 mM), dUTP (0.14 mM), Antarctic UDG (0.0004 U/μL), Tween 20 (1% v/v, if indicated), Betaine (20 mM), BSA (40 mg/mL), and Trehalose (10% w/v, if indicate) was added to Grade 1 chromatography paper (5 mm×20 mm) and allowed to dry inside a PCR preparation hood for 60 minutes. 25 μL of Heat-inactivated SARS-CoV-2 at a final concentration of $1\times10^5$ copies per reaction in 25% processed saliva (positive reactions) or nuclease-free water (negative reactions) was added to the dry reaction pads. The pads were heated in an incubator set at 65° C. for 60 minutes and then scanned using a flat bed scanner.

Inclusion of ammonium sulfate caused a color from red to yellow upon drying of RT-LAMP reagents when no template was present. This color change was prevented by increasing the phenol red concentration and replacing ammonium sulfate with betaine (FIG. 21G). Furthermore, the addition of trehalose and bovine serum albumin (BSA) increased the reaction speed and improved LoD (FIG. 21H).

Example 34—Summary

A paper-based device to detect nucleic acids of pathogens of interest in complex samples can use loop-mediated isothermal amplification (LAMP) by producing a colorimetric response visible to the human eye. To demonstrate the utility of this device in emerging public health emergencies, the device detected SARS-CoV-2 in human saliva without preprocessing. The resulting device was capable of detecting the virus within 60 minutes and had an analytical sensitivity of 97% and a specificity of 100% with a limit of detection of 200 genomic copies/4, of patient saliva using image analysis. The device included a configurable number of reaction zones constructed of Grade 222 chromatography paper separated by 20 mil polystyrene spacers attached to a Melinex® backing via an ARclean® double-sided adhesive. The resulting device could detect multiple targets and a variety of pathogens by changing the LAMP primer sets.

The platform has the following properties: i) it uses saliva, ii) it has minimal operator training, iii) it can be fabricated using roll-to-roll methods to achieve millions of tests, iv) it performs similar to a RT-qPCR assay in terms of analytical sensitivity and specificity, v) it provides a colorimetric response visible to the naked eye, vi) it is amenable to point-of-care use, vii) it provides results in less than 60 minutes, and viii) it is estimated to cost ~$10/test.

Due to the simplicity and scalability of this test, it could be used in a wide variety of settings, potentially including in-home diagnostics. The platform can be readily reconfigured to target different pathogens by screening primer sets in solution. Multiplexing is enabled by adding additional reaction sites to the device. The reconfigurable nature of the platform allows it to be used for detection of emerging pathogens in future public health emergencies.

EXAMPLE EMBODIMENTS

In one example there is provided, a system for a chromatic loop-mediated isothermal amplification (LAMP) analysis that includes or comprises a substantially non-reactive solid phase reaction medium; and a non-interfering reagent mixture.

In one example of a system for a chromatic loop-mediated isothermal amplification (LAMP) analysis, the substantially non-reactive solid phase reaction medium can have a buffering capacity from about 0.01 mM to about 5 mM.

In another example of a system for a chromatic loop-mediated isothermal amplification (LAMP) analysis, the substantially non-reactive solid phase reaction medium can have a $\lambda_{max}$ ranging from about 443 nm to about 570 nm.

In another example of a system for a chromatic loop-mediated isothermal amplification (LAMP) analysis, the substantially non-reactive solid phase reaction medium can comprise cellulose or glass fiber.

In another example of a system for a chromatic loop-mediated isothermal amplification (LAMP) analysis, the substantially non-reactive solid phase reaction medium can be hydrophilic, absorbent, and porous.

In another example of a system for a chromatic loop-mediated isothermal amplification (LAMP) analysis, the substantially non-reactive solid phase reaction medium can be substantially free of oxidizing agents and pH-interfering agents.

In another example of a system for a chromatic loop-mediated isothermal amplification (LAMP) analysis, the system can further comprise an adhesive; a spreading layer; a spacer; and a plastic carrier, wherein each of the adhesive, spreading layer, spacer, and plastic carrier are substantially free of oxidizing agents and pH-interfering agents.

In another example of a system for a chromatic loop-mediated isothermal amplification (LAMP) analysis, the non-interfering reagent mixture can further comprise one or more target primers, DNA polymerase, and a re-solubilization agent.

In another example there is provided, a method of maximizing accuracy of a chromatic output signal in a solid phase pH-dependent loop-mediated isothermal amplification (LAMP) analysis that can comprise: providing a solid phase reaction medium that minimizes non-LAMP reaction produced discoloration; and performing the LAMP analysis on the solid phase reaction medium.

In one example of a method of maximizing accuracy of a chromatic output signal in a solid phase pH-dependent loop-mediated isothermal amplification (LAMP) analysis, the method can further comprise controlling non-LAMP produced discoloration from non-LAMP reaction produced protons.

In another example of a method of maximizing accuracy of a chromatic output signal in a solid phase pH-dependent loop-mediated isothermal amplification (LAMP) analysis, the method can further comprise controlling non-LAMP reaction produced discoloration using a non-discoloration additive.

In another example of a method of maximizing accuracy of a chromatic output signal in a solid phase pH-dependent loop-mediated isothermal amplification (LAMP) analysis, the non-discoloration additive can comprise a sugar, a buffer, a blocking agent, or combinations thereof.

In another example of a method of maximizing accuracy of a chromatic output signal in a solid phase pH-dependent loop-mediated isothermal amplification (LAMP) analysis, the non-discoloration additive can comprise a sugar comprising one or more of trehalose, glucose, sucrose, dextran, or combinations thereof.

In another example of a method of maximizing accuracy of a chromatic output signal in a solid phase pH-dependent loop-mediated isothermal amplification (LAMP) analysis, the non-discoloration additive can comprise a blocking agent comprising bovine serum albumin, casein, or combinations thereof.

In another example of a method of maximizing accuracy of a chromatic output signal in a solid phase pH-dependent loop-mediated isothermal amplification (LAMP) analysis, a method of maximizing a level of detection (LOD) in a loop-mediated isothermal amplification (LAMP) analysis can comprise providing a reaction environment and reagents that minimize non-LAMP reaction products.

In another example of a method of maximizing accuracy of a chromatic output signal in a solid phase pH-dependent loop-mediated isothermal amplification (LAMP) analysis, a system for a chromatic loop-mediated isothermal amplification (LAMP) analysis can comprise a combination of a solid phase reaction medium and LAMP reagents which when stored at 25° C. maintain a coloration of the solid phase reaction medium that is within 10% of an initial shade of the solid phase medium.

In one example of a method of maximizing accuracy of a chromatic output signal in a solid phase pH-dependent loop-mediated isothermal amplification (LAMP) analysis, the combination can maintain the coloration when stored for longer than one or more of: 30 days, 90 days, 365 days, 2 years, or 5 years.

In another example of a method of maximizing accuracy of a chromatic output signal in a solid phase pH-dependent loop-mediated isothermal amplification (LAMP) analysis, the combination can maintain the coloration when stored at a relative humidity between about 40% and 90% at 25° C.

In another example there is provided, a method for manufacturing a chromatic LAMP system as recited herein that can comprise combining the non-interfering reagent mixture with a substantially non-reactive solid-phase reaction medium such that the non-interfering reagent mixture is held in contact with the substantially non-reactive solid-phase reaction medium.

In one example of a method for manufacturing a chromatic LAMP system as recited herein the manufacturing process can comprise: preparing a solution containing the non-interfering reagent mixture; and coating the reagent mixture onto the substantially non-reactive solid-phase reaction medium.

In another example of a method for manufacturing a chromatic LAMP system as recited herein the coating can comprise dropping, spraying, dipping, soaking, or misting the solution onto the substantially non-reactive solid phase reaction medium.

In another example of a method for manufacturing a chromatic LAMP system as recited herein the non-interfering reagent mixture can be combined with the substantially non-reactive solid-phase reaction medium using a reel-to-reel (R2R) process.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A system for a chromatic loop-mediated isothermal amplification (LAMP) analysis comprising:

a substantially non-reactive solid phase reaction medium; and a non-interfering reagent mixture.

2. The system of claim 1, wherein the substantially non-reactive solid phase reaction medium has a buffering capacity from about 0.01 mM to about 5 mM.

3. The system of claim 1, wherein the substantially non-reactive solid phase reaction medium has a Amax ranging from about 443 nm to about 570 nm.

4. The system of claim 1, wherein the substantially non-reactive solid phase reaction medium comprises cellulose or glass fiber.

5. The system of claim 1, wherein the substantially non-reactive solid phase reaction medium is hydrophilic, absorbent, and porous.

6. The system of claim 1, wherein the substantially non-reactive solid phase reaction medium is substantially free of oxidizing agents and pH-interfering agents.

7. The system of claim 1, further comprising:

an adhesive;

a spreading layer; a spacer; and a plastic carrier, wherein each of the adhesive, spreading layer, spacer, and plastic carrier are substantially free of oxidizing agents and pH-interfering agents.

8. The system of claim 1, wherein the non-interfering reagent mixture further comprises: one or more target primers, DNA polymerase, and a re-solubilization agent.

9. A method of maximizing accuracy of a chromatic output signal in a solid phase pH-dependent loop-mediated isothermal amplification (LAMP) analysis comprising:

providing a solid phase reaction medium that minimizes non-LAMP reaction produced discoloration; and performing the LAMP analysis on the solid phase reaction medium.

10. The method of claim 9, further comprising:

controlling non-LAMP produced discoloration from non-LAMP reaction produced protons.

11. The method of claim 9, further comprising:

controlling non-LAMP reaction produced discoloration using a non-discoloration additive.

12. The method of claim 11, wherein the non-discoloration additive comprises a sugar, a buffer, a blocking agent, or combinations thereof.

13. The method of claim 11, wherein the non-discoloration additive comprises a sugar comprising one or more of trehalose, glucose, sucrose, dextran, or combinations thereof.

14. The composition of claim 11, wherein the non-discoloration additive comprises a blocking agent comprising bovine serum albumin, casein, or combinations thereof.

15. A method of maximizing a level of detection (LOD) in a loop-mediated isothermal amplification (LAMP) analysis comprising:

providing a reaction environment and reagents that minimize non-LAMP reaction products.

16. A system for a chromatic loop-mediated isothermal amplification (LAMP) analysis comprising:

a combination of a solid phase reaction medium and LAMP reagents which when stored at 25° C. maintain a coloration of the solid phase reaction medium that is within 10% of an initial shade of the solid phase medium.

17. The system of claim 16, wherein the combination maintains the coloration when stored for longer than one or more of: 30 days, 90 days, 365 days, 2 years, or 5 years.

18. The system of claim 16, wherein the combination maintains the coloration when stored at a relative humidity between about 40% and 90% at 25° C.

19. A method for manufacturing a chromatic LAMP system as recited in claim 1, comprising:

combining the non-interfering reagent mixture with a substantially non-reactive solid-phase reaction medium such that the non-interfering reagent mixture is held in contact with the substantially non-reactive solid-phase reaction medium.

20. The method of claim 19, wherein the manufacturing process comprises: preparing a solution containing the non-interfering reagent mixture; and coating the reagent mixture onto the substantially non-reactive solid-phase reaction medium.

21. The method of claim 20, wherein the coating comprises dropping, spraying, dipping, soaking, or misting the solution onto the substantially non-reactive solid phase reaction medium.

22. The method of claim 19, wherein the non-interfering reagent mixture is combined with the substantially non-reactive solid-phase reaction medium using a reel-to-reel (R2R) process.

* * * * *